(12) United States Patent
Nyati et al.

(10) Patent No.: US 11,999,731 B2
(45) Date of Patent: *Jun. 4, 2024

(54) EGFR DIMER DISRUPTORS AND USE OF THE SAME

(71) Applicant: THE REGENTS OF THE UNIVERSITY OF MICHIGAN, Ann Arbor, MI (US)

(72) Inventors: Mukesh K. Nyati, Superior Township, MI (US); Theodore S. Lawrence, Ann Arbor, MI (US); Christopher Whitehead, Ann Arbor, MI (US); Jason Christopher Rech, Ann Arbor, MI (US); Brennan Taylor Watch, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 20 days.

This patent is subject to a terminal disclaimer.

(21) Appl. No.: 17/739,358

(22) Filed: May 9, 2022

(65) Prior Publication Data

US 2022/0340572 A1    Oct. 27, 2022

Related U.S. Application Data

(63) Continuation of application No. 16/970,655, filed as application No. PCT/US2019/019391 on Feb. 25, 2019, now Pat. No. 11,358,965.

(60) Provisional application No. 62/634,452, filed on Feb. 23, 2018.

(51) Int. Cl.
*C07D 471/10* (2006.01)
*C07D 233/70* (2006.01)
*C07D 233/84* (2006.01)

(52) U.S. Cl.
CPC ......... *C07D 471/10* (2013.01); *C07D 233/70* (2013.01); *C07D 233/84* (2013.01)

(58) Field of Classification Search
CPC .................................................. C07D 471/10
USPC ...................................................... 514/278
See application file for complete search history.

(56) References Cited

U.S. PATENT DOCUMENTS

| 3,547,977 A | 12/1970 | Richter |
| 5,466,468 A | 11/1995 | Schneider et al. |
| 9,029,502 B2 | 5/2015 | Nyati et al. |
| 2009/0163545 A1 | 6/2009 | Goldfarb |
| 2012/0190622 A1 | 7/2012 | Nyati et al. |
| 2015/0218277 A1 | 8/2015 | Nyati et al. |

FOREIGN PATENT DOCUMENTS

| WO | WO-2012/087943 A2 | 6/2012 |
| WO | WO-2014/176475 A2 | 10/2014 |
| WO | WO-2019/165358 A1 | 8/2019 |

OTHER PUBLICATIONS

STN Registry 1189728-36-6 (Oct. 23, 2009).
Ahsan et al., Destabilization of the epidermal growth factor receptor (EGFR) by a peptide that inhibits EGFR binding to heat shock protein 90 and receptor dimerization, J Biol Chem. 2013;288:26879-86.
Ahsan et al., Efficacy of an EGFR-specific peptide against EGFR-dependent cancer cell lines and tumor xenografts, Neoplasia. 2014;16:105-14.
Ahsan et al., Role of epidermal growth factor receptor degradation in cisplatin-induced cytotoxicity in head and neck cancer, *Cancer Res.*, 70:2862-9 (2010).
Amador et al., An epidermal growth factor receptor intron 1 polymorphism mediates response to epidermal growth factor receptor inhibitors, Cancer Res. 2004;64:9139-43.
Argiris et al., Early tumor progression associated with enhanced EGFR signaling with bortezomib, cetuximab, and radiotherapy for head and neck cancer, Clin Cancer Res. 2011;17:5755-64.
Arulananda et al., Combination Osimertinib and Gefitinib in C797S and T790M EGFR-Mutated Non-Small Cell Lung Cancer, J Thorac Oncol., 2017;12:1728-32.
Balak et al., Novel D761Y and common secondary T790M mutations in epidermal growth factor receptor-mutant lung adenocarcinomas with acquired resistance to kinase inhibitors, Clin Cancer Res. 2006;12:6494-501.
Bhatia et al., A review on bioisosterism: A rational approach for drug design and molecular modification, Pharmacologyonline, 1:272-99 (2011).
Bondeson et al., Catalytic in vivo protein knockdown by small-molecule PROTACs, Nat. Chem. Biol., 11(8):611-7 (Aug. 2015).
Bublil et al., Kinase-mediated quasi-dimers of EGFR, FASEB J. 2010;24:4744-55.
Burslem et al., The Advantages of Targeted Protein Degradation Over Inhibition: An RTK Case Study, Cell Chem Biol. 2018;25:67-77.
Cai et al., A potent and orally active antagonist (SM-406/AT-406) of multiple inhibitor of apoptosis proteins (IAPs) in clinical development for cancer treatment, J. Med. Chem., 54(8):2714-26 (2011).
Chmielecki et al., Optimization of dosing for EGFR-mutant non-small cell lung cancer with evolutionary cancer modeling, Sci Transl Med. 2011;3:90ra59.
Chung et al., Spatial control of EGF receptor activation by reversible dimerization on living cells, Nature. 2010;464:783-7.
Coban et al., Effect of phosphorylation on EGFR dimer stability probed by single-molecule dynamics and FRET/FLIM, Biophys J. 2015;108:1013-26.
Corcoran et al., EGFR-mediated re-activation of MAPK signaling contributes to insensitivity of BRAF mutant colorectal cancers to RAF inhibition with vemurafenib, Cancer Discovery. 2012;2:227-35.

(Continued)

*Primary Examiner* — Taofiq A Solola
(74) *Attorney, Agent, or Firm* — MARSHALL, GERSTEIN & BORUN LLP

(57) ABSTRACT

Provided herein are compounds that modulate EGFR and methods of using the same, for example to treat cancer.

20 Claims, 11 Drawing Sheets

(56) References Cited

OTHER PUBLICATIONS

Crews et al., Inducing Protein Degradation as a Therapeutic Strategy, J Med Chem. 2016;59:5129-30.
Cuneo et al., EGFR targeted therapies and radiation: Optimizing efficacy by appropriate drug scheduling and patient selection, Pharmacol Ther. 2015;154:67-77.
Dahabreh et al., Somatic EGFR mutation and gene copy gain as predictive biomarkers for response to tyrosine kinase inhibitors in non-small cell lung cancer, Clin Cancer Res. 2010;16:291-303.
Database CAPLUS [Online], STN Accession No. 1793, Database Accession No. 2006:546112 (Goldfarb, Method using lifespan-altering compounds for altering the lifespan of eukaryotic organisms, and screening for such compounds) (Dec. 22, 2008).
Ewald et al., Ligand- and kinase activity-independent cell survival mediated by the epidermal growth factor receptor expressed in 32D cells, Exp Cell Res. 2003;282:121-31.
Fang et al. Predictive physiologically based pharmacokinetic model for antibody-directed enzyme prodrug therapy, Drug Metab. Dispos. 2008;36:1153-65.
Fang et al., Population pharmacokinetics of humanized monoclonal antibody HuCC49deltaCH2 and murine antibody CC49 in colorectal cancer patients, J. Clin. Pharmacol., 47(2):227-37 (2007).
Feng et al., Role of epidermal growth factor receptor degradation in gemcitabine-mediated cytotoxicity, Oncogene. 2007;26:3431-9.
Han et al., Landscape of EGFR signaling network in human cancers: biology and therapeutic response in relation to receptor subcellular locations, Cancer Lett. 2012;318:124-34.
Hines et al., Posttranslational protein knockdown coupled to receptor tyrosine kinase activation with phosphoPROTACs, Proc Natl Acad Sci U S A. 2013;110:8942-7.
Ichihara et al., SFK/FAK Signaling Attenuates Osimertinib Efficacy in Both Drug-Sensitive and Drug-Resistant Models of EGFR-Mutant Lung Cancer, Cancer Res. 2017;77:2990-3000.
International Application No. PCT/US19/19391, International Search Report and Written Opinion, dated May 29, 2019.
Jia et al., Overcoming EGFR(T790M) and EGFR(C797S) resistance with mutant-selective allosteric inhibitors, Nature. 2016;534:129-32.
Khana et al., Molecular imaging of epidermal growth factor receptor kinase activity, Anal. Biochem. 2011;417:57-64.
Kong et al., Structural pharmacological studies on EGFR T790M/C797S, Biochem Biophys Res Commun. 2017;488:266-72.
Leighl et al., Phase 2 Study of Erlotinib in Combination With Linsitinib (OSI-906) or Placebo in Chemotherapy-Naive Patients With Non-Small-Cell Lung Cancer and Activating Epidermal Growth Factor Receptor Mutations, Clin Lung Cancer. 2017;18:34-42.
Li et al., Roles of autophagy in cetuximab-mediated cancer therapy against EGFR, Autophagy. 2010;6:1066-77.
Lichtner et al., Signaling-inactive epidermal growth factor receptor/ligand complexes in intact carcinoma cells by quinazoline tyrosine kinase inhibitors, Cancer Research. 2001;61:5790-5.
Lovly et al., Rationale for co-targeting IGF-1R and ALK in ALK fusion-positive lung cancer, Nat Med. 2014;20:1027-34.
Ma et al., Discovery and characterization of LY2784544, a small-molecule tyrosine kinase inhibitor of JAK2V617F, Blood Cancer J. 2013; 3(4):e109.
Midha et al., EGFR mutation incidence in non-small-cell lung cancer of adenocarcinoma histology: a systematic review and global map by ethnicity (mutMapll), Am J Cancer Res. 2015;5:2892-911.
Morgan et al., Patient-Derived Xenograft Models of Non-Small Cell Lung Cancer and Their Potential Utility in Personalized Medicine, Front Oncol. 2017;7:2.
Niederst et al., The Allelic Context of the C797S Mutation Acquired upon Treatment with Third- Generation EGFR Inhibitors Impacts Sensitivity to Subsequent Treatment Strategies, Clin Cancer Res. 2015;21:3924-33.
Pan et al., Development and Characterization of Bladder Cancer Patient-Derived Xenografts for Molecularly Guided Targeted Therapy, PLoS One 2015, 10(8): e0134346.
Pao et al., Acquired resistance of lung adenocarcinomas to gefitinib or erlotinib is associated with a second mutation in the EGFR kinase domain, PLoS Med. 2005;2:e73.
Piao et al., Oncolytic adenovirus retargeted to Delta-EGFR induces selective antiglioma activity, Cancer Gene Ther. 2009;16:256-65.
PUBCHEM-CID: 22428840, create date Dec. 5, 2007.
PUBCHEM-CID: 50744574, create date Feb. 22, 2011.
Raina et al., PROTAC-induced BET protein degradation as a therapy for castration-resistant prostate cancer, Proc. Natl. Acad. Sci. USA, 113(26):7124-9 (Jun. 2016).
Ray et al., Differential protein stability of EGFR mutants determines responsiveness to tyrosine kinase inhibitors, Oncotarget. 2016; 7(42):68597-68613.
Ray et al., Inducing Oncoprotein Degradation to Improve Targeted Cancer Therapy, Neoplasia. 2015;17:697-703.
Ray et al., Regulation of EGFR protein stability by the HECT-type ubiquitin ligase SMURF2, Neoplasia. 2011;13:570-8.
Ripphausen et al., State-of-the-art in ligand-based virtual screening, Drug Discov Today. 2011;16:372-6.
Rudin et al., Lung cancer in never smokers: molecular profiles and therapeutic implications, Clin Cancer Res. 2009;15:5646-61.
Sangodkar et al., Targeting the FOXO1/KLF6 axis regulates EGFR signaling and treatment response, J Clin Invest. 2012;122:2637-51.
Shukla et al., KRAS protein stability is regulated through SMURF2: UBCH5 complex-mediated ?- TrCP1 degradation, Neoplasia. 2014;16:115-28.
Soria et al., Osimertinib in Untreated EGFR-Mutated Advanced Non-Small-Cell Lung Cancer, N Engl J Med. 2018;378:113-25.
Spivak-Kroizman et al., Heterodimerization of c-erbB2 with different epidermal growth factor receptor mutants elicits stimulatory or inhibitory responses, J Biol Chem. 1992;267:8056-63.
Sun et al., Potent bivalent Smac mimetics: effect of the linker on binding to inhibitor of apoptosis proteins (IAPs) and anticancer activity, J Med Chem. 2011;54:3306-18.
Thress et al., Acquired EGFR C797S mutation mediates resistance to AZD9291 in non-small cell lung cancer harboring EGFR T790M, Nat Med. 2015;21:560-2.
Torchilin et al., Peptide and protein drug delivery to and into tumors: challenges and solutions, Drug Discov Today. 2003;8:259-66.
Walker et al., Activation of the Ras/mitogen-activated protein kinase pathway by kinase-defective epidermal growth factor receptors results in cell survival but not proliferation, Mol Cell Biol. 1998;18:7192-204.
Wang et al., Treatment of glioblastoma multiforme using a combination of small interfering RNA targeting epidermal growth factor receptor and ?- catenin, J Gene Med. 2013;15:42-50.
Wei et al., EGFR-mediated Beclin 1 phosphorylation in autophagy suppression, tumor progression, and tumor chemoresistance, Cell. 2013;154:1269-84.
Weihua et al., Survival of cancer cells is maintained by EGFR independent of its kinase activity, Cancer Cell. 2008;13:385-93.
Wheeler et al., Understanding resistance to EGFR inhibitors-impact on future treatment strategies, Nat Rev Clin Oncol. 2010;7:493-507.
Yu et al., Acquired Resistance of EGFR-Mutant Lung Cancer to a T790M-Specific EGFT Inhibitor: Emergence of a Third Mutation (C797S) in the EGFR Tyrosine Kinase Domain, JAMA Oncol. 2015;1(7):982-4.
Yu et al., Examination of the pharmacokinetics of active ingredients of ginger in humans, AAPS J., 13(3):417-26 (2011).
Yun et al., The T790M mutation in EGFR kinase causes drug resistance by increasing the affinity for ATP, Proc Natl Acad Sci U S A. 2008;105:2070-5.
Zhang et al., An allosteric mechanism for activation of the kinase domain of epidermal growth factor receptor, Cell. 2006;125:1137-49.
Zhang et al., Inhibition of the EGF receptor by binding of MIG6 to an activating kinase domain interface, Nature. 2007;450:741-4.
Zheng et al., In vitro metabolism of 17-(dimethylaminoethylamino)-17-demethoxygeldanamycin in human liver microsomes, Drug Metab. Dispos. 2011;39:627-35.

(56) References Cited

OTHER PUBLICATIONS

Zou et al., Prediction of volume of distribution at steady state in humans: comparison of different approaches, Expert Opin Drug Metab Toxicol. 2012;8:855-72.

CAS Registry No. 1189452-92-3, Acetamide, N-(3-chloro-4-methoxyphenyl)-2-[(3-(4-fluorophenyl)-8-methyl-1,4,8-triazaspiro[4.5]deca-1,3-dien-2-yl]thio] (Oct. 22, 2009).

CAS Registry No. 1185121-75-8, Acetamide, 2-{[3-(4-bromophenyl)-8-methyl-1,4,8-triazaspiro[4.5]deca-1,3-dien-2-yl]thio]-N(3,4-difluorophenyl) (Sep. 16, 2009).

CAS Registry No. 1184994-02-2, Acetamide, N-(3-chloro-4-methoxyphenyl)-2-[[3-(4-methyoxyphenyl)-8-methyl-1,4,8-triazaspiro[4.5]deca-1,3-dien-2-yl]thio]acetamide (Sep. 16, 2009).

CAS Registry No. 899932-84-4, Acetamide, N-(3-chloro-4-fluorophenyl)-2-[[3-(4-methylphenyl)-1,4—diazaspiro[4.5]deca-1,3-dien-2-yl]thio] (Aug. 9, 2006).

CAS Registry No. 899932-27-5, Acetamide, N-(3,4-dichlorophenyl)-2-[[5-(3,4-dichlorophenyl)-2,2-dimethyl-2H-imidazol-4-yl]thio] (Aug. 9, 2006).

CAS Registry No. 1233854-83-8, Acetamide, N-2-thiazolyl-2-[[3-(2-thienyl)-1,4-diazaspiro[4.5]deca-1,3-dien-2-yl]thio] (May 16, 2010).

CAS Registry No. 1351770-20-1, Acetamide, 2-[[3-(4-butoxyphenyl)-1,4-diazaspiro[4.5]deca-1,3-dien-2-yl]thio]-N-(5-methyl-3-isoxazolyl) (Dec. 23, 2011).

CAS Registry No. 1223821-89-3, Acetamide, N-(3,4-difluorophenyl)-2-[[8-methyl-3-(4-methylphenyl)-1,4,8-triazaspiro[4.5]deca-1,3-dien-2-yl]thio] (May 16, 2010).

CAS Registry No. 1216844-66-4, Acetamide, N-(2,3-dihydro-1,4-benzodioxin-6-yl)-2-[[8-methyl-3-(4-methylphenyl)-1,4,8-triazaspiro[4.5]deca-1,3-dien-2-yl]thio] (Apr. 5, 2010).

CAS Registry No. 1216783-49-1, Acetamide, 2-[[3-(4-chlorophenyl)-8-methyl-1,4,8-triazaspiro[4.5]deca-1,3-dien-2-yl]thio]-N-(3,4-difluorophenyl) (Apr. 5, 2010).

CAS Registry No. 1190012-29-3, Acetamide, N-(3,4-difluorophenyl)-2-[[3-(4-fluorophenyl)-8-1,4,8-triazaspiro[4.5]deca-1,3-dien-2-yl]thio] (Oct. 25, 2009).

CAS Registry No. 1189949-77-6, Acetamide, N-(3-chloro-4-methoxyphenyl)-2-[[3-[4-(1,1-dimethylethyl)phenyl]-8-methyl-1,4,8-triazaspiro[4.5]deca-1,3-dien-2-yl]thio] (Oct. 25, 2009).

CAS Registry No. 1189913-29-8, Acetamide, N-(3,4-difluorophenyl)-2-[[3-(4-(1,1-dimethylethyl)phenyl]-8-methyl-1,4,8-triazapiro[4.5]deca-1,3,-dien-2-yl]thio] (Oct. 25, 2009).

Ardito et al., EGF receptor is required for KRAS-induced pancreatic tumorigenesis, Cancer Cell, 22(3), 304-317 (2012).

Banker et al., Pharmaceutics and Pharmacy Practice, eds., pp. 238-250 (1982).

Berge et al., Pharmaceutical Salts, Journal of Pharmaceutical Sciences, 66, 1-19 (Jan. 1977).

Burslem et al., The Advantages of Targeted Protein Degradation Over Inhibition: An RTK Case Study, Cell Chemical Biology, 25(1), 67 (2018).

Cox et al., Targeting RAS Membrane Association: Back to the Future for Anti-RAS Drug Discovery?, Clin Cancer Res, 21(8), 1819-1827 (2015).

Cromm et al., Addressing Kinase-Independent Functions of Fak via PROTAC-Mediated Degradation, Journal of the American Chemical Society, 140(49), 17019-17026 (2018).

Forrester et al., Site-specific analysis of protein S-acylation by resin-assisted capture, J Lipid Res, 52(2), 393-398 (2011).

International Application No. PCT/US2021/020990, International Search Report and Written Opinion, dated Jul. 20, 2021.

Kharbanda et al., Blocking EGFR palmitoylation suppresses PI3K signaling and mutant KRAS lung tumorigenesis, Science Signaling, 1-13 (Mar. 2020).

Kharbanda et al., Induced sensitivity to EGFR inhibitors is mediated by palmitoylated cysteine 1025 of EGFR and requires oncogenic Kras, Biochem Biophys Res Commun, 493(1), 213-219 (2017).

Knickelbein et al., Mutant KRAS as a critical determinant of the therapeutic response of colorectal cancer, Genes & Diseases, 2(1), 4-12 (Oct. 2014).

Lee et al., A small molecule approach to degrade RAS with EGFR repression is a potential therapy for KRAS mutation-driven colorectal cancer resistance to cetuximab, Exp Mol Med, 50(11), 153 (2018).

Navas et al., EGF receptor signaling is essential for k-ras oncogene-driven pancreatic ductal adenocarcinoma, Cancer Cell, 22(3), 318-330 (2012).

Nussinov et al., Intrinsic protein disorder in oncogenic KRAS signaling, Cell Mol Life Sci, 74(17), 3245-3261 (2017).

PubChem SID-132023783, 7 pages (May 31, 2019).

PubChem SID-278051878, 5 pages (Jan. 12, 2016).

Shan et al., Oncogenic Mutations Counteract Intrinsic Disorder in the EGFR Kinase and Promote Receptor Dimerization, Cell, 149(4), 860-870 (2012).

Shao et al., Evaluation of C-11 N-Methyl Lansoprazole as a Radiopharmaceutical for PET Imaging of Tau Neurofibrillary Tangles, ACS Med Chem Lett, 3(11), 936-941 (2012).

Trissel, ASHP Handbook on Injectable Drugs, 4th ed., 622-630 (1986).

A DGD1202 competes with Disruptin for EGFR binding

DGD1202 enhances thermal stability of purified EGFR

EGFR DIMER DISRUPTORS AND USE OF THE SAME

BACKGROUND

The EGFR small molecule tyrosine kinase inhibitors (TKI's) erlotinib, gefitinib, and afatinib have been most successful as single agents in the treatment of lung adenocarcinomas that have somatic mutations (such as L858R or deletion in exon 19, i.e. E746-A750) that confer sensitivity to this class of drugs, which occur in 7-20% of patients depending on ethnicity and gender(19). Unfortunately, responses rarely last more than a year because virtually all patients develop resistance to therapy (20). A third-generation irreversible inhibitor, osimertinib (AZD9291), is effective in treating naïve as well as patients who have acquired resistance to first or second generation TKIs (7). However, within a year of treatment with osimertinib, a majority of patients develop another mutation in the EGFR kinase domain (C797S), which is the drug binding site (12, 21, 22). Although several approaches to target osimertinib resistant EGFR have been reported (12, 13, 23), as of now no TKI treatment option exists for these patients with this C797S mutation. Chemotherapy is the only option.

In view of the foregoing, there exists a need for a cancer therapeutic that targets EGFR in a manner other than inhibition of EGFR tyrosine kinase activity. There also exists a need for a therapeutic that treats cancer without drug resistance developing after initial use.

SUMMARY

Provided herein are compounds and methods for modulating EGFR. More particularly, provided are modulators of EGFR and the uses of such modulators in treating or preventing diseases or disorders associated with aberrant EGFR activity, e.g., cancer.

In one aspect, the disclosure provides compounds, or pharmaceutically acceptable salts thereof, of Formula I:

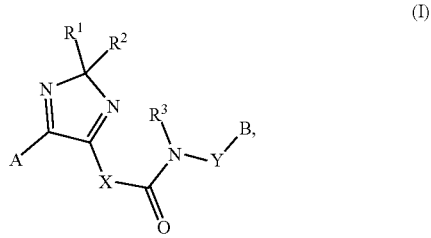

(I)

wherein X is O—$C_{0-6}$alkylene, S—$C_{0-6}$alkylene, or $NR^3$—$C_{0-6}$alkylene, and said alkylene is X is O—$C_{0-6}$alkylene, S—$C_{0-6}$alkylene, or $NR^3$—$C_{0-6}$alkylene, and said alkylene is optionally substituted with 1-3 groups independently selected from halo, $N(R^3)_2$, and $OR^3$; Y is $C_{0-6}$alkylene, and said alkylene is optionally substituted with 1-3 groups independently selected from halo, $N(R^3)_2$, and $OR^3$; A is $C_{6-10}$ aryl or 5-10 membered heteroaryl having 1-4 heteroatoms selected from N, O, and S, and said aryl or heteroaryl is optionally substituted with 1 to 3 $R^4$; B is $C_{6-10}$ aryl, 5-10 membered heteroaryl having 1-4 heteroatoms selected from N, O, and S, 3-8 membered cycloalkyl ring, or 3-12 membered heterocycloalkyl having 1-3 ring heteroatoms selected from O, S, and N, and said aryl, heteroaryl, cycloalkyl, or heterocycloalkyl is optionally substituted with 1 to 3 $R^5$; $R^1$ and $R^2$ are each independently $C_{1-6}$ alkyl, or $R^1$ and $R^2$ together with the carbon atom to which they are attached form a 4-8 membered cycloalkyl or heterocycloalkyl ring, wherein the heterocycloalkyl ring has 1 or 2 ring heteroatoms selected from O, S, and N, and wherein said cycloalkyl ring or heterocycloalkyl ring is optionally substituted with 1-2 $R^6$; each $R^3$ is independently H or $C_{1-8}$ alkyl; each $R^4$ and $R^5$ is independently $C_{1-6}$ alkyl, $C_{1-8}$ haloalkyl, halo, or $C_{1-8}$ alkoxy; and $R^6$ is $C_{1-6}$ alkyl, $C_{1-8}$ haloalkyl, (C=O)$R^3$, (C=)$OR^3$, $CON(R^3)_2$, $C_{0-3}$alkylene-$C_{3-8}$cycloalkyl, $C_{0-3}$alkylene-$C_{8-10}$aryl, or $C_{0-3}$alkylene-(5-10 membered heteroaryl having 1-4 heteroatoms selected from N, O, and S), wherein the aryl or heteroaryl is optionally substituted with 1 to 3 $R^5$.

Further provided herein are methods of using the compounds disclosed to modulate EGFR. Other aspects of the disclosure include methods of using the compounds disclosed to inhibit EGFR dimerization, and methods of using the compounds disclosed to induce EGFR degradation.

Other aspects of the disclosure include a compound as disclosed herein for use in the preparation of a medicament for treating or preventing a disease or disorder associated with aberrant EGFR activity in a subject, and the use of a compound as disclosed herein in a method of treating or preventing a disease or disorder associated with aberrant EGFR activity in a subject.

DETAILED DESCRIPTION

Figure 1:
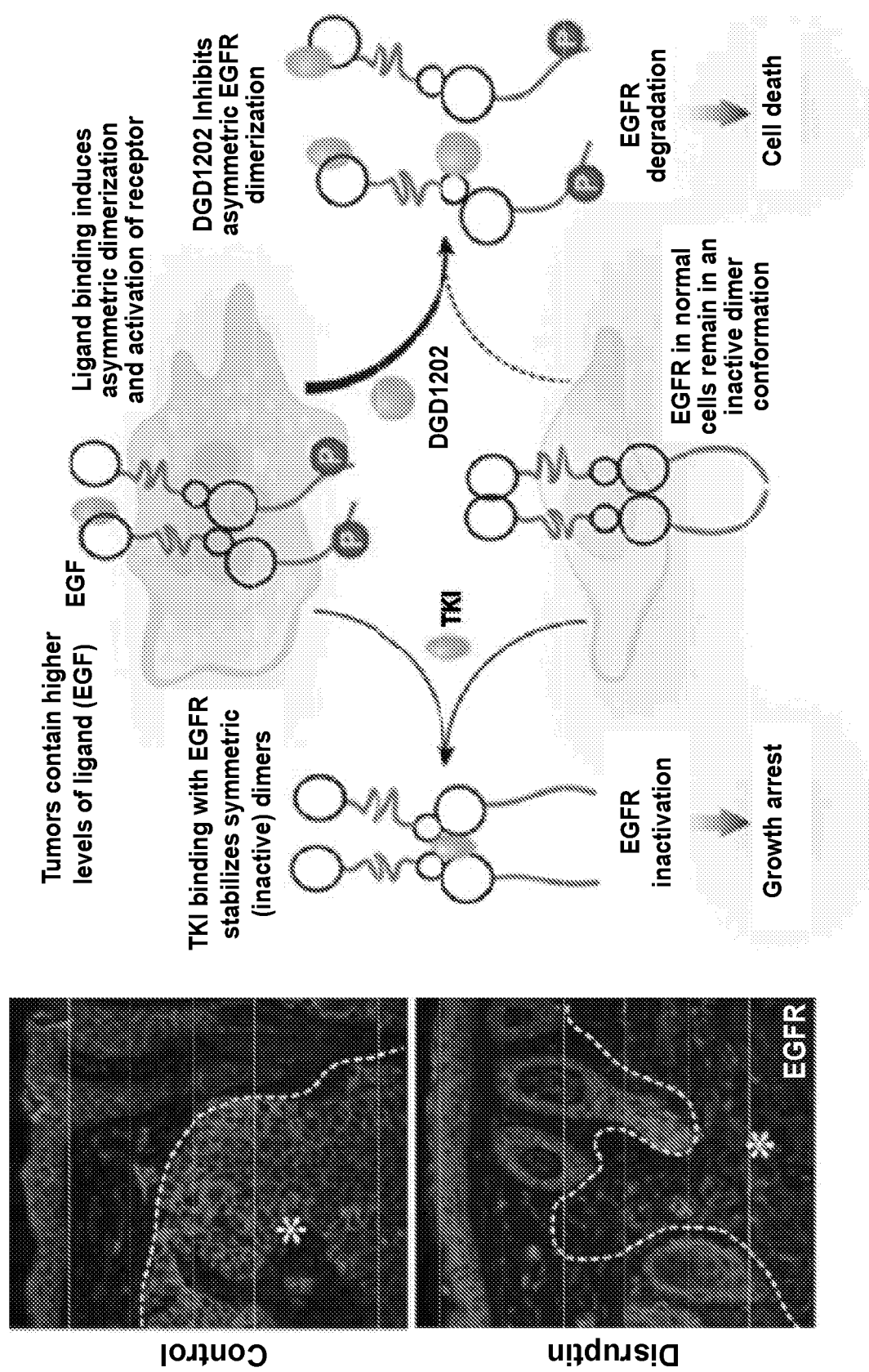
FIG. 1 shows (left) treatment with a small peptide that inhibits EGFR dimerization affected tumor (marked with *) specific EGFR more compared to adjacent normal tissue; and (right) a schematic for degradation of EGFR. EGFR is shown by an extracellular domain connected by a transmembrane portion to a bilobular kinase domain (small blob=n-lobe, large blob=c-lobe) and a flexible C-terminal tail. EGF binding promotes active (asymmetric) dimer formation between extracellular domains and/or between n- and c-lobes of two monomers. EGFR in such a conformation remains stable and induces phosphorylation of the C-terminal tail, which promotes tumor progression Tyrosine kinase inhibitors (e.g. osimertinib), inhibit ATP recruitment and promote inactive (symmetric) dimerization between n-lobes of two monomers. EGFR in this conformation remains in kinase-inactive conformation, but protein stability is maintained. Inactivation of EGFR activity correlates with tumor growth inhibition. The loop between the αC-helix and the β4-sheets of the c-lobe and h-helix of the n-lobe of EGFR participate in EGF-induced active dimer formation. This model assumes that Disruptin or Compound 8C binds in this pocket and interferes with EGF-induced active dimer formation. The ligand and Compound 8C bound-EGFR monomer degrades rapidly. Loss of EGFR protein correlates with cell-death. The thickness of arrow shows the effect of Compound 8C in tumor vs. normal cells.

Although inhibition of the kinase activities of oncogenic proteins using small molecules and antibodies has been a mainstay of anticancer drug development efforts, resulting in several FDA-approved cancer therapies, the clinical effectiveness of kinase-targeted agents has been inconsistent (22, 24). EGFR has been shown to exhibit scaffold functions in addition to its tyrosine kinase activity (24-36). This is demonstrated by either expressing a kinase-dead (KD) mutant of EGFR (e.g. K745A, V741G, and Y740F) or by expressing ErbB3 (which has no kinase activity) in Ba/F3 cells that do not express these receptors (37-39). Expression of these kinase-defective mutants promotes cell survival, indicating that these receptors can still transmit a survival signal perhaps by forming dimers, suggesting that EGFR has functions beyond kinase activity (39).

EGFR dimers are known to be relatively stable when compared to the monomers (40). Dimers are capable of generating downstream mitogenic signaling (41). Without being bound by theory, it is hypothesized that blocking EGFR dimerization would accelerate degradation of EGFR, and that this approach would be effective against tumors that are driven by TKI resistant EGFR (14, 24, 27). Briefly, it was demonstrated that EGF bound EGFR (that is phosphorylated-EGFR, prevalent in most tumors) protein stability is regulated by formation of dimers via a segment within the kinase domain of EGFR that lies between αC helix and β4 sheets of the c-lobe and h-helix of the n-lobe of the EGFR kinase domain (15, 42). EGFR protein stability in normal cells is not primarily regulated by this dimer interface because, in the absence of EGF, EGFR does not form an asymmetric dimer (43). This difference between tumor and normal cells provides a new targetable protein-protein interaction.

To test this idea, over a dozen peptides that mimic this binding surface were generated. The most effective peptide, containing the six amino acids from the αC-β4 loop of the EGFR, was named Disruptin(17). Disruptin is capable of inhibiting EGF-induced dimerization of EGFR. This peptide binds directly to EGFR, and this binding is not affected significantly with repeated HEPES washes compared to a control (scrambled) peptide. Although Disruptin is effective in a tyrosine kinase inhibitor (TKI) resistant lung xenograft model (14), delivery of peptides in humans remains challenging (44).

Provided herein are compounds which modulate EGFR, for example, compounds which block EGFR dimerization, induce EGFR degradation, and kill EGFR driven cells. These compounds are useful in the prevention or treatment of a variety of diseases and disorders, for example, in the treatment of cancer.

As such, provided herein are compounds, or pharmaceutically acceptable salts thereof, having the structure of Formula I:

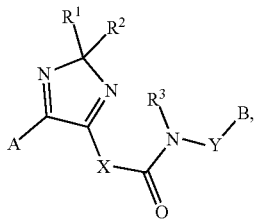

(I)

wherein

X is O—$C_{0-6}$alkylene, S—$C_{0-6}$alkylene, or $NR^3$—$C_{0-6}$ alkylene, and said alkylene is optionally substituted with 1-3 groups independently selected from halo, $N(R^3)_2$, and $OR^3$;

Y is $C_{0-6}$alkylene, and said alkylene is optionally substituted with 1-3 groups independently selected from halo, $N(R^3)_2$, and $OR^3$;

A is $C_{6-10}$ aryl or 5-10 membered heteroaryl having 1-4 heteroatoms selected from N, O, and S, and said aryl or heteroaryl is optionally substituted with 1 to 3 $R^4$;

B is $C_{6-10}$ aryl, 5-10 membered heteroaryl having 1-4 heteroatoms selected from N, O, and S, 3-8 membered cycloalkyl ring, or 3-12 membered heterocycloalkyl having 1-3 ring heteroatoms selected from O, S, and N, and said aryl, heteroaryl, cycloalkyl, or heterocycloalkyl is optionally substituted with 1 to 3 $R^5$;

$R^1$ and $R^2$ are each independently $C_{1-6}$ alkyl, or $R^1$ and $R^2$ together with the carbon atom to which they are attached form a 4-8 membered cycloalkyl or heterocycloalkyl ring, wherein the heterocycloalkyl ring has 1 or 2 ring heteroatoms selected from O, S, and N, and wherein said cycloalkyl ring or heterocycloalkyl ring is optionally substituted with 1-2 $R^6$;

each $R^3$ is independently H or $C_{1-6}$ alkyl;

each $R^4$ and $R^5$ is independently $C_{1-6}$ alkyl, $C_{1-6}$ haloalkyl, halo, or $C_{1-6}$ alkoxy; and $R^6$ is $C_{1-6}$ alkyl, $C_{1-6}$ haloalkyl, (C=O)$R^3$, (C=O)O$R^3$, CON($R^3$)$_2$, $C_{0-3}$alkylene-$C_{3-8}$scrloalkyl, $C_{0-3}$alkylene-$C_{6-10}$ aryl, or $C_{0-3}$alkylene-(5-10 membered heteroaryl having 1-4 heteroatoms selected from N, O, and S), wherein the aryl or heteroaryl is optionally substituted with 1 to 3 $R^5$.

In various embodiments, $R^1$ and $R^2$ are each independently $C_{1-6}$ alkyl. In some embodiments, $R^1$ and $R^2$ are each methyl.

In various embodiments, $R^1$ and $R^2$ together with the carbon atom to which they are attached form a 4-8 membered cycloalkyl or heterocycloalkyl ring. In some embodiments, $R^1$ and $R^2$ together with the carbon atom to which they are attached form a 5 or 6 membered cycloalkyl or heterocycloalkyl ring. In some embodiments, $R^1$ and $R^2$ together with the carbon atom to which they are attached form a cyclohexyl ring.

In various embodiments, $R^1$ and $R^2$ together with the carbon atom to which they are attached form a heterocycloalkyl ring having the structure:

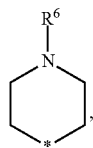

where * indicates the point of attachment to the rest of the compound of Formula I. In some embodiments, $R^6$ is $C_{1-6}$ alkyl, $C_{1-6}$ haloalkyl, (C=O)$R^3$, (C=O)O$R^3$, CON($R^3$)$_2$, $C_{0-3}$alkylene-$C_{3-6}$cycloalkyl, $C_{0-3}$alkylene-$C_{6-10}$aryl, or $C_{0-3}$alkylene-(5-10 membered heteroaryl having 1-4 heteroatoms selected from N, O, and S), wherein the aryl or heteroaryl is optionally substituted with 1 to 3 $R^5$. In some embodiments, $R^6$ is $C_{1-6}$ alkyl, (C=O)$R^3$, (C=O)O$R^3$, or CON($R^3$)$_2$. In some embodiments, $R^6$ is $C_{1-6}$ alkyl. In some embodiments, $R^6$ is methyl, ethyl, propyl, isopropyl, isobutyl, or isopentyl. In some embodiments, $R^6$ is methyl. In some embodiments, $R^6$ is deuterated. In some embodiments, $R^6$ is $C_{1-6}$ haloalkyl. In some embodiments, $R^6$ is 3,3,3-trifluoropropyl. In some embodiments, $R^6$ is $C_{0-3}$alkylene-$C_{3-8}$cycloalkyl. In some embodiments, $R^6$ is cyclobutyl, cyclopentyl, or cyclohexyl. In some embodiments, $R^6$ is cyclobutyl or cyclopentyl. In some embodiments, $R^6$ is $C_{0-3}$alkylene-$C_{6-10}$aryl. In some embodiments, $R^6$ is benzyl. In some embodiments, $R^6$ is $C_{0-3}$alkylene-(5-10 membered heteroaryl having 1-4 heteroatoms selected from N, O, and S), wherein the heteroaryl is optionally substituted with 1 to 3 $R^5$. In some embodiments, $R^6$ is $C_1$alkylene-(5-10 membered heteroaryl having 1-4 heteroatoms selected from N, O, and S), wherein the heteroaryl is optionally substituted with 1 to 3 $R^5$. In some embodiments, $R^6$ is $C_{0-3}$alkylene-(5-10 membered heteroaryl having 1-4 heteroatoms selected from N, O, and S), wherein the heteroaryl is substituted with 1 to 3 $R^5$. In some embodiments, $R^6$ is $C_{0-3}$alkylene-(5-10 membered heteroaryl having 1-4 heteroatoms selected from N, O, and S), wherein the heteroaryl is unsubstituted. In some embodiments, $R^6$ is

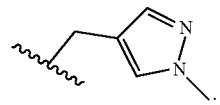 [SMILES: *Cc1cnn(C)c1]

In various embodiments, A is $C_{6-10}$ aryl. In some embodiments, A is phenyl.

In various embodiments, B is $C_{6-10}$ aryl. In some embodiments, B is phenyl. In various embodiments, B is 5-10 membered heteroaryl having 1-4 heteroatoms selected from N, O, and S. In some embodiments, B is pyridinyl. In some embodiments, B is quinolinyl. In various embodiments, B is 3-8 membered cycloalkyl. In some embodiments, B is 5 or 6 membered cycloalkyl. In various embodiments, B is 3-12 membered heterocycloalkyl having 1-3 ring heteroatoms selected from O, S, and N.

In some embodiments, A is substituted with one $R^4$. In some embodiments, A has the structure:

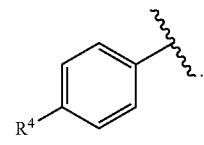

In some embodiments, A is substituted with two $R^4$. In some embodiments, at least one $R^4$ is $C_{1-6}$ alkyl. In some embodiments, at least one $R^4$ is methyl. In some embodiments, at least one $R^4$ is halo. In some embodiments, $R^4$ is bromo. In some embodiments, at least one $R^4$ is $C_{1-6}$ alkoxy. In some embodiments, at least one $R^4$ is methoxy.

In some embodiments, B is substituted with one $R^5$. In some embodiments, B is substituted with two $R^5$. In some embodiments, B has the structure

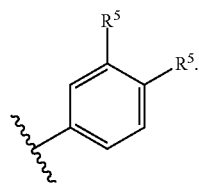

In some embodiments, at least one $R^5$ is halo. In some embodiments, at least one $R^5$ is fluoro or chloro. In some embodiments, one $R^5$ is fluoro and the other $R^5$ is chloro. In some embodiments, at least one $R^5$ is $C_{1-6}$ alkoxy. In some embodiments, at least one $R^5$ is methoxy. In some embodiments, one $R^5$ is halo and the other $R^5$ is $C_{1-6}$ alkoxy. In some embodiments, one $R^5$ is chloro and the other $R^5$ is methoxy.

In some embodiments, each $R^4$ and $R^5$ is independently $C_{1-6}$ alkyl, halo, or $C_{1-6}$ alkoxy. In some embodiments, $R^6$ is $C_{1-6}$ alkyl, (C=O)$R^3$, (C=O)O$R^3$, or CON($R^3$)$_2$.

In various embodiments, X is O- $C_{0-6}$alkylene or S-$C_{0-6}$alkylene. In some embodiments, X is S- $C_{0-6}$alkylene. In some embodiments, X is O, S, O—CH$_2$—, or S—CH$_2$-. In various embodiments, Y is $C_{0-2}$alkylene. In some embodiments, Y is null or CH$_2$. In some embodiments, X is NR$^3$—CH$_2$, O—CH$_2$—, or S—CH$_2$—, and Y is null. In some embodiments, X is NR$^3$—CH$_2$, O—CH$_2$—, or S—CH$_2$—, and Y is CH$_2$. In some embodiments, R$^3$ is H.

Specific compounds contemplated include those listed in Table 1, Table 2, or a pharmaceutically acceptable salt thereof:

TABLE 1

| ID # | STRUCTURE |
|---|---|
| 13 | 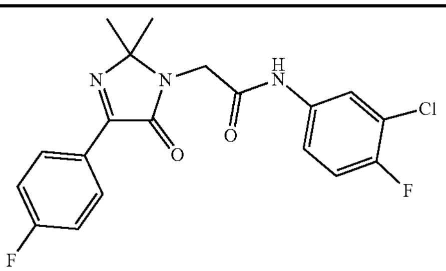 |
| 14 | 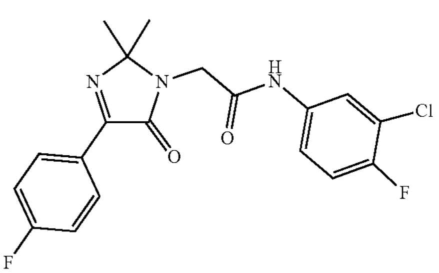 [SMILES: CC1(C)N=C(c2ccc(F)cc2)C(=O)N1CC(=O)Nc1ccc(F)c(Cl)c1] |

TABLE 1-continued

| ID # | STRUCTURE |
|---|---|
| 15 | 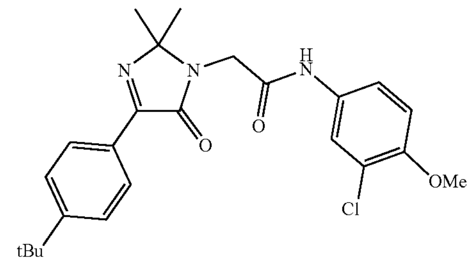 [SMILES: COc1ccc(NC(=O)CN2C(=O)C(c3ccc(C(C)(C)C)cc3)=NC2(C)C)cc1Cl] |
| 16 | 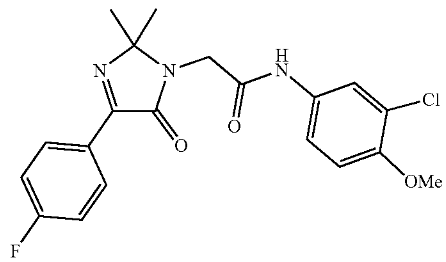 [SMILES: COc1ccc(NC(=O)CN2C(=O)C(c3ccc(F)cc3)=NC2(C)C)cc1Cl] |
| 17 | 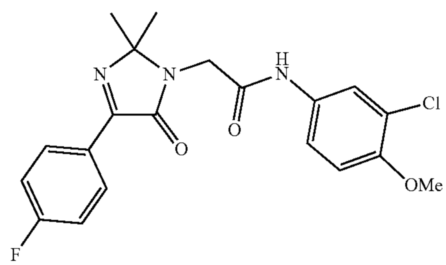 [SMILES: COc1ccc(NC(=O)CN2C(=O)C(c3ccc(F)cc3)=NC2(C)C)cc1Cl] |
| 18 | 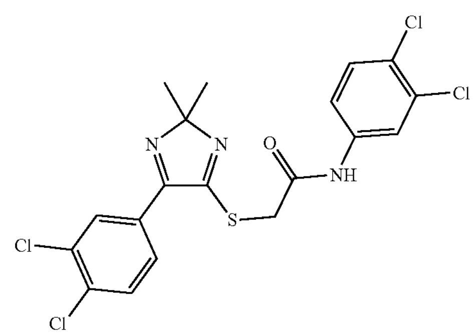 [SMILES: CC1(C)N=C(SCC(=O)Nc2ccc(Cl)c(Cl)c2)C(c2ccc(Cl)c(Cl)c2)=N1] |
| 19 | 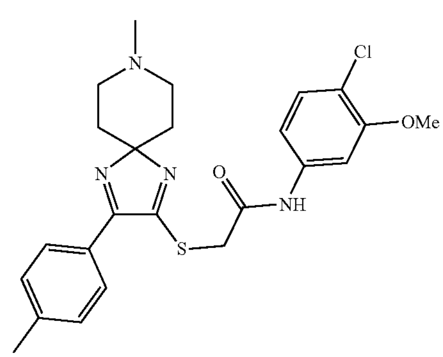 [SMILES: COc1cc(NC(=O)CSC2=NC3(CCN(C)CC3)N=C2c2ccc(C)cc2)ccc1Cl] |

TABLE 1-continued

| ID # | STRUCTURE |
|---|---|
| 20 | (structure) |
| 21 | (structure) |
| 22 | (structure) |
| 23 | (structure) |
| 24 | (structure) |
| 25 | (structure) |
| 26 | (structure) |
| 27 | (structure) |

TABLE 1-continued
| ID # | STRUCTURE |
|---|---|
| 28 | 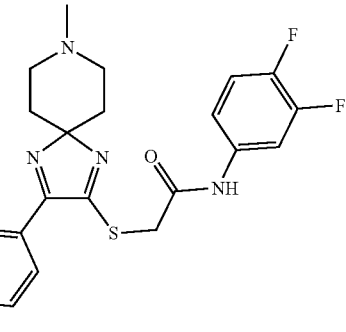 |
| 29 | 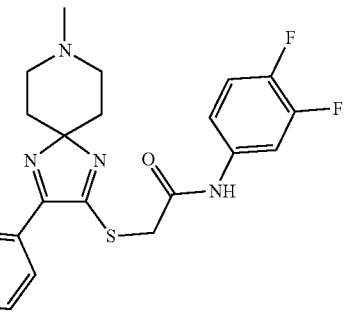 |
| 8A | 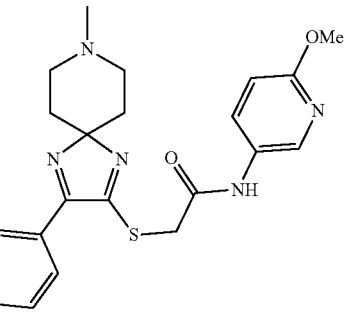 |
| 8B | 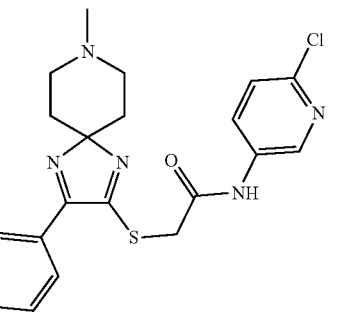 |
| 8C | 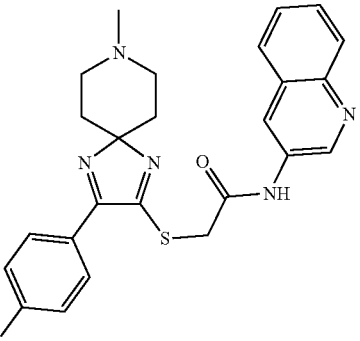 |
| 8D | 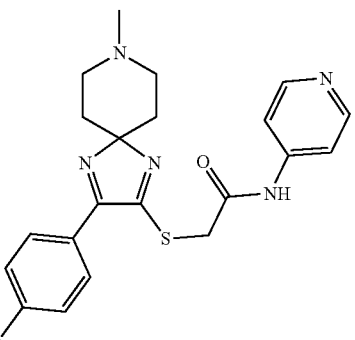 |
| 8E | 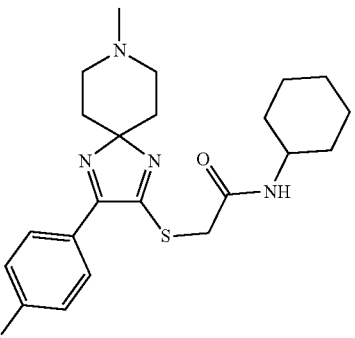 |
| 8F | 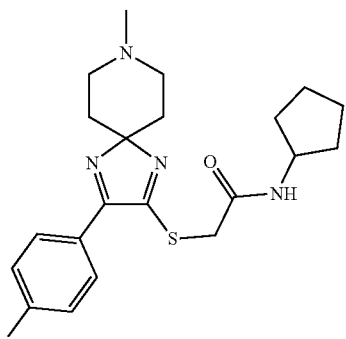 |

TABLE 1-continued
| ID # | STRUCTURE |
|---|---|
| 8G | 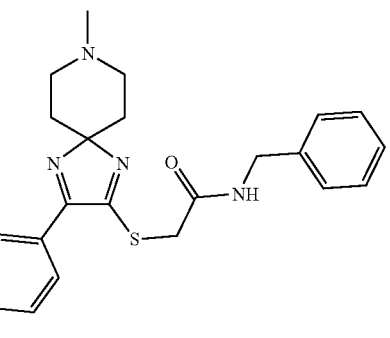 |
| 10 | 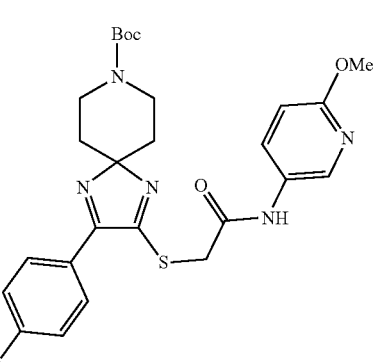 |
| 11 | 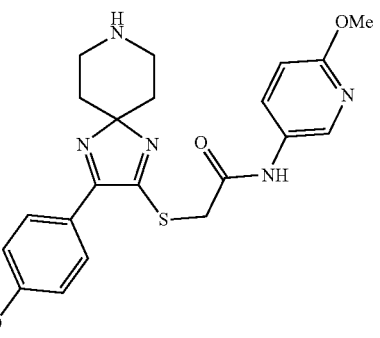 |
| 12 | 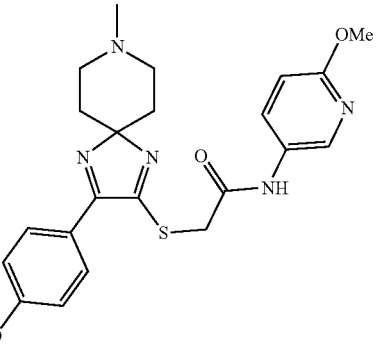 |
TABLE 1-continued
| ID # | STRUCTURE |
|---|---|
| 30 | 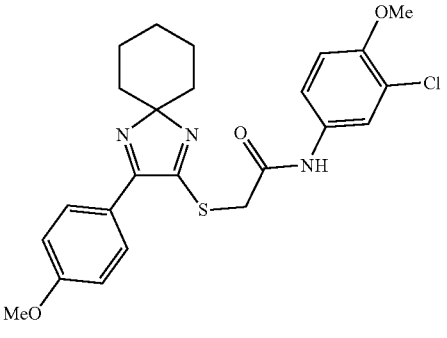 [SMILES: COc1ccc(C2=NC3(CCCCC3)N=C2SCC(=O)Nc2ccc(OC)c(Cl)c2)cc1] |
| 31 | 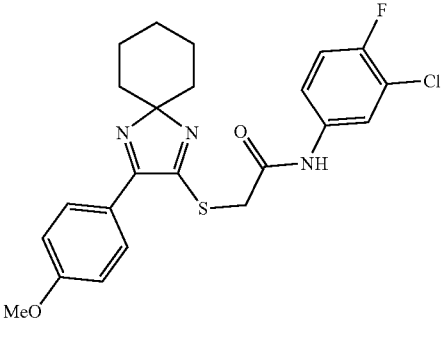 [SMILES: COc1ccc(C2=NC3(CCCCC3)N=C2SCC(=O)Nc2ccc(F)c(Cl)c2)cc1] |
| 32 | 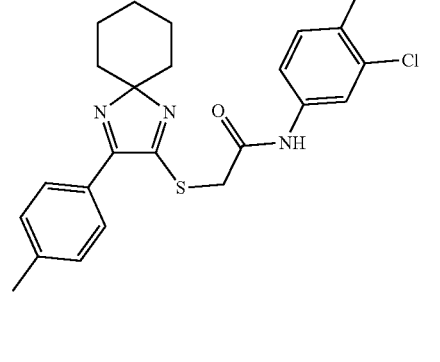 |
| 3 | 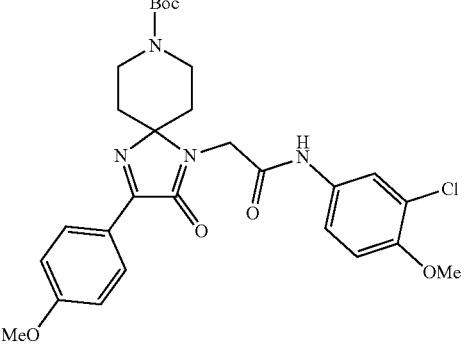 |

TABLE 1-continued

| ID # | STRUCTURE |
|---|---|
| 4 | (structure) |
| 5 | (structure) |

TABLE 2

| ID # | Structure |
|---|---|
| 33a | (structure) |
| 33b | (structure) |
| 33c | (structure) |
| 33d | (structure) |

TABLE 2-continued
| ID # | Structure |
|---|---|
| 33e | 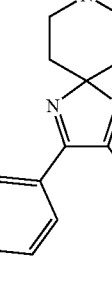 |
| 33f | 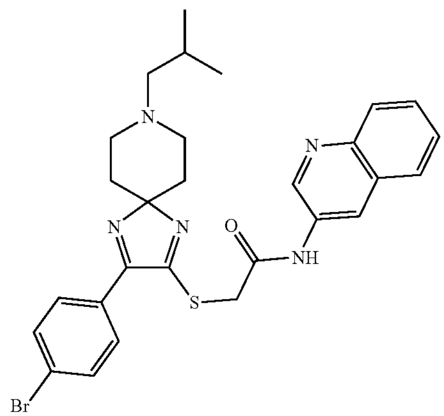 [SMILES: CC(C)CN1CCC2(CC1)N=C(SCC(=O)Nc1cnc3ccccc3c1)C(c1ccc(Br)cc1)=N2] |
| 33g | 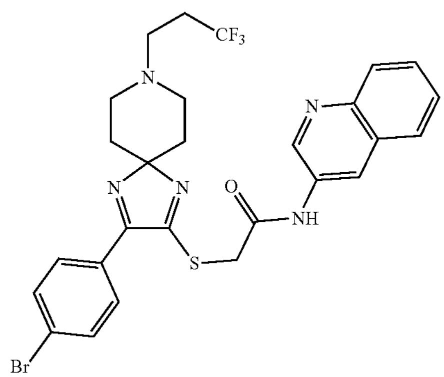 [SMILES: O=C(CSC1=NC2(CCN(CCC(F)(F)F)CC2)N=C1c1ccc(Br)cc1)Nc1cnc2ccccc2c1] |
| 33h | 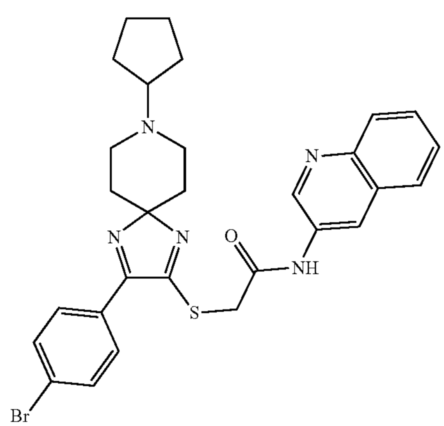 [SMILES: O=C(CSC1=NC2(CCN(C3CCCC3)CC2)N=C1c1ccc(Br)cc1)Nc1cnc2ccccc2c1] |
| 33i | 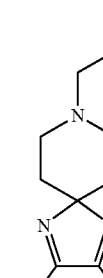 |
| 33j | |
| 33k | |

TABLE 2-continued
| ID # | Structure |
|---|---|
| 33l | 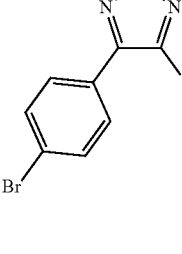 |
| 34a | 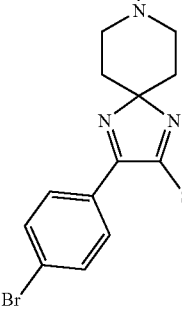 |
| 34b | 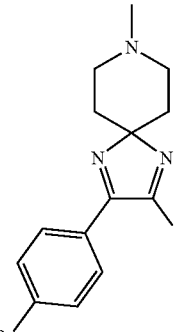 |
| 34c | 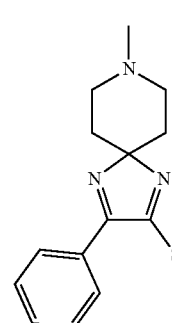 |
| 34d | 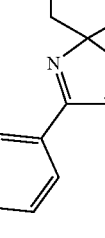 |
| 34e | 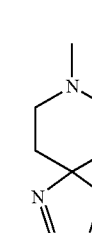 |
| 34f | 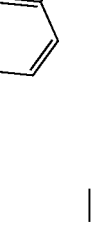 |
| 35a | 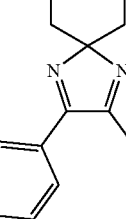 |

TABLE 2-continued

| ID # | Structure |
|---|---|
| 35b | (structure) |
| 35c | (structure) |
| 35d | (structure) |
| 35e | (structure) |
| 35f | (structure) |
| 35g | (structure) |
| 35h | (structure) |
| 35i | (structure) |

In some cases, the compound is a compound listed in Table 1, or salt thereof.

Compound 8C showed significant improvement in pharmacological properties as well as biological activity (microsomal half-life over 46 minutes, sub-micromolar $IC_{50}$ in the clonogenic cellular assay). Compound 8C inhibits EGF-induced EGFR dimerization, directly binds to purified EGFR, and is selectively active in EGFR-driven osimertinib resistant cell lines and in xenograft models.

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (e.g., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

The term "alkylene" used herein refers to an alkyl group having a substituent. For example, the term "alkylenehalo" refers to an alkyl group substituted with a halo group. For example, an alkylene group can be —$CH_2CH_2$— or —$CH_2$—. The term $C_n$ means the alkylene group has "n" carbon atoms. For example, $C_{1-6}$alkylene refers to an alkylene group having a number of carbon atoms encompassing the entire range, as well as all subgroups, as previously described for "alkyl" groups. Unless otherwise indicated, an alkylene group can be an unsubstituted alkylene group or a substituted alkylene group.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_6$-$C_8$ cycloalkyl refers to cycloalkyl groups having a number of carbon atoms encompassing the entire range (e.g., 6 to 8 carbon atoms), as well as all subgroups (e.g., 6-7, 7-8, 6, 7, and 8carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group. When a cycloalkyl group is fused to another cycloalkyl group, then each of the cycloalkyl groups can contain three to eight carbon atoms unless specified otherwise. Unless otherwise indicated, a cycloalkyl group can be unsubstituted or substituted.

As used herein, the term "heterocycloalkyl" is defined similarly as cycloalkyl, except the ring contains one to three heteroatoms independently selected from oxygen, nitrogen, and sulfur. In particular, the term "heterocycloalkyl" refers to a ring containing a total of three to twelve atoms (e.g., 3-8, 5-8, 3-6, 3, 4, 5, 6, 7, 8, 9, 10, 11, or 12), of which 1, 2, or 3 of the ring atoms are heteroatoms independently selected from the group consisting of oxygen, nitrogen, and sulfur, and the remaining atoms in the ring are carbon atoms. Nonlimiting examples of heterocycloalkyl groups include piperdine, pyrazolidine, tetrahydrofuran, tetrahydropyran, dihydrofuran, morpholine, and the like.

Cycloalkyl and heterocycloalkyl groups can be saturated or partially unsaturated ring systems optionally substituted with, for example, one to three groups, independently selected alkyl, alkyleneOH, $C(O)NH_2$, $NH_2$, oxo (O), aryl, alkylenehalo, halo, and OH. Heterocycloalkyl groups optionally can be further N-substituted with alkyl (e.g., methyl or ethyl), alkylene-OH, alkylenearyl, and alkyleneheteroaryl. The heterocycloalkyl groups described herein can be isolated or fused to another heterocycloalkyl group, a cycloalkyl group, an aryl group, and/or a heteroaryl group. When a heterocycloalkyl group is fused to another heterocycloalkyl group, then each of the heterocycloalkyl groups can contain three to twelve total ring atoms, and one to three heteroatoms. Unless otherwise indicated, a heterocycloalkyl group can be unsubstituted or substituted.

As used herein, the term "aryl" refers to a monocyclic or bicyclic aromatic group, having 6 to 10 ring atoms. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Aryl groups can be isolated (e.g., phenyl) or fused to another aryl group (e.g., naphthyl, anthracenyl), a cycloalkyl group (e.g. tetraydronaphthyl), a heterocycloalkyl group, and/or a heteroaryl group As used herein, the term "heteroaryl" refers to a monocyclic or bicyclic aromatic ring having 5 to 10 total ring atoms, and containing one to four heteroatoms selected from nitrogen, oxygen, and sulfur atom in the aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, pyrrolyl, oxazolyl, triazinyl, triazolyl, isothiazolyl, isoxazolyl, imidazolyl, pyrazinyl, pyrimidinyl, thiazolyl, and thiadiazolyl.

As used herein, the term "alkoxy" or "alkoxyl" as used herein refers to a "-O-alkyl" group. The alkoxy or alkoxyl group can be unsubstituted or substituted.

As used herein, the term "therapeutically effective amount" means an amount of a compound or combination of therapeutically active compounds that ameliorates, attenuates or eliminates one or more symptoms of a particular disease or condition (e.g., cancer), or prevents or delays the onset of one of more symptoms of a particular disease or condition.

As used herein, the terms "patient" and "subject" may be used interchangeably and mean animals, such as dogs, cats, cows, horses, and sheep (e.g., non-human animals) and humans. Particular patients or subjects are mammals (e.g., humans).

As used herein, the term "pharmaceutically acceptable" means that the referenced substance, such as a compound of the present disclosure, or a formulation containing the compound, or a particular excipient, are safe and suitable for administration to a patient or subject. The term "pharmaceutically acceptable excipient" refers to a medium that does not interfere with the effectiveness of the biological activity of the active ingredient(s) and is not toxic to the host to which it is administered.

The compounds disclosed herein can be as a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences,* 1977, 66, 1-19, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

Synthesis of Compounds of the Disclosure

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. The synthesis of the compounds disclosed herein can be achieved by generally following the synthetic schemes as described in the Examples section, with modification for specific desired substituents.

Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5th edition, John Wiley & Sons: New York, 2001; and Greene, T. W., Wuts, P. G. M., Protective Groups in Organic Synthesis, 3rd edition, John Wiley & Sons: New York, 1999, are useful and recognized reference textbooks of organic synthesis known to those in the art. The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt thereof.

In general, compounds of Formula (I) can be synthesized according to Scheme 1.

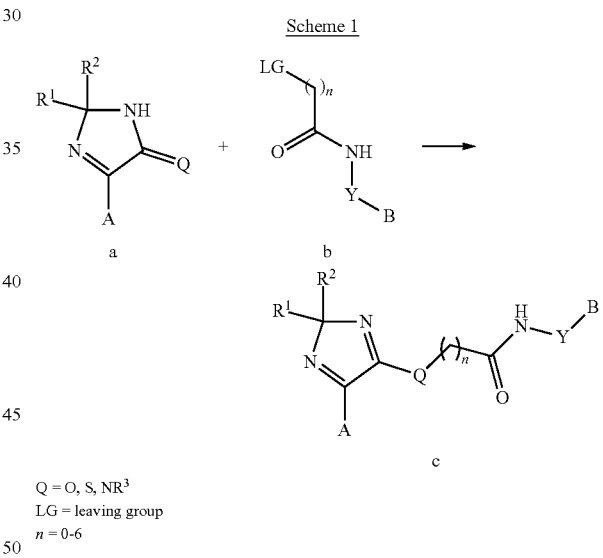

Scheme 1

$Q = O, S, NR^3$
LG = leaving group
$n = 0\text{-}6$

Compounds having structure c can be synthesized using the procedure shown in Scheme 1. Reaction of a substituted 2,5-dihydroimidazole derivative a with an amide compound b in an appropriate solvent e.g., acetonitrile, produces compounds as described herein, i.e., compounds of Formula (I) having structure c. The amide compound b comprises an appropriate leaving group LG chosen based on the nature of group Q, e.g., a halogen or tosylate. Appropriate further derivatization reactions of compounds having structure c can be selected based on the nature of substituents $R^1$, $R^2$, A, Y, and B.

The coupling of compounds a and b can be catalyzed by appropriate reagents selected based on the precise nature of compounds a and b. For example, when the LG of compound b is a halogen (e.g., when LG is chloro), the coupling of compounds a and b can be catalyzed by a base e.g., sodium carbonate or potassium carbonate. Occasionally, the coupling reaction may not require a catalyst.

Occasionally, before coupling with a compound having structure b, a compound a having Q selected from O, S, and $NR^3$ can be transformed into a compound having Q selected from a different member of the group consisting of O, S, and $NR^3$ by treatment with an appropriate reagent. For example, a compound having a structure a with Q=O can be transformed into a compound having a structure a with Q=S by treatment with a thiation reagent, e.g., Lawesson's reagent or phosphorus pentasulfide. Such a compound can then be coupled with a compound having structure b to produce a compound described herein, i.e., a compound of Formula (I) having structure c.

Compounds a and b can be purchased commercially or prepared by a variety of methods from commercially-available starting materials. For example, amide compounds having structure b can be prepared by the reaction of e.g. an acyl chloride with an amine.

Further derivatization reactions to transform compounds having structure c into other compounds disclosed herein can be selected based on the nature of the substituents $R^1$, $R^2$, A, Y, and B in compound c and the functionality desired in the derivative compound. For example, $R^1$ and $R^2$ together with the carbon atom to which they are attached can form a heterocycling ring, e.g. a piperidine ring, which can be further derivatized by methods known in the art (e.g., methylation, addition of protecting groups, etc.) to form a variety of other compounds of Formula (I) described herein.

Pharmaceutical Formulations, Dosing, and Routes of Administration

Further provided are pharmaceutical formulations comprising a compound as described herein (e.g., compounds of Formula I, or pharmaceutically acceptable saltsthereof) and a pharmaceutically acceptable excipient.

The compounds described herein can be administered to a subject in a therapeutically effective amount (e.g., in an amount sufficient to prevent or relieve the symptoms of a disease or disorder associated with aberrant EGFR). The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

A particular administration regimen for a particular subject will depend, in part, upon the compound, the amount of compound administered, the route of administration, and the cause and extent of any side effects. The amount of compound administered to a subject (e.g., a mammal, such as a human) in accordance with the disclosure should be sufficient to effect the desired response over a reasonable time frame. Dosage typically depends upon the route, timing, and frequency of administration. Accordingly, the clinician titers the dosage and modifies the route of administration to obtain the optimal therapeutic effect, and conventional range-finding techniques are known to those of ordinary skill in the art.

Purely by way of illustration, the method comprises administering, e.g., from about 0.1 mg/kg up to about 100 mg/kg of a compound as disclosed herein, depending on the factors mentioned above. In other embodiments, the dosage ranges from 1 mg/kg up to about 100 mg/kg; or 5 mg/kg up to about 100 mg/kg; or 10 mg/kg up to about 100 mg/kg. Some conditions require prolonged treatment, which may or may not entail administering lower doses of compound over multiple administrations. If desired, a dose of the compound is administered as two, three, four, five, six or more sub-doses administered separately at appropriate intervals throughout the day, optionally, in unit dosage forms. The treatment period will depend on the particular condition, and may last one day to several months.

Suitable methods of administering a physiologically-acceptable composition, such as a pharmaceutical composition comprising the compounds disclosed herein (e.g., compounds of Formula (I)), are well known in the art. Although more than one route can be used to administer a compound, a particular route can provide a more immediate and more effective reaction than another route. Depending on the circumstances, a pharmaceutical composition comprising the compound is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection, or by one of the following means: intravenous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal. The compound can be administered by sustained release systems, or by implantation devices.

To facilitate administration, the compound is, in various aspects, formulated into a physiologically-acceptable composition comprising a carrier (e.g., vehicle, adjuvant, or diluent). The particular carrier employed is limited only by chemico-physical considerations, such as solubility and lack of reactivity with the compound, and by the route of administration. Physiologically-acceptable carriers are well known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers, eds., pages 238-250 (1982), and ASHP Handbook on Injectable Drugs, Toissel, 4th ed., pages 622-630 (1986)). A pharmaceutical composition comprising the compound is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents.

Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of Use

The compounds described herein can modulate EGFR. In some embodiments, the compounds inhibit EGFR dimerization. In various embodiments, the compounds induce EGFR degradation.

Although EGFR has clearly been identified as an oncogene and an important molecular target in cancer, there is still a great need and opportunity for an improved approach to modulate the activity of this oncogene. Using a cell penetrating peptide that blocks dimerization (Disruptin) or siRNA, it has been shown that EGFR degradation has a profound effect on cell survival, even in TKI resistant cells (14, 23, 25, 26). Without being bound by theory, it is hypothesized that the degradation of active-EGFR (abundant in tumors) by a small molecule that inhibits dimerization, is selective, since most normal cells do not express high levels of EGF/EGFR and therefore form symmetric dimers which are not expected to be affected by Compound 8C. This approach is effective even in TKI-resistant tumor cells because the dimer interface in the TKI resistant tumors remains intact (see FIGS. 1A and 1B). The approach described here is unique compared to currently approved therapies. By degrading the EGFR protein rather than simply inhibiting its kinase activity, a broad spectrum of activities has been demonstrated in preclinical models while improving the ability to target tumor tissue due to the fact that this agent affects only EGF-bound EGFR, which is abundant in tumor cells compared to normal tissue, thereby, improving the safety profile and the therapeutic window.

The approach of degrading EGFR rather than simply inhibiting its kinase activity overcomes the resistance to osimertinib that invariably develops in patients with non-small cell lung cancer. While the focus of this application is on lung cancers, additional and important clinical opportunities also exist in other cancers that are driven by EGFR, such as head & neck, colorectal, and glioblastoma. Targeted selective degradation of an oncoprotein in tumors therefore represents a novel mechanism beyond inhibition of the kinase activity, and this approach might be applicable to other oncogenic proteins (22, 25, 26, 46).

The compounds disclosed herein are particularly advantageous for the treatment or prevention of diseases or disorders caused by aberrant EGFR activity.

As used herein, "aberrant EGFR activity" refers to activity associated with mutation and overexpression of the epidermal growth factor receptor (EGFR). Such mutation and overexpression is associated with the development of a variety of cancers (Shan et al., Cell 2012, 149(4) 860-870).

Given the importance of the biological roles of EGFR, the compounds of the present disclosures are useful for a number of applications in a variety of settings. For example and most simplistically, the active agents of the present disclosures are useful for inhibiting the dimerization of EGFR in a cell. In this regard, the present disclosures provide a method of inhibiting the dimerization of EGFR in a cell. The method comprises contacting the cell with a compound of the present disclosures, or a pharmaceutically acceptable salt thereof, in an amount effective to inhibit the dimerization. In some aspects, the cell is part of an in vitro or ex vivo cell culture or in vitro or ex vivo tissue sample. In some aspects, the cell is an in vivo cell. In certain embodiments, the method is intended for research purposes, and, in other embodiments, the method is intended for therapeutic purposes.

Inhibition of EGFR dimerization leads to an increase in EGFR degradation. Accordingly, the present disclosures further provides a method of increasing EGFR degradation in a cell. The method comprises contacting the cell with a compound of the present disclosures, or a pharmaceutically acceptable salt thereof, in an amount effective to increase the degradation. In some aspects, the cell is part of an in vitro or ex vivo cell culture or in vitro or ex vivo tissue sample. In some aspects, the cell is an in vivo cell. In certain embodiments, the method is intended for research purposes, and, in other embodiments, the method is intended for therapeutic purposes.

As shown herein, a compound that inhibits dimerization of EGFR increases tumor cell death. Thus, the present disclosures provides a method of increasing tumor cell death in a subject. The method comprises administering to the subject a compound of the present disclosure, or a pharmaceutically acceptable salt thereof, in an amount effective to increase tumor cell death.

In accordance with the foregoing, the present disclosures further provides a method of treating a cancer in a subject. The method comprises administering to the subject a compound of the present disclosures, or a pharmaceutically acceptable salt thereof, in an amount effective to treat the cancer in the subject.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating cancer of the present disclosures can provide any amount or any level of treatment of cancer. Furthermore, the treatment provided by the method of the present disclosures may include treatment of one or more conditions or symptoms of the cancer, being treated. Also, the treatment provided by the methods of the present disclosures may encompass slowing the progression of the cancer. For example, the methods can treat cancer by virtue of reducing tumor or cancer growth, reducing metastasis of tumor cells, increasing cell death of tumor or cancer cells, and the like.

The cancer treatable by the methods disclosed herein may be any cancer, e.g., any malignant growth or tumor caused by abnormal and uncontrolled cell division that may spread to other parts of the body through the lymphatic system or the blood stream.. In some embodiments, the cancer is a cancer in which an EGFR is expressed by the cells of the cancer. In some aspects, the cancer is a cancer in which an EGFR protein is over-expressed, the gene encoding EGFR is amplified, and/or an EGFR mutant protein (e.g., truncated EGFR, point-mutated EGFR) is expressed.

The cancer in some aspects is one selected from the group consisting of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, leukemia (e.g., chronic lymphocytic leukemia), chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. In particular aspects, the cancer is selected from the group consisting of: head and neck, ovarian, cervical, bladder and oesophageal cancers, pancreatic, gastrointestinal cancer, gastric, breast, endometrial and colorectal cancers, hepatocellular carcinoma, glioblastoma, bladder, lung cancer, e.g., non-small cell lung cancer (NSCLC), bronchioloalveolar carcinoma. In particular aspects, the cancer is an osimertinib-resistant cancer. In some cases, the cancer is pancreatic cancer, head and neck cancer, melanoma, colon cancer, renal cancer, leukemia, or breast cancer. In some cases, the cancer is melanoma, colon cancer, renal cancer, leukemia, or breast cancer.

Uses of the compounds disclosed herein in the preparation of a medicament for modulating EGFR, or for treating or preventing a disease or disorder associated with aberrant EGFR activity also are provided herein.

The disclosure herein will be understood more readily by reference to the following examples, below.

In view of the many possible embodiments to which the principles of the disclosure may be applied, it should be recognized that the illustrated embodiments are only examples and should not be taken as limiting the scope of the invention.

EXAMPLES

Example 1: General Procedure A:

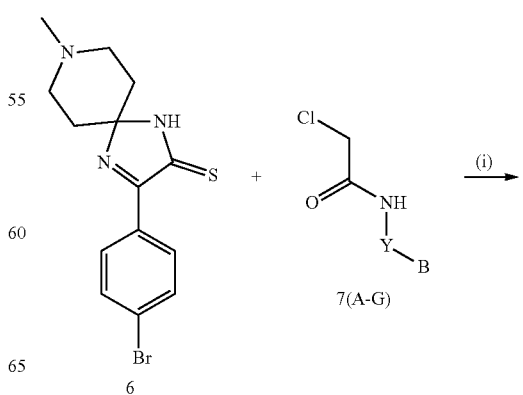

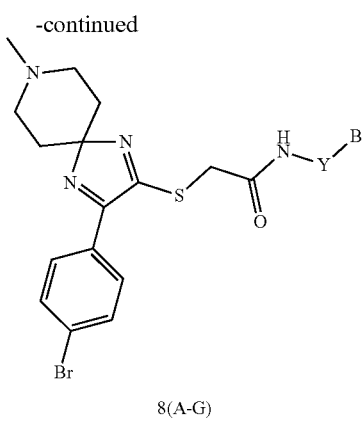

8(A-G)

Reaction conditions: (i) 2M aq. K$_2$CO$_3$, Acetonitrile, 40° C.
7A 2-chloro-N-(6-methoxypyridin-3-yl)acetamide hydrochloride
7B 2-chloro-N-(6-chloropyridin-3-yl)acetamide
7C 2-chloro-N-quinolin-3-yl-acetamide
7D 2-chloro-N-(pyridin-4-yl)acetamide hydrochloride
7E 2-chloro-N-cyclohexyl-acetamide
7F 2-chloro-N-cyclopentylacetamide
7G N-benzyl-2-chloroacetamide To a solution of 3-(4-bromophenyl)-8-methyl-1,4,8-triazaspiro[4.5]dec-3-ene-2-thione 6 in anhydrous acetonitrile was added acetamide 7A-G (1 equiv.). The reaction mixture was warmed to 40° C. Next, 2M aqueous potassium carbonate solution (1 equiv.) was added to the reaction mixture. The reaction was maintained at 40° C. until TLC showed loss of starting materials and new R$_f$ spot (typically 2-6 hours). Once the reaction was complete by TLC, it was worked up. The crude reaction mixture was poured into a separatory funnel, and ethyl acetate and water were added. The organic layer was separated and then washed with brine (1×). The organic layer was then dried over anhydrous MgSO$_4$, filtered, and the filtrate was concentrated under reduced pressure afford the crude product. The crude product was purified by flash chromatography. The crude product was loaded onto a silica column using minimal amount of ethyl acetate. The column column was placed on top of another, pre-equilibrated silica column. A gradient of ethyl acetate in heptane (1-100%) or methanol in dichloromethane (0-10%) was typically used to elute the product. Product fractions were concentrated under reduced pressure to afford the desired product.

Example 2—Synthesis of Compound 8A (2-((3-(4-bromophenyl)-8-methyl-1,4,8-triazaspiro[4.5]deca-1,3-dien-2-yl)thio)-N-(6-methoxypyridin-3-yl)acetamide)

General procedure A was followed, using acetamide 7A. The crude product was purified by flash chromatography with elution occurring in 10% methanol/dichloromethane solution to afford the title compound. $^1$H NMR (400 MHz, DMSO-d$_6$) δ 10.30 (s, 1H), 8.31 (d, J=2.29 Hz, 1H), 7.74-7.86 (m, 5H), 6.78 (d, J=8.87 Hz, 1H), 4.14 (s, 2H), 3.79 (s, 3H), 2.50-2.67 (m, 4H), 2.24 (s, 3H), 1.55-1.75 (m, 4H); MS (ESI+m/z 503.10, ESI−m/z 501.10); TLC: (90:10:0.5, DCM:MeOH:NH$_4$OH) R$_f$=0.56.

Example 3—Synthesis of Compound 8B (2-((3-(4-bromophenyl)-8-methyl-1,4,8-triazaspiro[4.5]deca-1,3-dien-2-yl)thio)-N-(6-chloropyridin-3-yl)acetamide)

General procedure A was followed using acetamide 7B. The crude product was purified by flash chromatography with elution occurring in 10% methanol/dichloromethane solution to afford the title compound. $^1$H NMR (400 MHz, DMSO-d$_6$) δ 10.72 (s, 1H), 8.63 (s, 1H), 8.10 (br d, J=9.15 Hz, 1H), 7.85 (q, J=8.23 Hz, 4H), 7.53 (d, J=8.60 Hz, 1H), 4.24 (s, 2H), 2.56-2.81 (m, 4H), 2.27 (br s, 3H), 1.55-1.85 (m, 4H); MS (ESI+m/z 507.95, ESI−m/z 505.95); TLC: (95:5:0.5, DCM:MeOH:NH$_4$OH) R$_f$=0.17.

Example 4—Synthesis of Compound 8C (2-((3-(4-bromophenyl)-8-methyl-1,4,8-triazaspiro[4.5]deca-1,3-dien-2-yl)thio)-N-(quinolin-3-yl)acetamide)

General procedure A was followed using acetamide 7C. The crude product was purified by flash chromatography with elution occurring in 10% methanol/dichloromethane solution to afford the title compound. $^1$H NMR (400 MHz, DMSO-d$_6$) δ 10.89 (br s, 1H), 8.95 (s, 1H), 8.67 (s, 1H), 7.96 (br d, J=8.33 Hz, 1H), 7.92 (br d, J=8.33 Hz, 1H), 7.78-7.87 (m, 4H), 7.52-7.72 (m, 2H), 4.29 (s, 2H), 2.43-2.52 (m, 4 H), 2.18 (br s, 3H), 1.55-1.85 (m, 4H); MS (ESI+m/z 523.05, ESI−m/z 521.00); TLC: (90:10:0.5, DCM:MeOH:NH$_4$OH) R$_f$=0.47.

Example 5—Synthesis of Compound 8D (2-((3-(4-bromophenyl)-8-methyl-1,4,8-triazaspiro[4.5]deca-1,3-dien-2-yl)thio)-N-(pyridin-4-yl)acetamide)

General procedure A was followed using acetamide 7D. The crude product was purified by flash chromatography with elution occurring in 13% methanol/dichloromethane solution to afford the title compound. $^1$H NMR (400 MHz, DMSO-d$_6$) δ 10.66 (s, 1H), 8.41 (br d, J=6.13 Hz, 2H), 7.78 (q, J=8.51 Hz, 4H), 7.52 (d, J=6.04 Hz, 2H), 4.18 (s, 2H), 2.50-2.73 (m, 4 H), 2.19 (br s, 3H), 1.28-1.91 (m, 4H); MS (ESI+m/z 473.05, ESI−m/z 471.05); TLC: (90:10:0.5, DCM:MeOH:NH$_4$OH) R$_f$=0.24.

Example 6—Synthesis of Compound 8E (2-((3-(4-bromophenyl)-8-methyl-1,4,8-triazaspiro[4.5]deca-1,3-dien-2-yl)thio)-N-cyclohexylacetamide)

General procedure A was followed, using acetamide 7E. Following the workup procedure in general procedure A afforded the title compound without column purification. $^1$H NMR (400 MHz, DMSO-d$_6$) δ 8.04 (br d, J=7.78 Hz, 1H), 7.78 (q, J=8.63 Hz, 4H), 3.89 (s, 2H), 3.45-3.55 (m, 1H), 2.50-2.71 (m, 4 H), 2.29 (s, 3H), 1.58-1.80 (m, 7H), 1.51 (br d, J=12.44 Hz, 1H), 1.05-1.28 (m, 6 H); MS (ESI+m/z 478.90, ESI−m/z 476.90); TLC: (90:10:0.5, DCM:MeOH:NH$_4$OH) R$_f$=0.60.

Example 7—Synthesis of Compound 8F (2-((3-(4-bromophenyl)-8-methyl-1,4,8-triazaspiro[4.5]deca-1,3-dien-2-yl)thio)-N-cyclopentylacetamide)

General procedure A was followed using acetamide 7F. The crude product was purified by flash chromatography with elution occurring in 10% methanol/dichloromethane solution to afford the title compound. $^1$H NMR (400 MHz, DMSO-d$_6$) δ 8.15 (br d, J=6.77 Hz, 1H), 7.79 (q, J=8.42 Hz, 4H), 3.92-4.01 (m, 1H), 3.91 (s, 2H), 2.50-2.71 (m, 4 H), 2.32 (s, 3H), 1.58-1.82 (m, 8H), 1.45-1.54 (m, 2H), 1.38 (td, J=6.27, 12.35 Hz, 2H); MS (ESI+m/z 464.10, ESI−m/z 462.15); TLC: (90:10:0.5, DCM:MeOH:NH$_4$OH) R$_f$=0.62.

Example 8—Synthesis of Compound 8G (N-benzyl-2-((3-(4-bromophenyl)-8-methyl-1,4,8-triazaspiro[4.5]deca-1,3-dien-2-yl)thio)acetamide)

General procedure A was followed using acetamide 7G. The crude product was purified by flash chromatography with elution occurring in 10% methanol/dichloromethane solution to afford the title compound. $^1$H NMR (400 MHz, DMSO-d$_6$) δ 8.65 (br t, J=5.81 Hz, 1H), 7.73-7.82 (m, 4H), 7.17-7.30 (m, 5H), 4.27 (d, J=5.95 Hz, 2H), 3.99 (s, 2H), 2.50-2.73 (m, 5 H), 2.28 (s, 3H), 1.66 (br s, 3H); MS (ESI+m/z 486.00, ESI−m/z 484.10); TLC: (90:10:0.5, DCM:MeOH:NH$_4$OH) R$_f$=0.59.

Examples 9-11—Synthesis of Compounds 3-5

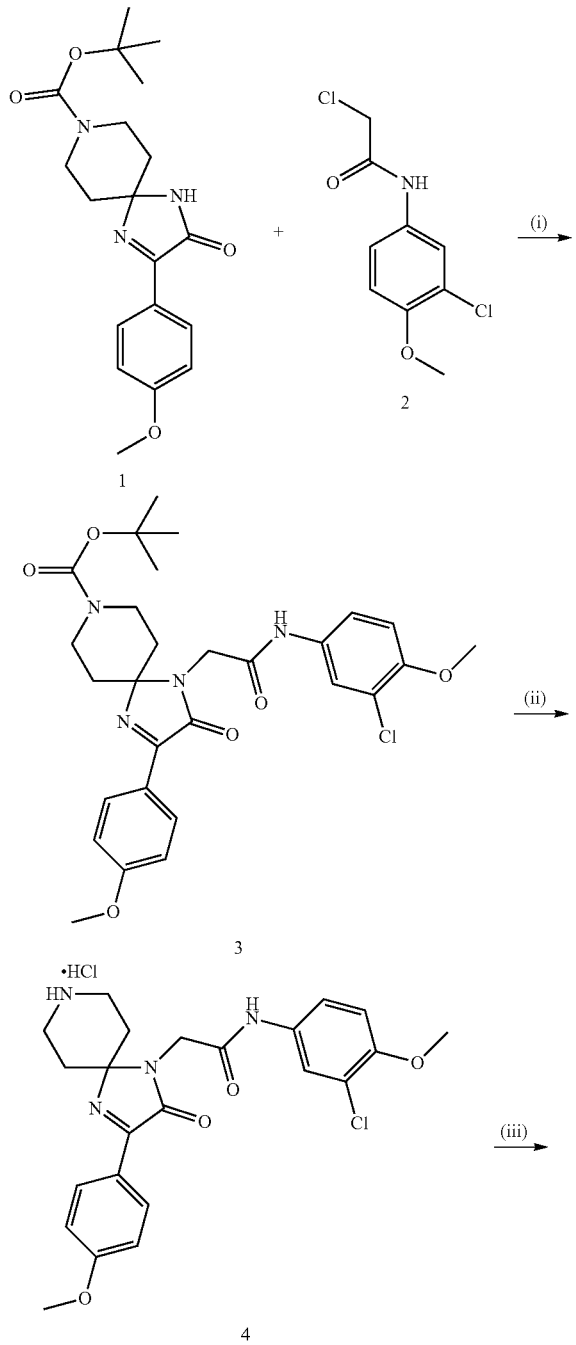

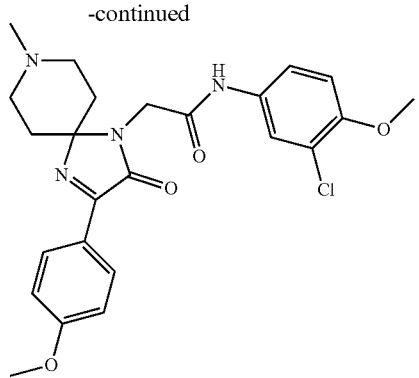

5

(i) NaH, DMF, 40° C.;
(ii) 4M HCl in Dioxane;
(iii) 37 wt % aqueous Formaldehyde, NaBH(OAc)$_3$, MeOH

Example 9—Synthesis of Compound 3 (tert-Butyl 4-(2-((3-chloro-4-methoxyphenyl)amino)-2-oxoethyl)-2-(4-methoxyphenyl)-3-oxo-1,4,8-triazaspiro[4.5]dec-1-ene-8-carboxylate)

To a solution of tert-butyl 2-(4-methmphenyl)-3-oxo-1,4,8-triazaspiro[4.5]dec-1-ene-8-carboxylate, 1 in anhydrous DMF was added sodium hydride (2 equiv.). The reaction mixture was warmed to 40° C. for thirty minutes. Next, 2-chloro-N-(3-chloro-4-methoxyphenyl)acetamide hydrochloride, 2 (1.76 equiv.) was added to the reaction mixture. The reaction mixture was kept at 40° C. and stirred under a flow of N$_2$. After five hours, the reaction was purified although TLC indicated starting material remained. The crude reaction mixture was cooled to room temperature and then loaded onto silica. The dry loaded material was placed into a dry-load column and packed. The dry-load column was placed on top of a pre-equilibrated (1% ethyl acetate in heptane) silica column. The crude product was purified using flash chromatography eluting with a gradient of 1-100% ethyl acetate in heptane. Desired fractions (elution at 50% ethyl acetate) were collected and concentrated under reduced pressure to afford the title compound. $^1$H NMR (400 MHz, CDCl$_3$) δ 8.67 (s, 1H), 8.46 (d, J=8.97 Hz, 2H), 7.55 (d, J=2.56 Hz, 1H), 7.27-7.39 (m, 1H), 6.99 (d, J=8.97 Hz, 2H), 6.84 (d, J=8.87 Hz, 1H), 4.01-4.22 (m, 2H), 3.88 (s, 3H), 3.86 (s, 3H), 3.39 (m, 2H), 2.21 (dt, J=4.80, 12.69 Hz, 2H), 1.50 (s, 9H), 1.19-1.40 (m, 4H); MS (ESI+m/z 501, ESI−m/z 556.15); TLC: (50:50 EA:HEP) R$_f$=0.21.

Example 10—Synthesis of Compound 4 (N-(3-chloro-4-methoxyphenyl)-2-(3-(4-methoxyphenyl)-2-oxo-1,4,8-triazaspiro[4.5]dec-3-en-1-yl)acetamide hydrochloride)

To a solution of 3, tert-butyl 4-(2-((3-chloro-4-methoxyphenyl)amino)-2-oxoethyl)-2-(4-methmphenyl)-3-oxo-1,4,8-triazaspiro[4.5]dec-1-ene-8-carboxylate in anhydrous dioxane was added 4M HCl in dioxane (3.3 equiv.). After one hour, no reaction was observed by TLC, so an additional portion of 4M HCl in dioxane (3.3 equiv.) was added. After one hour a new spot (baseline) was observed but starting material remained. An additional portion of 4M HCl in dioxane (3.3 equiv.) was added and the reaction mixture was stirred at 40° C. overnight. Overnight a yellow precipitate formed in the reaction mixture. The solid was filtered over a fritted funnel and rinsed with excess dioxane. The solid was transferred to a vial and dried under reduced pressure to afford the title compound. $^1$H NMR (400 MHz, DMSO-d$_6$) ≠ 10.48 (s, 1H), 9.22 (br d, J=9.70 Hz, 1H), 8.93 (br d, J=10.70 Hz,1H), 8.39 (d, J=8.97 Hz, 2H), 7.78 (d, J=2.47 Hz, 1H), 7.45 (dd, J=2.52, 9.01Hz, 1H), 7.07-7.14 (m, 3H), 4.98 (br s, 2H), 4.25 (s, 2H), 3.84 (s, 3H), 3.81 (s, 3H), 3.39-3.48 (m, 2H), 3.25-3.39 (m, 2H), 1.55 (br d, J=13.45Hz, 2H); MS (ESI+m/z 457.10, ESI−m/z 455.10); TLC: (95:5:0.5, DCM:MeOH:NH$_4$OH) R$_f$=0.03.

Example 11—Synthesis of Compound 5 (N-(3-chloro-4-methoxyphenyl)-2-(3-(4-methoxyphenyl)-8-methyl-2-oxo-1,4,8-triazaspiro[4.5]dec-3-en-1-yl)acetamide)

To a solution of 4, N-(3-chloro-4-methoxyphenyl)-2-(3-(4-methoxyphenyl)-2-oxo-1,4,8-triazaspiro[4.5]dec-3-en-1-yl)acetamide hydrochloride in methanol was added aqueous formaldehyde (37 wt% solution, 7 equiv.). The reaction mixture was stirred for 5 minutes then sodium triacetoxyborohydride (3 equiv.) was added. The reaction mixture was stirred overnight at room temperature. The next morning, TLC (95:5:0.5, DCM:MeOH:NH$_4$OH) showed the reaction was complete with new higher R$_f$ spot. The crude reaction was poured into a separatory funnel. To the separatory funnel was added dichloromethane. The organic layer was washed with saturated aqueous NaHCO$_3$ (1 x), followed by brine (1 x). The organic layer was dried over anhydrous Na$_2$SO$_4$, filtered and concentrated under reduced pressure to afford the title compound. $^1$H NMR (400 MHz, DMSO-d$_6$) δ 10.15 (s, 1H), 8.34 (d, J=8.97 Hz, 2H), 7.74 (d, J=2.47 Hz, 1H), 7.39 (dd, J=2.56, 8.97Hz, 1H), 7.03-7.12 (m, 3H), 4.24 (s, 2H), 3.81 (s, 3H), 3.80 (s, 3H), 2.78 (br s, 2H),2.29 (br s, 3H), 2.15-2.26 (m, 2H) 1.13-1.33(m, 3H); MS (ESI+m/z 471.10); TLC: (95:5:0.5, DCM:MeOH:NH$_4$OH) R$_f$=0.23

Examples 12-14 - Synthesis of Compounds 10, 11, and 12

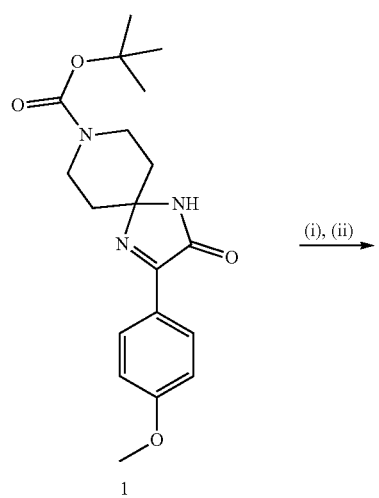

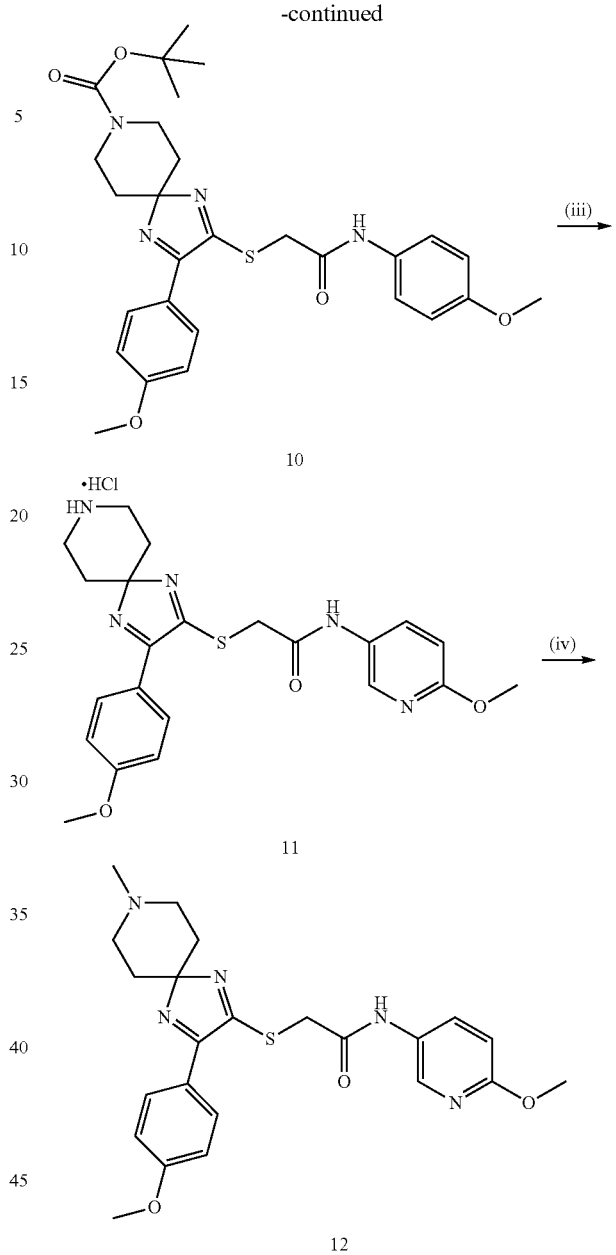

(i) Lawesson's Reagent, THF;
(ii) 2, 9. 2M aq. K$_2$CO$_3$, Acetonitrile;
(iii) 4M HCl in Dioxane;
(iv) 37 wt % aq. Formaldehyde, NaBH(OAc)$_3$, MeOH Example 12—Synthesis of Compound 10 (tent-Butyl 2-(4-methoxyphenyl)-3-((2-((6-methoxypyridin-3-yl)amino)-2-oxoethyl)thio)-1,4,8-triazaspiro[4.5]deca-1,3-diene-8-carboxylate)

To a solution of tert-butyl 2-(4-methmphenyl)-3-oxo-1,4,8-triazaspiro[4.5]dec-1-ene-8-carboxylate, 1 in anhydrous THF was added Lawesson's reagent (1 equiv.). The reaction mixture was allowed to stir for 48 hours at room temperature before the crude product was purified by flash chromatography. The crude reaction mixture was dry loaded onto silica. The dry loaded material was placed into a dry-load column and packed. The dry-load column was placed on top of a pre-equilibrated (2% ethyl acetate in heptane) silica column. The crude product was purified using flash chromatography eluting with a gradient of 2-100% ethyl acetate in heptane. Desired fractions (elution at 50% ethyl acetate) were collected and concentrated under reduced pressure to afford a crude solid. The solid was triturated with a mixture of heptane, dichloromethane, and ethyl acetate (3:2:1 v/v) and filtered over a fritted funnel to afford 9 tent-butyl 2-(4-methoxyphenyl)-3-thioxo-1,4,8-triazaspiro[4.5]dec-1-ene-8-carboxylate. MS (ESI +m/z 376.9, ESI- m/z 374.9); TLC: (95:0.5:0.5, DCM:MeOH:NH$_4$OH) R$_f$=0.68.

Next, to a solution of tent-butyl 2-(4-methoxyphenyl)-3-thioxo-1,4,8-triazaspiro[4.5]dec-1-ene-8-carboxylate, 9 in anhydrous acetonitrile was added 2-chloro-N-(3-chloro-4-methoxyphenyl)acetamide hydrochloride, 2 (1 equiv.). The reaction mixture was warmed to 40° C. Next, 2M aqueous potassium carbonate solution (2 equiv.) was added to the reaction mixture. The reaction continued at 40° C. overnight until TLC showed loss of starting materials and two new lower R$_f$ spots were observed. The crude reaction mixture was poured into a separatory funnel. To the funnel was added ethyl acetate and water. Separate organic layer and then washed with brine (1×). The organic layer was then dried over anhydrous MgSO$_4$, filtered, and the filtrate was concentrated under reduced pressure afford the crude product. The crude product was loaded onto a silica column using a minimal amount of dichloromethane. The column was placed on top of another pre-equilibrated silica column. A gradient of ethyl acetate in heptane (1-35%) was used to elute the product by flash chromatography. Product fractions were concentrated under reduced pressure to afford the title compound. $^1$H NMR (400 MHz, DMSO-d$_6$)δ 10.30 (s, 1H), 8.32 (d, J=2.38 Hz, 1H), 7.84-7.91 (m, 3H), 7.12 (d, J=8.97 Hz, 2H), 6.80 (d, J=8.97 Hz, 2H), 4.15 (s, 2H), 3.84 (s, 3H), 3.82 (s, 3H), 3.63-3.72 (m, 2H), 3.47-3.56 (m, 2H), 1.72 (br t, J=8.78 Hz, 2H),1.42 (br s, 11H); MS (ESI+m/z 540.20, ESI−m/z 538.15); TLC: (50:50, EA:Hep) R$_f$=0.29.

Example 13—Synthesis of Compound 11 (2-((3-(4-methoxyphenyl)-1,4,8-triazaspiro[4.5]deca-1,3-dien-2-yl)thio)-N-(6-methoxypyridin-3-yl)acetamide hydrochloride)

To a solution of 10, tert-butyl 2-(4-methoxyphenyl)-3-((2-((6-methoxypyridin-3-yl)amino)-2-oxoethyl)thio)-1,4,8-triazaspiro[4.5]deca-1,3-diene-8-carboxylate in anhydrous dioxane was added 4M HCl in dioxane (3 equiv.). After two hours, no starting materials were observed by TLC, and a new spot (baseline) was formed. A yellow precipitate formed in the reaction mixture. The solid was filtered over a fritted funnel and rinsed with excess dioxane. The solid was impure so it was loaded onto a silica column using a minimal amount of dichloromethane. A gradient of methanol in dichloromethane (0-15%) was used to elute the product via flash chromatography. Product fractions were concentrated under reduced pressure to afford the title compound. $^1$H NMR (400 MHz, DMSO-d$_6$) δ 10.40 (s, 1H), 8.45-8.60 (br s, 1H), 8.25-8.43 (m, 1H), 7.85-7.93 (m, 3H), 7.12 (d, J=8.87 Hz, 2H), 6.80 (d, J=8.78 Hz, 2H), 4.18 (s, 2H), 3.84 (s,3H), 3.81 (s, 3H), 3.22-3.56 (m, 4H), 1.84-2.01 (m, 2H),1.60-1.75 (m, 2H); MS (ESI+m/z 440.10, ESI−m/z 438.10); TLC: (50:50, EA:Hep) R$_f$=0.25

Example 14—Synthesis of Compound 12 (2-((3-(4-methoxyphenyl)-8-methyl-1,4,8-triazaspiro[4.5]deca-1,3-dien-2-yl)thio)-N-(6-methoxypyridin-3-yl)acetamide)

To a solution of 11, 2-((3-(4-methoxyphenyl)-1,4,8-triazaspiro[4.5]deca-1,3-dien-2-yl)thio)-N-(6-methoxypyridin-3-yl)acetamide hydrochloride in 95:5 dichloromethane:methanol was added aqueous formaldehyde (37 wt % solution, 7 equiv.). The reaction mixture was stirred for one hour then sodium triacetoxyborohydride (3 equiv.) was added. The reaction mixture was stirred overnight at room temperature. The next morning, TLC (95:5:0.5, DCM:MeOH:NH$_4$OH) showed the reaction was complete with new higher R$_f$ spot. The crude reaction was poured into a separatory funnel. To the separatory funnel was added dichloromethane and water. The organic layer was separated and washed with brine (1×). The organic layer was dried over anhydrous Na$_2$SO$_4$, filtered and concentrated under reduced pressure to afford the crude product. The crude product was impure so it was loaded onto a silica column using a minimal amount of dichloromethane. A gradient of methanol in dichloromethane (0-10%) was used to elute the product via flash chromatography. Product fractions were concentrated under reduced pressure to afford the title compound. $^1$H NMR (400 MHz, DMSO-d$_6$) δ 10.33 (s, 1H), 8.35 (d, J=2.38 Hz, 1H), 7.85-7.91 (m, 3H), 7.12 (d, J=8.02 Hz, 2H), 6.81 (d, J=9.06 Hz, 1H), 4.16 (s, 2H), 3.85 (s,3H), 3.82 (s, 3H), 2.53-2.81 (m, 4H), 2.15-2.40 (m, 2H), 1.92 (s, 3H),1.50-1.80 (m, 2H); MS (ESI+m/z 454.10, ESI−m/z 452.10); TLC: (95:5:0.5, DCM:MeOH:NH$_4$OH) R$_f$=0.22.

Examples 15-28: Synthesis of Compounds 33a-33l

-continued

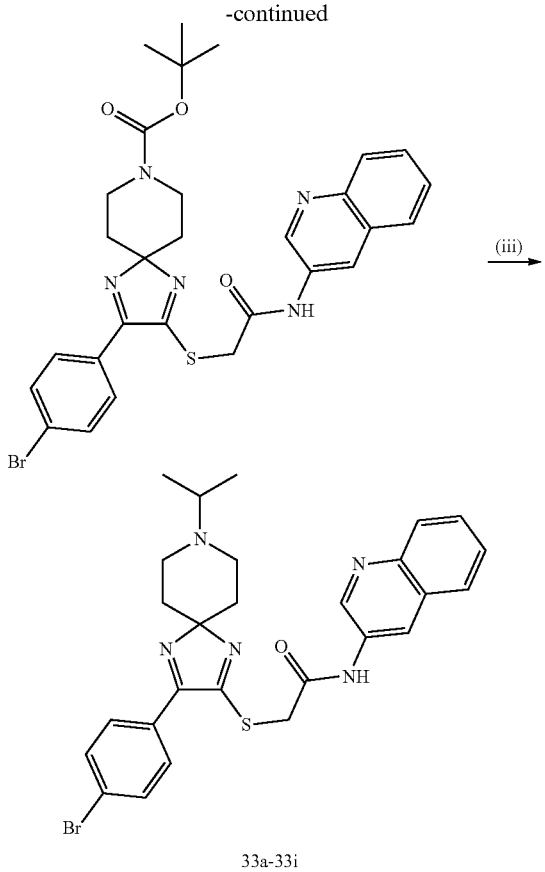

33a-33i

Reaction conditions:
(i) Lawesson's Reagent, THF;
(ii) 2-bromo-1-(quinolin-3-yl)ethan-1-one, NEt₃, DCM;
(iii) HCl, DCM then electrophile, NaBH(OAC)₃, DCM General Reaction Conditions for (i): To a solution of tert-butyl 2-(4-bromophenyl)-3-oxo-1,4,8-triazaspiro[4.5]dec-1-ene-8-carboxylate (1 equiv.) was added Lawesson's reagent (0.6 equiv) in THF (0.1 M) and the reaction mixture was heated to 60° C. until the reaction was complete by TLC. The reaction mixture was concentrated onto silica gel and purified by flash column chromatography (0-100% EtOAc in hexanes) to provide tert-butyl 2-(4-bromophenyl)-3-thioxo-1,4,8-triazaspiro[4.5]dec-1-ene-8-carboxylate.

General Reaction Conditions for (ii): To a solution of tert-butyl 2-(4-bromophenyl)-3-thioxo-1,4,8-triazaspiro[4.5]dec-1-ene-8-carboxylate (1 equiv.) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layer was dried, concentrated and purified by flash column chromatography (0-100% EtOAc in hexanes) to provide tert-butyl 2-(4-bromophenyl)-3-((2-oxo-2-(quinolin-3-ylamino)ethyl)thio)-1,4,8-triazaspiro[4.5]deca-1,3-diene-8-carboxylate.

General Reaction Conditions for (iii): To a solution of tert-butyl 2-(4-bromophenyl)-3-((2-oxo-2-(quinolin-3-ylamino)ethyl)thio)-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF (0.1 M) and triethylamine (5 equiv) and the appropriate electrophile (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (0-30% MeOH in DCM) to provide the desired product.

Examples 15-28

Compound 33a 2-((3-(4-bromophenyl)-8-isopropyl-1,4,8-triazaspiro[4.5]deca-1,3-dien-2-yl)thio)-N-(quinolin-3-yl)acetamide. 1H NMR (400 MHz, DMSO-d6) δ 10.81 (s, 1H), 8.97-8.90 (m, 1H), 8.00-7.95 (m, 1H), 7.95-7.90 (m, 1H), 7.89-7.83 (m, 2H), 7.83-7.77 (m, 2H), 7.71-7.63 (m, 1H), 7.62-7.55 (m, 1H), 4.26 (s, 2H), 2.73-2.60 (m, 4H), 1.88-1.71 (m, 2H), 1.62-1.40 (m, 2H), 0.90 (s, 3H), 0.88 (s, 3H).

Compound 33b 2-((3-(4-bromophenyl)-8-isopentyl-1,4,8-triazaspiro[4.5]deca-1,3-dien-2-yl)thio)-N-(quinolin-3-yl)acetamide. 1H NMR (400 MHz, DMSO-d6) δ 10.80 (s, 1H), 8.94 (d, J=2.5 Hz, 1H), 8.67 (d, J=2.5 Hz, 1H), 7.99-7.94 (m, 1H), 7.94-7.90 (m, 1H), 7.88-7.83 (m, 2H), 7.83-7.78 (m, 2H), 7.69-7.62 (m, 1H), 7.62-7.54 (m, 1H), 4.26 (s, 2H), 3.48-3.36 (m, 4H), 2.67-2.56 (m, 2H), 2.31-2.12 (m, 2H), 1.62-1.38 (m, 2H), 1.28-1.15 (m, 2H), 0.81 (d, J=6.5 Hz, 6H).

Compound 33c 2-((8-benzyl-3-(4-bromophenyl)-1,4,8-triazaspiro[4.5]deca-1,3-dien-2-yl)thio)-N-(quinolin-3-yl)acetamide 1H NMR (400 MHz, Methanol-d4) δ 8.17 (d, J=2.5 Hz, 1H), 7.95 (d, J =2.5 Hz, 1H), 7.25-7.19 (m, 1H), 7.12-7.02 (m, 3H), 6.96-6.87 (m, 3H), 6.85-6.78 (m, 1H), 6.43-6.30 (m, 3H), 6.30-6.17 (m, 2H), 3.42-3.34 (m, 2H), 2.76-2.60 (m, 4H), 2.10 -1.95 (m, 2H), 1.95 -1.78 (m, 2H).

Compound 33d 2-((3-(4-bromophenyl)-8-ethyl-1,4,8-triazaspiro[4.5]deca-1,3-dien-2-yl)thio)-N-(quinolin-3-yl)acetamide 1H NMR (400 MHz, DMSO-d6) δ 10.82 (s, 1H), 8.94 (d, J=2.5 Hz, 1H), 8.67 (d, J=2.4 Hz, 1H), 7.97 (d, J =8.4 Hz, 1H), 7.93 (d, J=8.1 Hz, 1H), 7.85 (d, J=8.5 Hz, 2H), 7.81 (d, J=8.5 Hz, 2H), 7.69-7.63 (m, 1H), 7.62-7.53 (m, 1H), 4.27 (s, 2H), 2.66 (s, 4H), 2.48-2.33 (m, 2H), 1.90-1.40 (m, 2H), 1.02-0.91 (m, 3H).

Compound 33e 2-((3-(4-bromophenyl)-8-propyl-1,4,8-triazaspiro[4.5]deca-1,3-dien-2-yl)thio)-N-(quinolin-3-yl)acetamide 1H NMR (400 MHz, DMSO-d6) δ 10.80 (s, 1H), 8.94 (d, J=2.5 Hz, 1H), 8.67 (d, J=2.4 Hz, 1H), 7.99-7.95 (m, 1H), 7.93 (dd, J=8.1, 1.5 Hz, 1H), 7.88-7.83 (m, 2H), 7.83-7.78 (m, 2H), 7.66 (ddd, J=8.4, 6.8, 1.5 Hz, 1H), 7.58 (ddd, J=8.2, 6.9, 1.3 Hz, 1H), 4.26 (s, 2H), 2.67-2.55 (m, 4H), 2.29-2.16 (m, 2H), 1.90-1.69 (m, 2H), 1.63-1.41 (m, 2H), 1.40-1.29 (m, 2H), 0.79 (t, J=7.3 Hz, 3H).

Compound 33f 2-((3-(4-bromophenyl)-8-isobutyl-1,4,8-triazaspiro[4.5]deca-1,3-dien-2-yl)thio)-N-(quinolin-3-yl)acetamide 1H NMR (400 MHz, DMSO-d6) δ 10.80 (s, 1H), 8.95 (d, J=2.6 Hz, 1H), 8.67 (d, J=2.5 Hz, 1H), 8.00-7.94 (m, 1H), 7.94-7.90 (m, 1H), 7.87-7.83 (m, 2H), 7.83-7.78 (m, 2H), 7.69-7.62 (m, 1H), 7.62-7.54 (m, 1H), 4.26 (s, 2H), 2.65-2.52 (m, 4H), 2.06-1.93 (m, 2H), 1.9-1.75 (m, 2H), 1.72-1.37 (m, 3H), 0.80 (d, J=6.5 Hz, 6H).

Compound 33g 2-((3-(4-bromophenyl)-8-(3,3,3-trifluoropropyl)-1,4,8-triazaspiro[4.5]deca-1,3-dien-2-yl)thio)-N-(quinolin-3-yl)acetamide 1H NMR (400 MHz, DMSO-d6) δ 10.80 (s, 1H), 8.94 (d, J=2.5 Hz, 1H), 8.67 (d, J=2.4 Hz, 1H), 8.00-7.95 (m, 1H), 7.95-7.91 (m, 1H), 7.88-7.83 (m, 2H), 7.83-7.78 (m, 2H), 7.66 (ddd, J=8.4, 6.9, 1.5 Hz, 1H), 7.58 (ddd, J=8.1, 6.9, 1.3 Hz, 1H), 4.28 (s, 2H), 2.68-2.54 (m, 6H), 1.96-1.40 (m, 6H).

Compound 33h 2-((3-(4-bromophenyl)-8-cyclopentyl-1,4,8-triazaspiro[4.5]deca-1,3-dien-2-yl)thio)-N-(quinolin-3-yl)acetamide 1H NMR (400 MHz, DMSO-d6) δ 10.82 (s, 1H), 8.96 (s, 1H), 8.68 (s, 1H), 8.03-7.90 (m, 2H), 7.90-7.77 (m, 4H), 7.73-7.63 (m, 1H), 7.62-7.54 (m, 1H), 4.25 (s, 2H), 2.77-2.23 (m, 5H), 2.03-0.83 (m, 12H).

Compound 33i 2-((3-(4-bromophenyl)-8-cyclobutyl-1,4,8-triazaspiro[4.5]deca-1,3-dien-2-yl)thio)-N-(quinolin-3-yl)acetamide 1H NMR (400 MHz, DMSO-d6) δ 10.81 (s, 1H), 8.96 (d, J=2.5 Hz, 1H), 8.67 (d, J=2.5 Hz, 1H), 8.00-7.96 (m, 1H), 7.95-7.90 (m, 1H), 7.88-7.83 (m, 2H), 7.83-7.77 (m, 2H), 7.66 (ddd, J=8.4, 6.9, 1.5 Hz, 1H), 7.58 (ddd, J=8.2, 6.9, 1.4 Hz, 1H), 4.25 (s, 2H), 2.67-2.54 (m, 1H), 2.49-2.28 (m, 1H), 1.91-1.61 (m, 5H), 1.63-1.10 (m, 4H).

Compound 33j 2-((3-(4-bromophenyl)-8-((1-methyl-1H-pyrazol-4-yl)methyl)-1,4,8-triazaspiro[4.5]deca-1,3-dien-2-yl)thio)-N-(quinolin-3-yl)acetamide 1H NMR (400 MHz, Chloroform-d) δ 9.88 (s, 1H), 8.85-8.76 (m, 1H), 8.65 (d, J=2.6 Hz, 1H), 8.11-8.02 (m, 1H), 7.87-7.77 (m, 3H), 7.70-7.61 (m, 3H), 7.56 (ddd, J=8.1, 6.9, 1.2 Hz, 1H), 7.47 (d, J=0.7 Hz, 1H), 7.37 (s, 1H), 4.00 (s, 2H), 3.91 (s, 3H), 3.62 (s, 2H), 3.04-2.72 (m, 4H), 2.40-2.07 (m, 2H), 1.78 (s, 2H).

Compound 33k 2-((3-(4-bromophenyl)-8-((1-isopropyl-1H-pyrazol-4-yl)methyl)-1,4,8-triazaspiro[4.5]deca-1,3-dien-2-yl)thio)-N-(quinolin-3-yl)acetamide 1H NMR (400 MHz, Chloroform-d) δ 9.89 (s, 1H), 8.80 (d, J=2.5 Hz, 1H), 8.66 (d, J=2.6 Hz, 1H), 8.08-7.98 (m, 1H), 7.87-7.76 (m, 3H), 7.69-7.63 (m, 3H), 7.56 (ddd, J=8.2, 6.9, 1.2 Hz, 1H), 7.50 (d, J=0.9 Hz, 1H), 7.44 (s, 1H), 4.50 (p, J=6.7 Hz, 1H), 4.01 (s, 2H), 3.62 (s, 2H), 3.09-2.76 (m, 4H), 2.40-2.12 (m, 2H), 1.74 (d, J=35.2 Hz, 2H), 1.53 (d, J=6.7 Hz, 5H).

Compound 33l 2-((3-(4-bromophenyl)-8-(methyl-d2)-1,4,8-triazaspiro[4.5]deca-1,3-dien-2-yl)thio)-N-(quinolin-3-yl)acetamide 1H NMR (400 MHz, DMSO-d6) δ 10.80 (s, 1H), 8.94 (d, J=2.5 Hz, 1H), 8.67 (d, J=2.4 Hz, 1H), 7.97 (dd, J=8.3, 1.1 Hz, 1H), 7.93 (dd, J=8.1, 1.4 Hz, 1H), 7.89-7.83 (m, 2H), 7.83-7.78 (m, 2H), 7.66 (ddd, J=8.4, 6.9, 1.5 Hz, 1H), 7.58 (ddd, J=8.1, 6.9, 1.3 Hz, 1H), 4.28 (s, 2H), 2.74-2.54 (m, 5H), 1.98 —1.36 (m, 4H).

Examples 29-34: Synthesis of Compounds 34a-34f

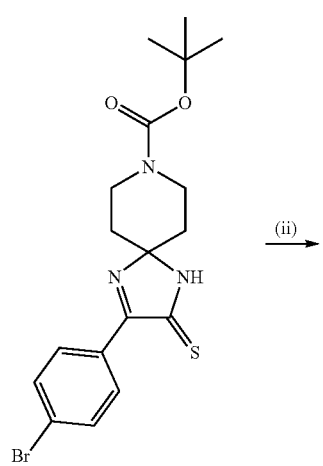

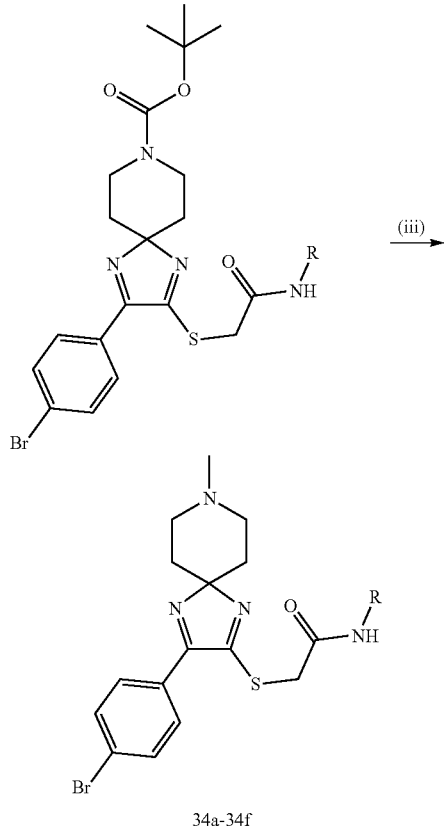

34a-34f

Reaction conditions:
(i) electrophile, NEt3, DCM;
(ii) HCl, DCM then formaldyhyde, NaBH(OAc)3, DCM Synthesis of Compound 34a 2-((3-(4-bromophenyl)-8-methyl-1,4,8-triazaspiro[4.5]deca-1,3-dien-2-yl)thio)-N-(quinolin-4-yl)acetamide To a solution of tert-butyl 2-(4-bromophenyl)-3-thioxo-1,4,8-triazaspiro[4.5]dec-1-ene-8-carboxylate (1 equiv) in DCM (0.1 M) was added 2-bromo-N-(quinolin-4-yl)acetamide (1 equiv) and triethylamine (3 equiv) and the reaction mixture was stirred for 10 hours. The reaction mixture was diluted with DCM and washed with saturated aqueous sodium bicarbonate. The organics were combined, dried, concentrated and purified by flash column chromatography (0-100% EtOAc in hexanes) to provide tert-butyl 2-(4-bromophenyl)-3-((2-oxo-2-(quinolin-6-ylamino)ethyl)thio)-1,4,8-triazaspiro[4.5]deca-1,3-diene-8-carboxylate 1H NMR (400 MHz, DMSO-d6) δ 10.65 (s, 1H), 8.80 (dd, J=4.2, 1.7 Hz, 1H), 8.34 (d, J=2.4 Hz, 1H), 8.33-8.27 (m, 1H), 8.04-7.92 (m, 1H), 7.92-7.76 (m, 5H), 7.49 (dd, J=8.3, 4.2 Hz, 1H), 4.27 (s, 2H), 3.70-3.58 (m, 2H), 3.57-3.46 (m, 2H), 1.74 (d, J=12.6, 8.4, 3.9 Hz, 2H), 1.56 -1.44 (m, 2H), 1.37 (s, 9H).

To a solution of tert-butyl 2-(4-bromophenyl)-3-((2-oxo-2-(quinolin-6-ylamino)ethyl)thio)-1,4,8-triazaspiro[4.5]deca-1,3-diene-8-carboxylate (1 equiv) in DCM was added 4 M HCl in dioxane (2 equiv) and the reaction mixture was allowed to stir for 4 hours. The reaction mixture was concentrated. The resulting residue was taken up in THF and formaldehyde (5 equiv) and triethylamine (5 equiv) were added followed by NaBH(OAc)3 (3 equiv) and the reaction mixture was stirred for 12 hours. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(4-bromophenyl)-8-methyl-1,4,8-triazaspiro[4.5]deca-1,3-dien-2-yl)thio)-N-(quinolin-6-yl)acetamide. 1H NMR (400 MHz, DMSO-d6) δ 10.67 (s, 1H), 8.80 (dd, J=4.2, 1.7 Hz, 1H), 8.35 (d, J=2.4 Hz, 1H), 8.29 (d, J=8.1 Hz, 1H), 7.99 (d, J=9.1 Hz, 1H), 7.89-7.77 (m, 5H), 7.49 (dd, J=8.3, 4.2 Hz, 1H), 4.26 (s, 2H), 2.67-2.54 (m, 4H), 2.22 (s, 3H), 1.85 -1.40 (m, 4H).

Synthesis of Compound 34b 2-((3-(4-bromophenyl)-8-methyl-1,4,8-triazaspiro[4.5]deca-1,3-dien-2-yl)thio)-N-(quinolin-6-yl)acetamide To a solution of tert-butyl 2-(4-bromophenyl)-3-thioxo-1,4,8-triazaspiro[4.5]dec-1-ene-8-carboxylate (1 equiv) in DCM (0.1 M) was added 2-bromo-N-(quinolin-6-yl)acetamide (1 equiv) and triethylamine (3 equiv) and the reaction mixture was stirred for 10 hours. The reaction mixture was diluted with DCM and washed with saturated aqueous sodium bicarbonate. The organics were combined, dried, concentrated and purified by flash column chromatography (0-100% EtOAc in hexanes) to provide tert-butyl 2-(4-bromophenyl)-3-((2-oxo-2-(quinolin-6-ylamino)ethyl)thio)-1,4,8-triazaspiro[4.5]deca-1,3-diene-8-carboxylate 1H NMR (400 MHz, DMSO-d6) δ 10.65 (s, 1H), 8.80 (dd, J=4.2, 1.7 Hz, 1H), 8.34 (d, J=2.4 Hz, 1H), 8.33-8.27 (m, 1H), 8.04-7.92 (m, 1H), 7.92-7.76 (m, 5H), 7.49 (dd, J=8.3, 4.2 Hz, 1H), 4.27 (s, 2H), 3.70-3.58 (m, 2H), 3.57-3.46 (m, 2H), 1.74 (d, J=12.6, 8.4, 3.9 Hz, 2H), 1.56 -1.44 (m, 2H), 1.37 (s, 9H).

To a solution of tert-butyl 2-(4-bromophenyl)-3-((2-oxo-2-(quinolin-6-ylamino)ethyl)thio)-1,4,8-triazaspiro[4.5]deca-1,3-diene-8-carboxylate (1 equiv) in DCM was added 4 M HCl in dioxane (2 equiv) and the reaction mixture was allowed to stir for 4 hours. The reaction mixture was concentrated. The resulting residue was taken up in THF and formaldehyde (5 equiv) and triethylamine (5 equiv) were added followed by NaBH(OAc)3 (3 equiv) and the reaction mixture was stirred for 12 hours. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(4-bromophenyl)-8-methyl-1,4,8-triazaspiro[4.5]deca-1,3-dien-2-yl)thio)-N-(quinolin-6-yl)acetamide. 1H NMR (400 MHz, DMSO-d6) δ 10.67 (s, 1H), 8.80 (dd, J=4.2, 1.7 Hz, 1H), 8.35 (d, J=2.4 Hz, 1H), 8.29 (d, J=8.1 Hz, 1H), 7.99 (d, J=9.1 Hz, 1H), 7.89-7.77 (m, 5H), 7.49 (dd, J=8.3, 4.2 Hz, 1H), 4.26 (s, 2H), 2.67-2.54 (m, 4H), 2.22 (s, 3H), 1.85 -1.40 (m, 4H).

Synthesis of Compound 34c 2-((3-(4-bromophenyl)-8-methyl-1,4,8-triazaspiro[4.5]deca-1,3-dien-2-yl)thio)-N-(quinolin-5-yl)acetamide To a solution of tert-butyl 2-(4-bromophenyl)-3-thioxo-1,4,8-triazaspiro[4.5]dec-1-ene-8-carboxylate (1 equiv) in DCM (0.1 M) was added 2-bromo-N-(quinolin-5-yl)acetamide (1 equiv) and triethylamine (3 equiv) and the reaction mixture was stirred for 10 hours. The reaction mixture was diluted with DCM and washed with saturated aqueous sodium bicarbonate. The organics were combined, dried, concentrated and purified by flash column chromatography (0-100% EtOAc in hexanes) to provide tert-butyl 2-(4-bromophenyl)-3-((2-oxo-2-(quinolin-5-ylamino)ethyl)thio)-1,4,8-triazaspiro[4.5]deca-1,3-diene-8-carboxylate.

To a solution of tert-butyl 2-(4-bromophenyl)-3-((2-oxo-2-(quinolin-5-ylamino)ethyl)thio)-1,4,8-triazaspiro[4.5]deca-1,3-diene-8-carboxylate (1 equiv) in DCM was added 4 M HCl in dioxane (2 equiv) and the reaction mixture was allowed to stir for 4 hours.

The reaction mixture was concentrated. The resulting residue was taken up in THF and formaldehyde (5 equiv) and triethylamine (5 equiv) were added followed by NaBH(OAc)3 (3 equiv) and the reaction mixture was stirred for 12 hours. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(4-bromophenyl)-8-methyl-1,4,8-triazaspiro[4.5]deca-1,3-dien-2-yl)thio)-N-(quinolin-5-yl)acetamide. 1H NMR (400 MHz, DMSO-d6) δ 10.41 (s, 1H), 8.93 (dd, J=4.2, 1.6 Hz, 1H), 8.52 (ddd, J=8.6, 1.7, 0.9 Hz, 1H), 7.96-7.71 (m, 7H), 7.57 (dd, J=8.6, 4.2 Hz, 1H), 4.36 (s, 2H), 2.75-2.56 (m, 4H), 2.25 (s, 3H), 1.89-1.59 (m, 4H).

Synthesis of Compound 34d 2-((3-(4-bromophenyl)-8-methyl-1,4,8-triazaspiro[4.5]deca-1,3-dien-2-yl)thio)-N-(quinolin-7-yl)acetamide To a solution of tert-butyl 2-(4-bromophenyl)-3-thioxo-1,4,8-triazaspiro[4.5]dec-1-ene-8-carboxylate (1 equiv) in DCM (0.1 M) was added 2-bromo-N-(quinolin-7-yl)acetamide (1 equiv) and triethylamine (3 equiv) and the reaction mixture was stirred for 10 hours. The reaction mixture was diluted with DCM and washed with saturated aqueous sodium bicarbonate. The organics were combined, dried, concentrated and purified by flash column chromatography (0-100% EtOAc in hexanes) to provide tert-butyl 2-(4-bromophenyl)-3-((2-oxo-2-(quinolin-7-ylamino)ethyl)thio)-1,4,8-triazaspiro[4.5]deca-1,3-diene-8-carboxylate.

To a solution of tert-butyl 2-(4-bromophenyl)-3-((2-oxo-2-(quinolin-7-ylamino)ethyl)thio)-1,4,8-triazaspiro[4.5]deca-1,3-diene-8-carboxylate (1 equiv) in DCM was added 4 M HCl in dioxane (2 equiv) and the reaction mixture was allowed to stir for 4 hours. The reaction mixture was concentrated. The resulting residue was taken up in THF and formaldehyde (5 equiv) and triethylamine (5 equiv) were added followed by NaBH(OAc)3 (3 equiv) and the reaction mixture was stirred for 12 hours. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(4-bromophenyl)-8-methyl-1,4,8-triazaspiro[4.5]deca-1,3-dien-2-yl)thio)-N-(quinolin-7-yl)acetamide. 1H NMR (400 MHz, DMSO-d6) δ 10.69 (s, 1H), 8.85 (dd, J=4.2, 1.8 Hz, 1H), 8.40 (d, J=2.0 Hz, 1H), 8.28 (d, J=8.1 Hz, 1H), 7.94 (d, J=8.9 Hz, 1H), 7.91-7.84 (m, 2H), 7.83-7.77 (m, 2H), 7.73 (dd, J=8.8, 2.1 Hz, 1H), 7.43 (dd, J=8.2, 4.2 Hz, 1H), 4.28 (s, 2H), 2.67-2.55 (m, 4H), 2.20 (s, 3H), 1.91-1.38 (m, 4H).

Synthesis of Compound 34e 2-((3-(4-bromophenyl)-8-methyl-1,4,8-triazaspiro[4.5]deca-1,3-dien-2-yl)thio)-N-(quinolin-8-yl)acetamide To a solution of tert-butyl 2-(4-bromophenyl)-3-thioxo-1,4,8-triazaspiro[4.5]dec-1-ene-8-carboxylate (1 equiv) in DCM (0.1 M) was added 2-bromo-N-(quinolin-8-yl)acetamide (1 equiv) and triethylamine (3 equiv) and the reaction mixture was stirred for 10 hours. The reaction mixture was diluted with DCM and washed with saturated aqueous sodium bicarbonate. The organics were combined, dried, concentrated and purified by flash column chromatography (0-100% EtOAc in hexanes) to provide tert-butyl 2-(4-bromophenyl)-3-((2-oxo-2-(quinolin-8-ylamino)ethyl)thio)-1,4,8-triazaspiro[4.5]deca-1,3-diene-8-carboxylate.

To a solution of tert-butyl 2-(4-bromophenyl)-3-((2-oxo-2-(quinolin-8-ylamino)ethyl)thio)-1,4,8-triazaspiro[4.5]deca-1,3-diene-8-carboxylate (1 equiv) in DCM was added 4 M HCl in dioxane (2 equiv) and the reaction mixture was allowed to stir for 4 hours. The reaction mixture was concentrated. The resulting residue was taken up in THF and formaldehyde (5 equiv) and triethylamine (5 equiv) were added followed by NaBH(OAc)3 (3 equiv) and the reaction mixture was stirred for 12 hours. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(4-bromophenyl)-8-methyl-1,4,8-triazaspiro[4.5]deca-1,3-dien-2-yl)thio)-N-(quinolin-8-yl)acetamide. 1H NMR (400 MHz, DMSO-d6) δ 10.65 (s, 1H), 8.85 (dd, J=4.2, 1.7 Hz, 1H), 8.60 (dd, J=7.6, 1.3 Hz, 1H), 8.42 (dd, J=8.3, 1.7 Hz, 1H), 7.90-7.79 (m, 4H), 7.69 (dd, J=8.3, 1.4 Hz, 1H), 7.64 (dd, J=8.3, 4.2 Hz, 1H), 7.62-7.56 (m, 1H), 4.34 (s, 2H), 2.50-2.37 (m, 4H), 2.07 (s, 3H), 1.86-1.17 (m, 4H).

Synthesis of Compound 34f 2-((3-(4-bromophenyl)-8-methyl-1,4,8-triazaspiro[4.5]deca-1,3-dien-2-yl)thio)-N-methyl-N-(quinolin-3-yl)acetamide To a solution of tert-butyl 2-(4-bromophenyl)-3-thioxo-1,4,8-triazaspiro[4.5]dec-1-ene-8-carboxylate (1 equiv) in DCM (0.1 M) was added 2-bromo-N-methyl-N-(quinolin-3-yl)acetamide (1 equiv) and triethylamine (3 equiv) and the reaction mixture was stirred for 10 hours. The reaction mixture was diluted with DCM and washed with saturated aqueous sodium bicarbonate. The organics were combined, dried, concentrated and purified by flash column chromatography (0-100% EtOAc in hexanes) to provide tert-butyl 2-(4-bromophenyl)-3-((2-(methyl(quinolin-3-yl)amino)-2-oxoethyl)thio)-1,4,8-triazaspiro[4.5]deca-1,3-diene-8-carboxylate.

To a solution of tert-butyl 2-(4-bromophenyl)-3-((2-(methyl(quinolin-3-yl)amino)-2-oxoethyl)thio)-1,4,8-triazaspiro[4.5]deca-1,3-diene-8-carboxylate (1 equiv) in DCM was added 4 M HCl in dioxane (2 equiv) and the reaction mixture was allowed to stir for 4 hours. The reaction mixture was concentrated. The resulting residue was taken up in THF and formaldehyde (5 equiv) and triethylamine (5 equiv) were added followed by NaBH(OAc)3 (3 equiv) and the reaction mixture was stirred for 12 hours. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(4-bromophenyl)-8-methyl-1,4,8-triazaspiro[4.5]deca-1,3-dien-2-yl)thio)-N-methyl-N-(quinolin-3-yl)acetamide. 1H NMR (400 MHz, DMSO-d6) δ 9.03 (s, 1H), 8.51 (s, 1H), 8.10 (d, J=8.5 Hz, 1H), 8.00 (dd, J=8.4, 1.4 Hz, 1H), 7.89-7.63 (m, 6H), 4.01 (s, 2H), 3.37 (s, 3H), 3.30 (s, 3H), 2.65-2.16 (m, 7H), 1.89-1.18 (m, 4H).

Examples 35-43: Synthesis of Compounds 35a-35i

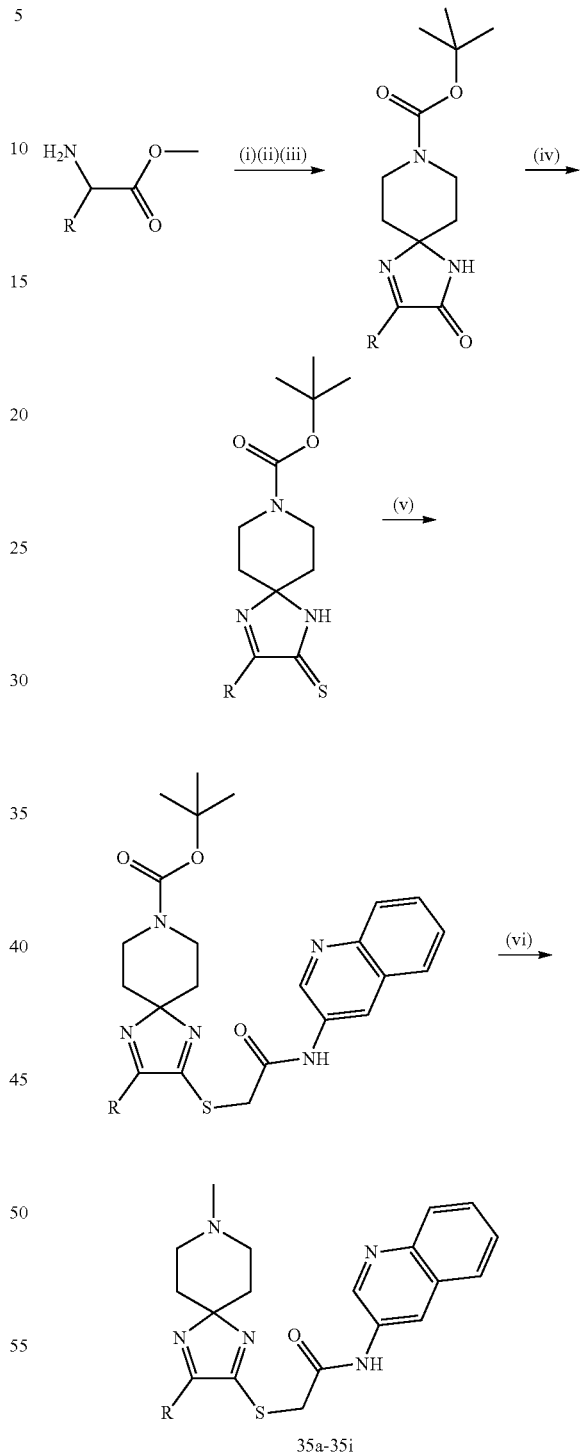

35a-35i

Reaction conditions:
(i) NH4OH, water;
(ii) Boc-Piperidinone, ethanol;
(iii) NBS, MeCN;
(iv) Lawesson's Reagent, THF;
(v) 2-bromo-1-(quinolin-3-yl)ethan-1-one, NEt3, DCM;
(vi) HCl, DCM then formaldehyde, NaBH(OAC)3, DCM

Synthesis of Compound 35a 2-((3-(4-fluorophenyl)-8-methyl-1,4,8-triazaspiro[4.5]deca-1,3-dien-2-yl)thio)-N-(quinolin-3-yl)acetamide Methyl amino(4-fluorophenyl)acetate HCl was stirred in 28% ammonium hydroxide (5mL/g) solution for 96 hours resulting in the formation of 2-amino-2-(4-fluorophenyl)acetamide as a white precipitate that was collected via filtration and used without further purification. To a solution of 2-amino-2-(4-fluorophenyl)acetamide (1 equiv) in ethanol (0.1 M) was added tert-Butyl 4-oxo-1-piperidinecarboxylate (1 equiv) and the reaction mixture was heated to reflux for 12 hours. The reaction mixture was cooled to room temperature and concentrated under reduced pressure. The resulting residue was dissolved in DCM (0.1 M) and N-bromosuccinimide (1 equiv) was added. The reaction mixture was stirred for 8 hours and saturated sodium bicarbonate was added. The resulting mixture was extracted with DCM. The organics were dried, concentrated and purified by FCC (0-100% EtOAc in hexanes) to provide tert-butyl 2-(4-fluorophenyl)-3-oxo-1,4,8-triazaspiro[4.5]dec-1-ene-8-carboxylate. 1H NMR (400 MHz, DMSO-d6) δ 10.28 (s, 1H), 8.48-8.37 (m, 2H), 7.41-7.31 (m, 2H), 3.71-3.50 (m, 4H), 1.79-1.69 (m, 2H), 1.68-1.56 (m, 2H), 1.44 (s, 9H).

To a solution of tert-butyl 2-(4-fluorophenyl)-3-oxo-1,4,8-triazaspiro[4.5]dec-1-ene-8-carboxylate (1 equiv.) in THF (0.1 M) was added Lawesson's reagent (0.6 equiv) and the reaction mixture was heated to 60° C. until the reaction was complete by TLC. The reaction mixture was concentrated onto silica gel and purified by flash column chromatography (0-100% EtOAc in hexanes) to provide tert-butyl 2-(4-fluorophenyl)-3-thioxo-1,4,8-triazaspiro[4.5]dec-1-ene-8-carboxylate. 1H NMR (400 MHz, DMSO-d6) δ 12.60 (s, 1H), 8.38 (dd, J=8.5, 5.7 Hz, 2H), 7.34 (t, J=8.7 Hz, 2H), 3.80-3.70 (m, 2H), 3.60-3.45 (m, 2H), 1.86 -1.67 (m, 4H), 1.45 (s, 9H).

To a solution of tert-butyl 2-(4-fluorophenyl)-3-thioxo-1,4,8-triazaspiro[4.5]dec-1-ene-8-carboxylate (1 equiv.) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layers were dried, concentrated and purified by flash column chromatography (0-100% EtOAc in hexanes) to provide tert-butyl 2-(4-fluorophenyl)-3-((2-oxo-2-(quinolin-3-ylamino)ethyl)thio)-1,4,8-triazaspiro[4.5]deca-1,3-diene-8-carboxylate.

To a solution of tert-butyl 2-(4-fluorophenyl)-3-((2-oxo-2-(quinolin-3-ylamino)ethyl)thio)-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF and triethylamine (5 equiv) and formaldehyde (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(4-fluorophenyl)-8-methyl-1,4,8-triazaspiro[4.5]deca-1,3-dien-2-yl)thio)-N-(quinolin-3-yl)acetamide. 1H NMR (400 MHz, DMSO-d6) δ 10.80 (s, 1H), 8.94 (d, J=2.5 Hz, 1H), 8.74-8.64 (m, 1H), 7.99 -7.95 (m, 1H), 7.95-7.92 (m, 1H), 7.91-7.88 (m, 2H), 7.70-7.51 (m, 4H), 4.27 (s, 2H), 3.34 (s, 3H), 2.64-2.55 (m, 4H), 2.26-2.11 (m, 2H), 1.91-1.42 (m, 4H).

Synthesis of Compound 35b 2-((8-methyl-3-phenyl-1,4,8-triazaspiro[4.5]deca-1,3-dien-2-yl)thio)-N-(quinolin-3-yl)acetamide Methyl 2-amino-2-phenylacetate hydrochloride was stirred in 28% ammonium hydroxide (5mug) solution for 96 hours resulting in the formation of 2-amino-2-phenylacetamide as a white precipitate that was collected via filtration and used without further purification. To a solution of 2-amino-2-phenylacetamide (1 equiv) in ethanol (0.1 M) was added tert-Butyl 4-oxo-1-piperidinecarbmlate (1 equiv) and the reaction mixture was heated to reflux for 12 hours. The reaction mixture was cooled to room temperature and concentrated under reduced pressure. The resulting residue was dissolved in DCM (0.1 M) and N-bromosuccinimide (1 equiv) was added. The reaction mixture was stirred for 8 hours and saturated sodium bicarbonate was added. The resulting mixture was extracted with DCM. The organics were dried, concentrated and purified by FCC (0-100% EtOAc in hexanes) to provide tert-butyl 3-oxo-2-phenyl-1,4,8-triazaspiro[4.5]dec-1-ene-8-carboxylate. 1H NMR (400 MHz, DMSO-d6) δ 10.26 (s, 1H), 8.47-8.23 (m, 2H), 7.61-7.48 (m, 3H), 3.70-3.50 (m, 4H), 1.80-1.68 (m, 2H), 1.68 -1.58 (m, 2H), 1.44 (s, 9H).

To a solution of tert-butyl 3-oxo-2-phenyl-1,4,8-triazaspiro[4.5]dec-1-ene-8-carboxylate (1 equiv.) in THF (0.1 M) was added Lawesson's reagent (0.6 equiv) and the reaction mixture was heated to 60° C. until the reaction was complete by TLC. The reaction mixture was concentrated onto silica gel and purified by flash column chromatography (0-100% EtOAc in hexanes) to provide tert-butyl 2-phenyl-3-thioxo-1,4,8-triazaspiro[4.5]dec-1-ene-8-carboxylate. 1H NMR (400 MHz, DMSO-d6) δ 12.58 (s, 1H), 8.30-8.23 (m, 2H), 7.60-7.46 (m, 3H), 3.81-3.70 (m, 2H), 3.60-3.44 (m, 2H), 1.86-1.62 (m, 4H), 1.45 (s, 9H).

To a solution of tert-butyl 2-phenyl-3-thioxo-1,4,8-triazaspiro[4.5]dec-1-ene-8-carboxylate (1 equiv.) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layers were dried, concentrated and purified by flash column chromatography (0-100% EtOAc in hexanes) to provide tert-butyl 2-((2-oxo-2-(quinolin-3-ylamino)ethyl)thio)-3-phenyl-1,4,8-triazaspiro[4.5]deca-1,3-diene-8-carboxylate.

To a solution of tert-butyl 2-((2-oxo-2-(quinolin-3-ylamino)ethyl)thio)-3-phenyl-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF and triethylamine (5 equiv) and formaldehyde (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (0-30% MeOH in DCM) to provide 2-((8-methyl-3-phenyl-1,4,8-triazaspiro[4.5]deca-1,3-dien-2-yl)thio)-N-(quinolin-3-yl)acetamide. 1H NMR (400 MHz, DMSO-d6) δ 10.81 (s, 1H), 8.94 (d, J=2.5 Hz, 1H), 8.67 (d, J=2.5 Hz, 1H), 8.02-7.90 (m, 4H), 7.66 (ddd, J=8.4, 6.9, 1.5 Hz, 1H), 7.58 (ddd, J=8.1, 6.8, 1.3 Hz, 1H), 7.49 -7.39 (m, 2H), 4.28 (s, 2H), 2.75-2.56 (m, 4H), 2.24 (s, 3H), 1.99-1.40 (m, 4H).

Synthesis of Compound 35c 2-((3-(4-chloro-3-fluorophenyl)-8-methyl-1,4,8-triazaspiro[4.5]deca-1,3-dien-2-yl)thio)-N-(quinolin-3-yl)acetamide Methyl 2-amino-2-(4-chloro-3-fluorophenyl)acetate hydrochloride was stirred in 28% ammonium hydroxide (5 mL/g) solution for 96 hours resulting in the formation of 2-amino-2-(4-chloro-3-fluorophenyl)acetamide as a white precipitate that was collected via filtration and used without further purification. To a solution of 2-amino-2-(4-chloro-3-fluorophenyl)acetamide (1 equiv) in ethanol (0.1 M) was added tert-Butyl 4-oxo-1-piperidinecarboxylate (1 equiv) and the reaction mixture was heated to reflux for 12 hours. The reaction mixture was cooled to room temperature and concentrated under reduced pressure. The resulting residue was dissolved in DCM (0.1 M) and N-bromosuccinimide (1 equiv) was added. The reaction mixture was stirred for 8 hours and saturated sodium bicarbonate was added. The resulting mixture was extracted with DCM. The organics were dried, concentrated and purified by FCC (0-100% EtOAc in hexanes) to provide tert-butyl 2-(4-chloro-3-fluorophenyl)-3-oxo-1,4,8-triazaspiro[4.5]dec-1-ene-8-carboxylate. 1H NMR (400 MHz, DMSO-d6) δ 10.37 (s, 1H), 8.29 (dd, J=10.4, 1.8 Hz, 1H), 8.20 (ddd, J=8.4, 1.8, 0.8 Hz, 1H), 7.78 (dd, J=8.4, 7.7 Hz, 1H), 3.69-3.52 (m, 4H), 1.73 (d, J=6.8 Hz, 4H), 1.44 (s, 9H).

To a solution of tert-butyl 2-(4-chloro-3-fluorophenyl)-3-oxo-1,4,8-triazaspiro[4.5]dec-1-ene-8-carboxylate (1 equiv.) in THF (0.1 M) was added Lawesson's reagent (0.6 equiv) and the reaction mixture was heated to 60° C. until the reaction was complete by TLC. The reaction mixture was concentrated onto silica gel and purified by flash column chromatography (0-100% EtOAc in hexanes) to provide tert-butyl 2-(4-chloro-3-fluorophenyl)-3-thioxo-1,4,8-triazaspiro[4.5]dec-1-ene-8-carboxylate. 1H NMR (400 MHz, DMSO-d6) δ 12.58 (s, 1H), 8.30-8.23 (m, 2H), 7.60-7.46 (m, 3H), 3.81-3.70 (m, 2H), 3.60-3.44 (m, 2H), 1.86-1.62 (m, 4H), 1.45 (s, 9H).

To a solution of tert-butyl 2-(4-chloro-3-fluorophenyl)-3-thioxo-1,4,8-triazaspiro[4.5]dec-1-ene-8-carboxylate (1 equiv.) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layers were dried, concentrated and purified by flash column chromatography (0-100% EtOAc in hexanes) to provide tert-butyl 2-(4-chloro-3-fluorophenyl)-3-((2-oxo-2-(quinolin-3-ylamino)ethyl)thio)-1,4,8-triazaspiro[4.5]deca-1,3-diene-8-carboxylate. 1H NMR (400 MHz, DMSO-d6) δ 10.78 (s, 1H), 8.91 (d, J=2.5 Hz, 1H), 8.71-8.61 (m, 1H), 8.00-7.95 (m, 1H), 7.95-7.91 (m, 1H), 7.90-7.83 (m, 2H), 7.81-7.76 (m, 1H), 7.67 (ddd, J=8.4, 6.9, 1.5 Hz, 1H), 7.58 (ddd, J=8.2, 6.9, 1.3 Hz, 1H), 4.29 (s, 2H), 3.70-3.58 (m, 2H), 3.58-3.45 (m, 2H), 1.82-1.65 (m, 2H), 1.60-1.43 (m, 2H), 1.38 (s, 9H).

To a solution of tert-butyl 2-(4-chloro-3-fluorophenyl)-3-((2-oxo-2-(quinolin-3-ylamino)ethyl)thio)-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF and triethylamine (5 equiv) and formaldehyde (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(4-chloro-3-fluorophenyl)-8-methyl-1,4,8-triazaspiro[4.5]deca-1,3-dien-2-yl)thio)-N-(quinolin-3-yl)acetamide. 1H NMR (400 MHz, DMSO-d6) δ 10.80 (s, 1H), 8.94 (d, J=2.5 Hz, 1H), 8.67 (d, J=2.5 Hz, 1H), 7.99-7.95 (m, 1H), 7.93 (d, J=7.7 Hz, 1H), 7.89-7.82 (m, 2H), 7.80-7.75 (m, 1H), 7.66 (ddd, J=8.5, 6.9, 1.5 Hz, 1H), 7.58 (ddd, J=8.1, 6.8, 1.3 Hz, 1H), 4.29 (s, 2H), 2.63-2.55 (m, 4H), 2.20 (s, 3H), 1.93-1.38 (m, 4H).

Synthesis of Compound 35d 2-((3-(3-bromophenyl)-8-methyl-1,4,8-triazaspiro[4.5]deca-1,3-dien-2-yl)thio)-N-(quinolin-3-yl)acetamide Methyl 2-amino-2-(3-bromophenyl)acetate was stirred in 28% ammonium hydroxide (5 mL/g) solution for 96 hours resulting in the formation of 2-amino-2-(3-bromophenyl)acetamide as a white precipitate that was collected via filtration and used without further purification. To a solution of 2-amino-2-(3-bromophenyl)acetamide (1 equiv) in ethanol (0.1 M) was added tert-Butyl 4-oxo-1-piperidinecarboxylate (1 equiv) and the reaction mixture was heated to reflux for 12 hours. The reaction mixture was cooled to room temperature and concentrated under reduced pressure. The resulting residue was dissolved in DCM (0.1 M) and N-bromosuccinimide (1 equiv) was added. The reaction mixture was stirred for 8 hours and saturated sodium bicarbonate was added. The resulting mixture was extracted with DCM. The organics were dried, concentrated and purified by FCC (0-100% EtOAc in hexanes) to provide tert-butyl 2-(3-bromophenyl)-3-oxo-1,4,8-triazaspiro[4.5]dec-1-ene-8-carboxylate. 1H NMR (400 MHz, DMSO-d6) δ 10.33 (s, 1H), 8.54-8.48 (m, 1H), 8.39-8.25 (m, 1H), 7.80 (d, J=8.0, 2.1, 1.1 Hz, 1H), 7.57-7.44 (m, 1H), 3.60 (d, J=19.5 Hz, 4H), 1.73 (d, J=7.4 Hz, 2H), 1.69-1.55 (m, 2H), 1.44 (s, 9H).

To a solution of tert-butyl 2-(3-bromophenyl)-3-oxo-1,4,8-triazaspiro[4.5]dec-1-ene-8-carboxylate (1 equiv.) in THF (0.1 M) was added Lawesson's reagent (0.6 equiv) and the reaction mixture was heated to 60° C. until the reaction was complete by TLC. The reaction mixture was concentrated onto silica gel and purified by flash column chromatography (O-100% EtOAc in hexanes) to provide tert-butyl 2-(3-bromophenyl)-3-thioxo-1,4,8-triazaspiro[4.5]dec-1-ene-8-carboxylate. 1H NMR (400 MHz, DMSO-d6) δ 12.63 (s, 1H), 8.51-8.42 (m, 1H), 8.27 (dt, J=7.8, 1.3 Hz, 1H), 7.77 (ddd, J=8.0, 2.1, 1.1 Hz, 1H), 7.51 -7.44 (m, 1H), 3.82-3.68 (m, 2H), 3.61-3.43 (m, 2H), 1.86-1.66 (m, 4H), 1.45 (s, 9H).

To a solution of tert-butyl 2-(3-bromophenyl)-3-thioxo-1,4,8-triazaspiro[4.5]dec-1-ene-8-carboxylate (1 equiv.) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layers were dried, concentrated and purified by flash column chromatography (0-100% EtOAc in hexanes) to provide tert-butyl 2-(3-bromophenyl)-3-((2-oxo-2-(quinolin-3-ylamino)ethyl)thio)-1,4,8-triazaspiro[4.5]deca-1,3-diene-8-carboxylate. 1H NMR (400 MHz, DMSO-d6) δ 10.78 (s, 1H), 8.91 (d, J=2.6 Hz, 1H), 8.70-8.59 (m, 1H), 8.05 (t, J=1.8 Hz, 1H), 8.00-7.95 (m, 1H), 7.95-7.90 (m, 2H), 7.84 (ddd, J=8.1, 2.1, 1.0 Hz, 1H), 7.67 (ddd, J=8.4, 6.9, 1.5 Hz, 1H), 7.61-7.54 (m, 2H), 4.28 (s, 2H), 3.71-3.58 (m, 2H), 3.57-3.46 (m, 2H), 1.80-1.68 (m, 2H), 1.60-1.42 (m, 2H), 1.38 (s, 9H).

To a solution of tert-butyl 2-(3-bromophenyl)-3-((2-oxo-2-(quinolin-3-ylamino)ethyl)thio)-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF and triethylamine (5 equiv) and formaldehyde (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (O-30% MeOH in DCM) to provide 2-((3-(3-bromophenyl)-8-methyl-1,4,8-triazaspiro[4.5]deca-1,3-dien-2-yl)thio)-N-(quinolin-3-yl)acetamide. 1H NMR (400 MHz, DMSO-d6) δ 10.79 (s, 1H), 8.94 (d, J=2.5 Hz, 1H), 8.67 (d, J=2.5 Hz, 1H), 8.03 (t, J=1.8 Hz, 1H), 7.99-7.93 (m, 1H), 7.93-7.88 (m, 2H), 7.83 (ddd, J=8.1, 2.1, 1.0 Hz, 1H), 7.66 (ddd, J=8.4, 6.9, 1.5 Hz, 1H), 7.62-7.54 (m, 2H), 4.28 (s, 2H), 2.59 (s, 4H), 2.21 (s, 3H), 1.94-1.48 (m, 4H).

Synthesis of Compound 35e 2-((8-methyl-3-(naphthalen-2-yl)-1,4,8-triazaspiro[4.5]deca-1,3-dien-2-yl)thio)-N-(quinolin-3-yl)acetamide Methyl amino(2-naphthyl)acetate hydrochloride was stirred in 28% ammonium hydroxide (5 mL/g) solution for 96 hours resulting in the formation of 2-amino-2-(naphthalen-2-yl)acetamide as a white precipitate that was collected via filtration and used without further purification. To a solution of 2-amino-2-(naphthalen-2-yl)acetamide (1 equiv) in ethanol (0.1 M) was added tert-Butyl 4-oxo-1-piperidinecarboxylate (1 equiv) and the reaction mixture was heated to reflux for 12 hours. The reaction mixture was cooled to room temperature and concentrated under reduced pressure. The resulting residue was dissolved in DCM (0.1 M) and N-bromosuccinimide (1 equiv) was added. The reaction mixture was stirred for 8 hours and saturated sodium bicarbonate was added. The resulting mixture was extracted with DCM. The organics were dried, concentrated and purified by FCC (0-100% EtOAc in hexanes) to provide tert-butyl 2-(naphthalen-2-yl)-3-oxo-1,4,8-triazaspiro[4.5]dec-1-ene-8-carboxylate. 1H NMR (400 MHz, DMSO-d6) δ 10.35 (s, 1H), 9.18-9.11 (m, 1H), 8.28 (dd, J=8.6, 1.6 Hz, 1H), 8.12-7.96 (m, 3H), 7.68-7.57 (m, 2H), 3.77-3.64 (m, 2H), 3.64-3.51 (m, 1H), 1.86-1.73 (m, 2H), 1.73-1.62 (m, 2H), 1.45 (s, 9H).

To a solution of tert-butyl 2-(naphthalen-2-yl)-3-oxo-1,4,8-triazaspiro[4.5]dec-1-ene-8-carboxylate (1 equiv.) in THF (0.1 M) was added Lawesson's reagent (0.6 equiv) and the reaction mixture was heated to 60° C. until the reaction was complete by TLC. The reaction mixture was concentrated onto silica gel and purified by flash column chromatography (O-100% EtOAc in hexanes) to provide tert-butyl 2-(naphthalen-2-yl)-3-thioxo-1,4,8-triazaspiro[4.5]dec-1-ene-8-carboxylate.

To a solution of tert-butyl 2-(naphthalen-2-yl)-3-thioxo-1,4,8-triazaspiro[4.5]dec-1-ene-8-carboxylate (1 equiv) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layers were dried, concentrated and purified by flash column chromatography (0-100% EtOAc in hexanes) to provide tert-butyl 2-(naphthalen-2-yl)-3-((2-oxo-2-(quinolin-3-ylamino)ethyl)thio)-1,4,8-triazaspiro[4.5]deca-1,3-diene-8-carboxylate. 1H NMR (400 MHz, DMSO-d6) δ 10.80 (s, 1H), 8.93 (d, J=2.5 Hz, 1H), 8.73-8.64 (m, 1H), 8.59-8.52 (m, 1H), 8.17-8.09 (m, 2H), 8.09-7.88 (m, 4H), 7.74-7.63 (m, 3H), 7.62-7.55 (m, 1H), 4.32 (s, 2H), 3.68 (s, 2H), 3.61-3.46 (m, 2H), 1.88-1.71 (m, 2H), 1.57-1.43 (m, 1H), 1.39 (s, 9H).

To a solution of tert-butyl 2-(naphthalen-2-yl)-3-((2-oxo-2-(quinolin-3-ylamino)ethyl)thio)-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF and triethylamine (5 equiv) and formaldehyde (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (0-30% MeOH in DCM) to provide 2-((8-methyl-3-(naphthalen-2-yl)-1,4,8-triazaspiro[4.5]deca-1,3-dien-2-yl)thio)-N-(quinolin-3-yl)acetamide. 1H NMR (400 MHz, DMSO-d6) δ 10.79 (s, 1H), 8.94 (d, J=2.5 Hz, 1H), 8.67 (d, J=2.5 Hz, 1H), 7.99-7.95 (m, 1H), 7.95-7.91 (m, 1H), 7.91-7.85 (m, 2H), 7.66 (ddd, J=8.4, 6.9, 1.5 Hz, 1H), 7.58 (ddd, J=8.1, 6.8, 1.3 Hz, 1H), 7.16-7.10 (m, 2H), 4.26 (s, 2H), 3.86 (s, 3H), 3.32 (s, 3H), 2.65-2.53 (m, 4H), 2.24-2.15 (m, 2H), 1.89-1.29 (m, 4H).

Synthesis of Compound 35f 2-((3-(4-methoxyphenyl)-8-methyl-1,4,8-triazaspiro[4.5]deca-1,3-dien-2-yl)thio)-N-(quinolin-3-yl)acetamide methyl amino(4-methoxyphenyl)acetate hydrochloride was stirred in 28% ammonium hydroxide (Smug) solution for 96 hours resulting in the formation of 2-amino-2-(4-methoxyphenyl)acetamide as a white precipitate that was collected via filtration and used without further purification. To a solution of 2-amino-2-(4-methoxyphenyl)acetamide (1 equiv) in ethanol (0.1 M) was added tert-Butyl 4-oxo-1-piperidinecarboxylate (1 equiv) and the reaction mixture was heated to reflux for 12 hours. The reaction mixture was cooled to room temperature and concentrated under reduced pressure. The resulting residue was dissolved in DCM (0.1 M) and N-bromosuccinimide (1 equiv) was added. The reaction mixture was stirred for 8 hours and saturated sodium bicarbonate was added. The resulting mixture was extracted with DCM. The organics were dried, concentrated and purified by FCC (0-100% EtOAc in hexanes) to provide tert-butyl 2-(4-methoxyphenyl)-3-oxo-1,4,8-triazaspiro[4.5]dec-1-ene-8-carboxylate. 1H NMR (400 MHz, DMSO-d6) δ 10.20 (s, 1H), 8.39-8.29 (m, 2H), 7.11-7.01 (m, 2H), 3.83 (s, 3H), 3.71-3.48 (m, 4H), 1.78-1.67 (m, 2H), 1.67-1.54 (m, 2H), 1.44 (s, 9H).

To a solution of tert-butyl 2-(4-methoxyphenyl)-3-oxo-1,4,8-triazaspiro[4.5]dec-1-ene-8-carboxylate (1 equiv.) in THF (0.1 M) was added Lawesson's reagent (0.6 equiv) and the reaction mixture was heated to 60° C. until the reaction was complete by TLC. The reaction mixture was concentrated onto silica gel and purified by flash column chromatography (0-100% EtOAc in hexanes) to provide tert-butyl 2-(4-methoxyphenyl)-3-thioxo-1,4,8-triazaspiro[4.5]dec-1-ene-8-carboxylate.

To a solution of tert-butyl 2-(4-methoxyphenyl)-3-thioxo-1,4,8-triazaspiro[4.5]dec-1-ene-8-carboxylate (1 equiv.) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layers were dried, concentrated and purified by flash column chromatography (O-100% EtOAc in hexanes) to provide tert-butyl 2-(4-methoxyphenyl)-3-((2-oxo-2-(quinolin-3-ylamino)ethyl)thio)-1,4,8-triazaspiro[4.5]deca-1,3-diene-8-carboxylate. 1H NMR (400 MHz, DMSO-d6) δ 10.77 (s, 1H), 8.92 (d, J=2.5 Hz, 1H), 8.70-8.61 (m, 1H), 7.99-7.93 (m, 1H), 7.93-7.87 (m, 2H), 7.66 (ddd, J=8.4, 6.9, 1.5 Hz, 1H), 7.58 (ddd, J=8.1, 6.8, 1.3 Hz, 1H), 7.20-7.08 (m, 2H), 4.27 (s, 2H), 3.86 (s, 3H), 3.73-3.57 (m, 2H), 3.57-3.42 (m, 2H), 1.81-1.67 (m, 2H), 1.50-1.40 (m, 2H), 1.37 (s, 9H).

To a solution of tert-butyl 2-(4-methoxyphenyl)-3-((2-oxo-2-(quinolin-3-ylamino)ethyl)thio)-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF and triethylamine (5 equiv) and formaldehyde (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(4-methoxyphenyl)-8-methyl-1,4,8-triazaspiro[4.5]deca-1,3-dien-2-yl)thio)-N-(quinolin-3-yl)acetamide. 1H NMR (400 MHz, DMSO-d6) δ 10.79 (s, 1H), 8.94 (d, J=2.5 Hz, 1H), 8.67 (d, J=2.5 Hz, 1H), 7.99-7.95 (m, 1H), 7.95-7.91 (m, 1H), 7.91-7.85 (m, 2H), 7.66 (ddd, J=8.4, 6.9, 1.5 Hz, 1H), 7.58 (ddd, J=8.1, 6.8, 1.3 Hz, 1H), 7.16-7.10 (m, 2H), 4.26 (s, 2H), 3.86 (s, 3H), 2.65-2.53 (m, 4H), 2.20 (s, 3H), 1.89-1.29 (m, 4H).

Synthesis of Compound 35 g 2-((3-(2-bromophenyl)-8-methyl-1,4,8-triazaspiro[4.5]deca-1,3-dien-2-yl)thio)-N-(quinolin-3-yl)acetamide methyl 2-amino-2-(2-bromophenyl)acetate was stirred in 28% ammonium hydroxide (5 mL/g) solution for 96 hours resulting in the formation of 2-amino-2-(2-bromophenyl)acetamide as a white precipitate that was collected via filtration and used without further purification. To a solution of 2-amino-2-(2-bromophenyl)acetamide (1 equiv) in ethanol (0.1 M) was added tert-Butyl 4-oxo-1-piperidinecarboxylate (1 equiv) and the reaction mixture was heated to reflux for 12 hours. The reaction mixture was cooled to room temperature and concentrated under reduced pressure. The resulting residue was dissolved in DCM (0.1 M) and N-bromosuccinimide (1 equiv) was added. The reaction mixture was stirred for 8 hours and saturated sodium bicarbonate was added. The resulting mixture was extracted with DCM. The organics were dried, concentrated and purified by FCC (0-100% EtOAc in hexanes) to provide tert-butyl 2-(2-bromophenyl)-3-oxo-1,4,8-triazaspiro[4.5]dec-1-ene-8-carboxylate. 1H NMR (400 MHz, DMSO-d6) δ 10.23 (s, 1H), 7.82-7.74 (m, 1H), 7.64-7.40 (m, 3H), 3.73-3.49 (m, 4H), 1.78-1.68 (m, 4H), 1.44 (s, 9H).

To a solution of tert-butyl 2-(2-bromophenyl)-3-oxo-1,4,8-triazaspiro[4.5]dec-1-ene-8-carboxylate (1 equiv) in THF (0.1 M) was added Lawesson's reagent (0.6 equiv) and the reaction mixture was heated to 60 ° C. until the reaction was complete by TLC. The reaction mixture was concentrated onto silica gel and purified by flash column chromatography (0-100% EtOAc in hexanes) to provide tert-butyl 2-(2-bromophenyl)-3-thioxo-1,4,8-triazaspiro[4.5]dec-1-ene-8-carboxylate. 1H NMR (400 MHz, DMSO-d6) 6 12.55 (s, 1H), 7.73 (dt, J=7.8, 0.9 Hz, 1H), 7.53-7.40 (m, 3H), 3.85-3.72 (m, 2H), 3.55-3.43 (m, 2H), 1.90-1.70 (m, 4H), 1.44 (s, 9H).

To a solution tert-butyl 2-(2-bromophenyl)-3-thioxo-1,4,8-triazaspiro[4.5]dec-1-ene-8-carboxylate (1 equiv.) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layers were dried, concentrated and purified by flash column chromatography (0-100% EtOAc in hexanes) to provide tert-butyl 2-(2-bromophenyl)-3-((2-oxo-2-(quinolin-3-ylamino)ethyl)thio)-1,4,8-triazaspiro[4.5]deca-1,3-diene-8-carboxylate. 1H NMR (400 MHz, DMSO-d6) δ 10.78 (s, 1H), 8.90 (d, J=2.5 Hz, 1H), 8.65 (d, J=2.4 Hz, 1H), 8.01-7.91 (m, 2H), 7.83 (dd, J=8.2, 1.2 Hz, 1H), 7.66 (ddd, J=8.4, 6.9, 1.5 Hz, 1H), 7.63-7.47 (m, 4H), 4.23 (s, 2H), 3.68-3.53 (m, 4H), 1.83-1.68 (m, 2H), 1.68-1.54 (m, 2H), 1.40 (s, 9H).

To a solution of tert-butyl 2-(2-bromophenyl)-3-((2-oxo-2-(quinolin-3-ylamino)ethyl)thio)-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF and triethylamine (5 equiv) and formaldehyde (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (0-30% MeOH in DCM) to provide 2-((3-(2-bromophenyl)-8-methyl-1,4,8-triazaspiro[4.5]deca-1,3-dien-2-yl)thio)-N-(quinolin-3-yl)acetamide. 1H NMR (400 MHz, DMSO-d6) δ 10.79 (s, 1H), 8.91 (d, J=2.5 Hz, 1H), 8.66 (d, J=2.5 Hz, 1H), 7.95 (ddd, J=12.8, 8.2, 1.3 Hz, 2H), 7.88-7.76 (m, 1H), 7.66 (ddd, J=8.4, 6.9, 1.5 Hz, 1H), 7.62-7.46 (m, 4H), 4.22 (s, 2H), 2.72-2.53 (m, 4H), 2.24 (s, 3H), 1.94 -1.64 (m, 4H).

Synthesis of Compound 35h 2-((8-methyl-3-(4-(trifluoromethyl)phenyl)-1,4,8-triazaspiro[4.5]deca-1,3-dien-2-yl)thio)-N-(quinolin-3-yl)acetamide methyl 2-amino-2-[4-(trifluoromethyl)phenyl]acetate hydrochloride was stirred in 28% ammonium hydroxide (Smug) solution for 96 hours resulting in the formation of 2-amino-2-(4-(trifluoromethyl)phenyl)acetamide as a white precipitate that was collected via filtration and used without further purification. To a solution of 2-amino-2-(4-(trifluoromethyl)phenyl)acetamide (1 equiv) in ethanol (0.1 M) was added tert-Butyl 4-oxo-1-piperidinecarboxylate (1 equiv) and the reaction mixture was heated to reflux for 12 hours. The reaction mixture was cooled to room temperature and concentrated under reduced pressure. The resulting residue was dissolved in DCM (0.1 M) and N-bromosuccinimide (1 equiv) was added. The reaction mixture was stirred for 8 hours and saturated sodium bicarbonate was added. The resulting mixture was extracted with DCM. The organics were dried, concentrated and purified by FCC (0-100%

EtOAc in hexanes) to provide tert-butyl 3-oxo-2-(4-(trifluoromethyl)phenyl)-1,4,8-triazaspiro[4.5]dec-1-ene-8-carboxylate. 1H NMR (400 MHz, DMSO-d6) δ 10.36 (s, 1H), 8.53 (d, J=8.1 Hz, 2H), 7.91 (d, J=8.1 Hz, 2H), 3.72-3.52 (m, 4H), 1.85-1.60 (m, 4H), 1.45 (s, 9H).

To a solution of tert-butyl 3-oxo-2-(4-(trifluoromethyl)phenyl)-1,4,8-triazaspiro[4.5]dec-1-ene-8-carboxylate (1 equiv.) in THF (0.1 M) was added Lawesson's reagent (0.6 equiv) and the reaction mixture was heated to 60° C. until the reaction was complete by TLC. The reaction mixture was concentrated onto silica gel and purified by flash column chromatography (0-100% EtOAc in hexanes) to provide tert-butyl 2-((2-oxo-2-(quinolin-3-ylamino)ethyl)thio)-3-(4-(trifluoromethyl)phenyl)-1,4,8-triazaspiro[4.5]deca-1,3-diene-8-carboxylate. 1H NMR (400 MHz, DMSO-d6) δ 12.66 (s, 1H), 8.58 (d, J=2.0 Hz, 1H), 8.27 (dd, J=8.4, 2.0 Hz, 1H), 7.80 (d, J=8.4 Hz, 1H), 3.83-3.71 (m, 2H), 3.61-3.45 (m, 2H), 1.89-1.66 (m, 4H), 1.45 (s, 9H).

To a solution tert-butyl 3-thioxo-2-(4-(trifluoromethyl)phenyl)-1,4,8-triazaspiro[4.5]dec-1-ene-8-carboxylate (1 equiv.) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layers were dried, concentrated and purified by flash column chromatography (0-100% EtOAc in hexanes) to provide tert-butyl 2-((2-oxo-2-(quinolin-3-ylamino)ethyl)thio)-3-(4-(trifluoromethyl)phenyl)-1,4,8-triazaspiro[4.5]deca-1,3-diene-8-carboxylate. 1H NMR (400 MHz, DMSO-d6) δ 10.80 (s, 1H), 8.97-8.88 (m, 1H), 8.79-8.58 (m, 1H), 8.19-8.08 (m, 1H), 8.08-7.86 (m, 4H), 7.77-7.52 (m, 2H), 4.29 (s, 2H), 3.72-3.46 (m, 4H), 1.82-1.67 (m, 2H), 1.61-1.43 (m, 2H), 1.38 (s, 9H).

To a solution of tert-butyl 2-((2-oxo-2-(quinolin-3-ylamino)ethyl)thio)-3-(4-(trifluoromethyl)phenyl)-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF and triethylamine (5 equiv) and formaldehyde (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (0-30% MeOH in DCM) to provide 2-((8-methyl-3-(4-(trifluoromethyl)phenyl)-1,4,8-triazaspiro[4.5]deca-1,3-dien-2-yl)thio)-N-(quinolin-3-yl)acetamide. 1H NMR (400 MHz, DMSO-d6) δ 10.80 (s, 1H), 8.94 (d, J=2.5 Hz, 1H), 8.67 (d, J=2.5 Hz, 1H), 8.09 (t, J=1.2 Hz, 1H), 8.01-7.91 (m, 2H), 7.91-7.83 (m, 2H), 7.67 (ddd, J=8.4, 6.9, 1.5 Hz, 1H), 7.59 (ddd, J=8.1, 6.8, 1.3 Hz, 1H), 4.29 (s, 2H), 2.70-2.57 (m, 4H), 2.23 (s, 3H), 1.98 —1.46 (m, 4H).

Synthesis of Compound 35i tert-butyl 2-(3,4-dichlorophenyl)-3-((quinolin-3-ylcarbamoyl)thio)-1,4,8-triazaspiro[4.5]deca-1,3-diene-8-carboxylate Methyl 2-amino-2-(3,4-dichlorophenyl)acetate hydrochloride was stirred in 28% ammonium hydroxide (5 mL/g) solution for 96 hours resulting in the formation of 2-amino-2-(3,4-dichlorophenyl)acetamide as a white precipitate that was collected via filtration and used without further purification. To a solution of 2-amino-2-(3,4-dichlorophenyl)acetamide (1 equiv) in ethanol (0.1 M) was added tert-Butyl 4-oxo-1-piperidinecarboxylate (1 equiv) and the reaction mixture was heated to reflux for 12 hours. The reaction mixture was cooled to room temperature and concentrated under reduced pressure. The resulting residue was dissolved in DCM (0.1 M) and N-bromosuccinimide (1 equiv) was added. The reaction mixture was stirred for 8 hours and saturated sodium bicarbonate was added. The resulting mixture was extracted with DCM. The organics were dried, concentrated and purified by FCC (0-100% EtOAc in hexanes) to provide tert-butyl 2-(3,4-dichlorophenyl)-3-oxo-1,4,8-triazaspiro[4.5]dec-1-ene-8-carboxylate. 1H NMR (400 MHz, DMSO-d6) δ 10.37 (s, 1H), 8.55 (d, J=1.9 Hz, 1H), 8.29 (dd, J=8.4, 1.9 Hz, 1H), 7.82 (d, J=8.4 Hz, 1H), 3.70-3.51 (m, 4H), 1.81-1.58 (m, 4H), 1.44 (s, 9H).

To a solution of tert-butyl 2-(3,4-dichlorophenyl)-3-oxo-1,4,8-triazaspiro[4.5]dec-1-ene-8-carboxylate (1 equiv.) in THF (0.1 M) was added Lawesson's reagent (0.6 equiv) and the reaction mixture was heated to 60° C. until the reaction was complete by TLC. The reaction mixture was concentrated onto silica gel and purified by flash column chromatography (0-100% EtOAc in hexanes) to provide tert-butyl 2-(3,4-dichlorophenyl)-3-thioxo-1,4,8-triazaspiro[4.5]dec-1-ene-8-carboxylate. 1H NMR (400 MHz, DMSO-d6) δ 12.66 (s, 1H), 8.58 (d, J=2.0 Hz, 1H), 8.27 (dd, J=8.4, 2.0 Hz, 1H), 7.80 (d, J=8.4 Hz, 1H), 3.83-3.71 (m, 2H), 3.61-3.45 (m, 2H), 1.89-1.66 (m, 4H), 1.45 (s, 9H).

To a solution tert-butyl 2-(3,4-dichlorophenyl)-3-thioxo-1,4,8-triazaspiro[4.5]dec-1-ene-8-carboxylate (1 equiv.) in DCM (0.1 M) was 2-bromo-N-(quinolin-3-yl)acetamide (1 equiv.) and triethylamine (3 equivalents). The reaction mixture was stirred for 12 hours at room temperature. The reaction mixture was diluted with DCM and washed with saturated aqueous sodium bicarbonate. The organic layers were dried, concentrated and purified by flash column chromatography (0-100% EtOAc in hexanes) to provide tert-butyl 2-(3,4-dichlorophenyl)-3-((2-oxo-2-(quinolin-3-ylamino)ethyl)thio)-1,4,8-triazaspiro[4.5]deca-1,3-diene-8-carboxylate. 1H NMR (400 MHz, DMSO-d6) δ 10.80 (s, 1H), 8.97-8.88 (m, 1H), 8.79-8.58 (m, 1H), 8.19-8.08 (m, 1H), 8.08-7.86 (m, 4H), 7.77-7.52 (m, 2H), 4.29 (s, 2H), 3.72-3.46 (m, 4H), 1.82-1.67 (m, 2H), 1.61-1.43 (m, 2H), 1.38 (s, 9H).

To a solution of tert-butyl 2-(3,4-dichlorophenyl)-3-((2-oxo-2-(quinolin-3-ylamino)ethyl)thio)-1,4,8-triazaspiro[4.5]deca-1,3-diene-8-carboxylate (1 equiv) in DCM (0.1 M) was added 4 M HCl in dioxane (2 equiv.) and the reaction mixture was stirred at room temperature for 5 hours. The reaction mixture was concentrated. The resulting residue was taken up in THF and triethylamine (5 equiv) and formaldehyde (3 equiv) were added followed by NaBH(OAc)3 (3 equiv) and the reaction mixture was stirred for 12 hours at room temperature. The reaction mixture was concentrated, taken up in EtOAc and washed with saturated aqueous sodium bicarbonate. The organics were dried, concentrated and purified by flash column chromatography (0-30% MeOH in DCM) to provide tert-butyl 2-(3,4-dichlorophenyl)-3-((quinolin-3-ylcarbamoyl)thio)-1,4,8-triazaspiro[4.5]deca-1,3-diene-8-carboxylate. 1H NMR (400 MHz, DMSO-d6) 6 10.80 (s, 1H), 8.94 (d, J=2.5 Hz, 1H), 8.67 (d, J=2.5 Hz, 1H), 8.09 (t, J=1.2 Hz, 1H), 8.01-7.91 (m, 2H), 7.91-7.83 (m, 2H), 7.67 (ddd, J=8.4, 6.9, 1.5 Hz, 1H), 7.59 (ddd, J=8.1, 6.8, 1.3 Hz, 1H), 4.29 (s, 2H), 2.70-2.57 (m, 4H), 2.23 (s, 3H), 1.98-1.46 (m, 4H).

Pharmacokinetics Studies

Example 44—Interaction Between Purified EGFR Kinase Domain and Disruptin

Figure 2:
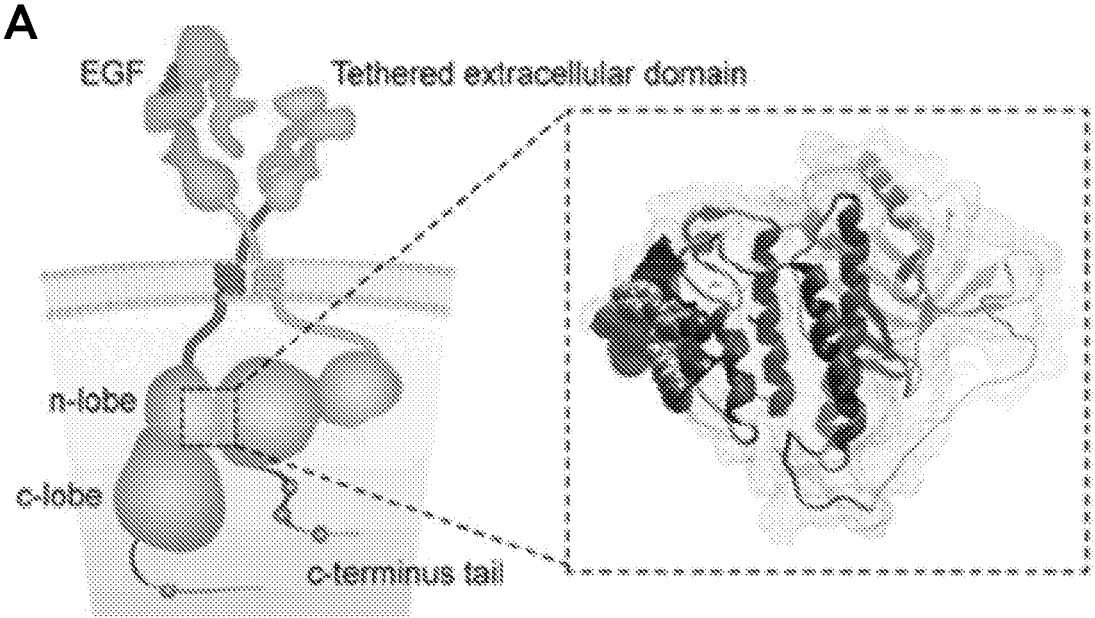
FIG. 2 shows (A) a schematic diagram of an asymmetric, active dimer of EGFR. One EGF-bound monomer of EGFR is sufficient to induce dimerization. A model of Disruptin bound to the c-lobe of EGFR (PDB Code: 2RFD) is shown in the inset and (B) hypothesized interaction between purified EGFR kinase domain and Disruptin.
Figure 2:

WT-EGFR kinase domain (aa696-1022, active kinase) was expressed and purified from SF9 insect cells. 100 ng pure EGFR was incubated with biotin-conjugated Disruptin, and the bound EGFR was captured using CaptAvidin beads after washing with citrate buffer. Specificity of this interaction was confirmed by co-incubating this reaction with an increasing amount of non-biotinylated Disruptin. The bound EGFR protein was released in Laemmli buffer and resolved by SDS page. Disruptin-bound EGFR was quantified using ImageJ software and shown below the blot. Competitive inhibition of Disruptin-EGFR binding by cold-Disruptin indicates that Disruptin binds directly to EGFR (see FIG. 2B).

Figure 3:
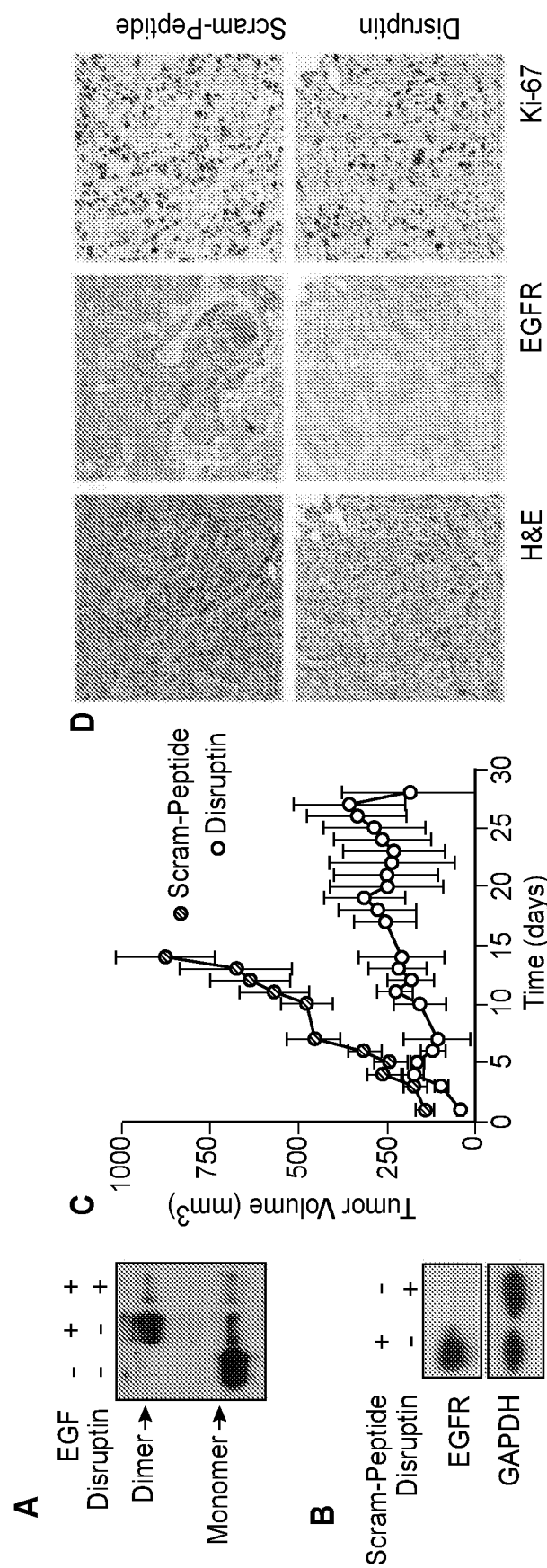
FIG. 3 shows (A) the effect of Disruptin treatment on EGF induced dimerization in NCI-H1975 cells; (B) the effect of Disruptin on its target EGFR in NCI-H1975 xenografts; (C) the efficacy of Disruptin in vivo; and (D) the long term effect of treatment on tumor histology, EGFR expression, and mitotic index (measured by Ki-67 score).
Figure 4:
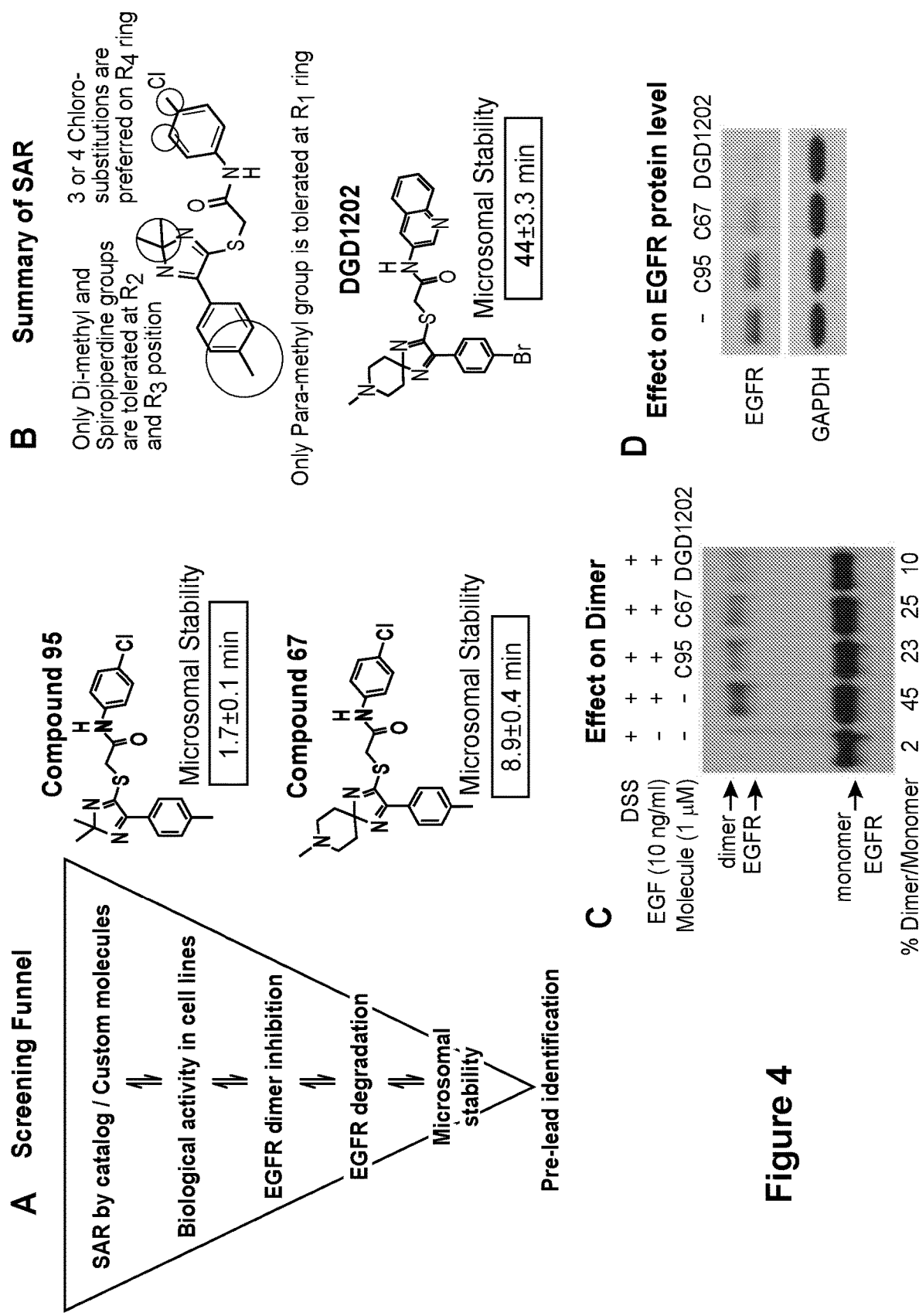
FIG. 4 shows (A) the process for pre-screening lead compounds, and the structures of two pre-lead compounds, C95 and C67; (B) the resulting SAR combined with microsomal stability (shown in the blue box), as well as the structure of the most selectively effective molecule, named Compound 8C; (C) the effect of two pre-leads and Compound 8C on EGF-stimulated EGFR dimerization in an erlotinib-resistant NCI-H1975 lung cancer cell line as described in FIG. 3A (lysates were prepared and immunoblotted with anti-EGFR antibodies); and (D) the effect of selected three lead molecules (1 µM) on steady-state EGFR protein as assessed at 24 hours post-treatment.

Example 45—Effect of Disruptin Treatment on EGF Induced Dimerization in NCI-H1975 Cells NCI-H1975 cells were treated for 1 hour with 10 μM Disruptin and an additional 30 minutes with EGF (30 ng/ml) and 30 minutes with disuccinimidyl suberate (DSS, 150 μM) to cross-link interacting proteins. Lysates were prepared and immunoblotted with anti-EGFR antibodies. (see FIG. 3A).

Example 46—Effect of Disruptin On Its Target EGFR in NCI-H1975 Xenografts

Mice bearing NCI-H1975 xenografts were injected with Disruptin (10 mg/kg, i.p.) on days 1 and 2. On day 3 tumors were removed and prepared for immunoblotting (see FIG. 3B). The effect of Disruptin on NCI-H1975 xenografts was assessed after treatment with Disruptin (10 mg/kg, i.p.) injections on two consecutive days (Monday-Tuesday) for two weeks. Tumor volume was plotted for each treatment condition. Scrambled-peptide was used as control (see FIG. 3C). The long term effect of treatment on tumor histology, EGFR expression, and mitotic index (measure by Ki-67 score) was assessed by immunostaining the tumors after 2 weeks of treatment (see FIG. 3D).

Example 47—Development of Compound 8C and Confirmation of Biological Activity

Figure 9:
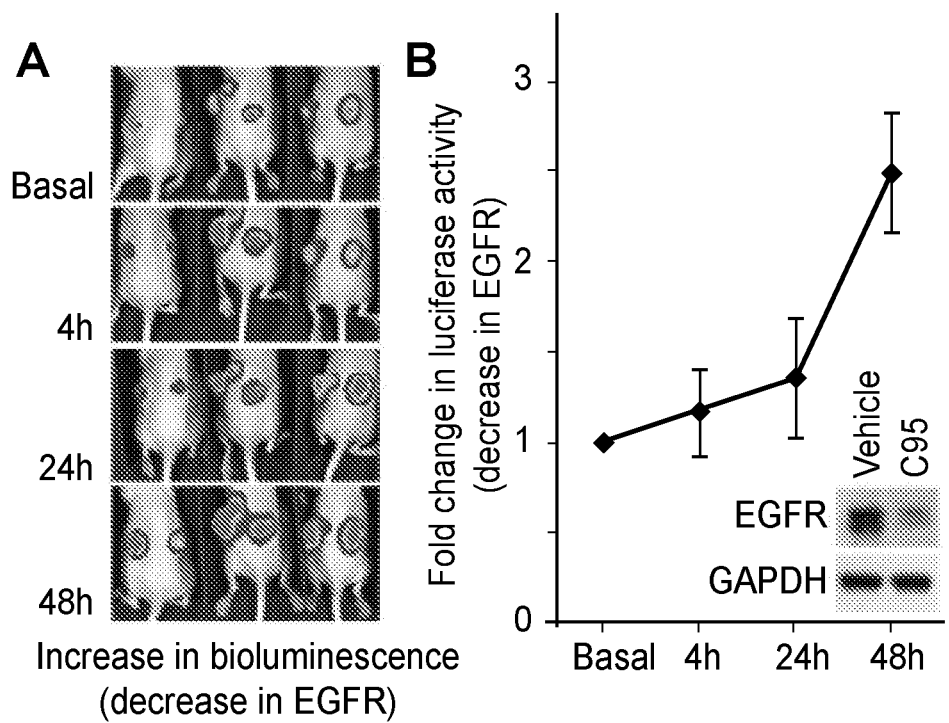
FIG. 9 shows (A) the basal bioluminescence and effect of pre-lead compound 95 on different time points in NCI-H1975 xenograft-bearing mice; and (B) the quantified and plotted change in bioluminescence.

Disruptin was shown to be effective against a TKI (erlotinib) resistant NCI-H1975 xenograft model (see FIGS. 3A-D) (14). However, due to poor PK and other challenges in the development of peptide drugs, a drug-discovery program was undertaken to develop a small molecule that has a similar mechanism of action but superior pharmacokinetics (see FIGS. 4A-D). Based on the active EGFR dimer interface, using a virtual screen, commercial library acquisition, and custom synthesis a novel series of molecules was developed that includes pre-lead compounds 95 (C95) and 67 (C67) (see FIGS. 4A-D). Both of these pre-lead molecules are active in vivo against the erlotinib-resistant NCI-H1975 xenograft model. To test the in vivo activity of EGFR dimer inhibition, TKI resistant NCI-H1975 EGFR reporter cells were used. These tumor xenografts show induction of bioluminescence upon loss of EGFR activity (47). A single injection of 100 mg/kg C95 led to a 2.5-fold induction of the EGFR reporter that lasted 48 hr. (see FIG. 9). It was confirmed that the effect of C95 treatment on reduction in EGFR level correlates with change in bioluminescence. These data indicate that agents that can induce degradation of EGFR can be effective in TKI resistant tumors.

Figure 10:
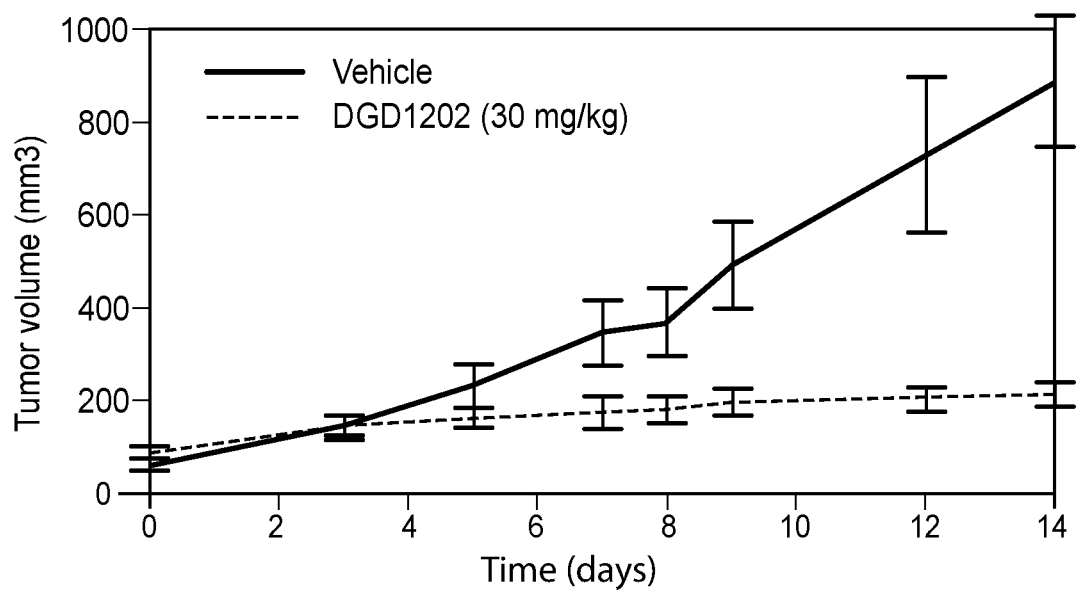
FIG. 10 shows the change in the average tumor volume with time of nude mice bearing UMSCC74B, a head and neck tumor model (~100 $mm^2$) and treated with Compound 8C (30 mg/kg, daily for one week) or with vehicle (5% DMSO in PBS). Each group had at least 5 mice. Tumor volume and body weight was recorded 3-4 times a week, and is plotted. The average loss in body weight during treatment was less than 10%. Error bar represents standard error of the mean.

Compound 8C is approximately 20 times more stable compared to its pre lead (C95) in both mouse and human liver microsomes. Efficacy testing of Compound 8C in UMSCC74B, an EGFR driven, aggressive tumor model of the head and neck. Tumor bearing mice were treated with 30 mg/kg dose daily (Monday-Friday) for one week. This dose was selected based on single dose PK profile (see FIG. 8A). This treatment was safe and produced significant tumor growth delay (see FIG. 10).

Figure 11:
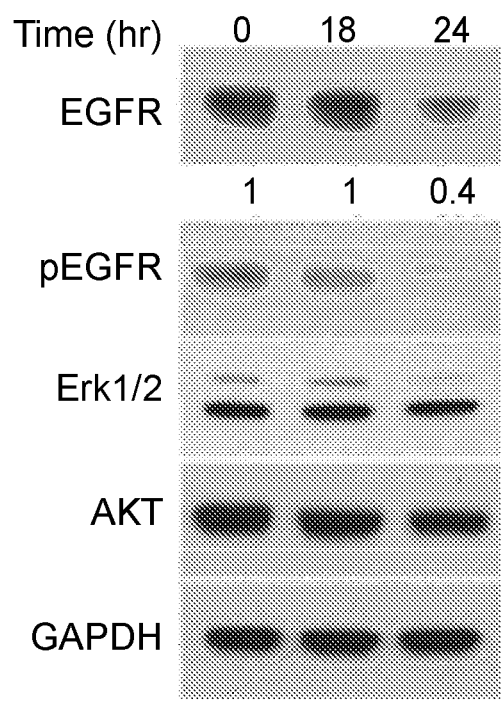
FIG. 11 shows the effect of Compound 8C in an osimertinib resistant tumor model. Nude mice with osimertinib resistant Ba/F3 ascites tumor were treated with either vehicle, osimertinib or Compound 8C. The effect of treatment on EGFR, pEGFR and other molecules was determined by immunoblotting.
Figure 12:
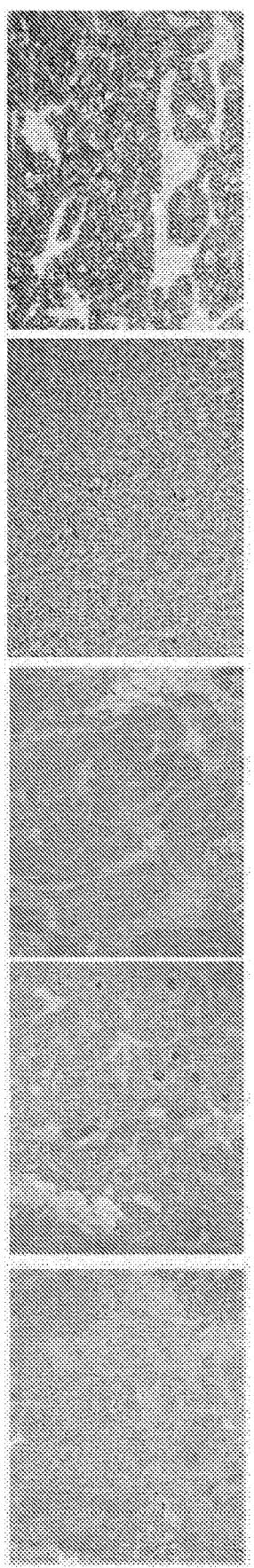
FIG. 12 shows the pathological assessment of FFPE-lung PDXs in a primary tumor, $1^{st}$ and $2^{nd}$ xenograft of UMLCA7 and analysis of EGFR protein expression using IHC in two other PDXs. Note the abundant EGFR expression in the squamous cell carcinoma (UMLT16) but not in the large cell carcinoma (UMLT14) PDX sample (20X).

Osimertinib resistant Ba/F3 cells mediated ascites (via i.p. injection of cells) and solid tumor models (via s.c. injection of cells) in nude mice were also used for efficacy studies. Initial studies were performed in the ascites model and the effect of Compound 8C was compared to an equal dose of osimertinib (30 mg/kg). Although treatment was initiated only after the tumor burden became high, a single 30 mg/kg dose of Compound 8C prolonged life in these mice compared to the osimertinib treated group (p=0.072, data not shown). The effect of treatment on EGFR was confirmed in the cells collected from the same mouse before treatment, 18 hours and 24 hours post-treatment (see FIG. 11).

Example 48—Direct Interaction Between EGFR Kinase Domain and Compound 8C

To determine if Compound 8C competes for the same binding site on EGFR, Biotin-Disruptin-Avidin coupled beads were incubated with purified EGFR in the presence or absence of Compound 8C for 15 minutes at 37° C. The agarose beads were spun down, and the non-specific protein removed by washing in citrate buffer. The bound protein was released in Laemmli buffer and resolved by SDS page. Competitive inhibition of Disruptin-EGFR binding by the Compound 8C suggests a similar mechanism of action of this molecule (see FIG. 5A).

The effect of Compound 8C on thermal stability of purified EGFR was confirmed by thermal stability assay. 100 ng of purified EGFR was incubated with either DMSO or Compound 8C (10 μM) for 30 minutes at 4° C. The samples were subjected to heat inactivation (20 to 44° C.) for 3 minutes. The soluble fraction was separated from aggregate by centrifugation at 13,000 RPM at 4° C. for 10 minutes. About 20 ng of soluble protein was resolved on 4-12% bis-tris gel and blotted with anti-EGFR antibodies. The EGFR band intensity as quantified by ImageJ software and plotted (see FIG. 5B). The effect of Compound 8C concentration on thermal stability of EGFR at 44° C. was determined in the presence of 0 to 10 μM Compound 8C. The soluble fraction of EGFR was quantified and plotted as described above (see FIG. 5C).

Figure 5:
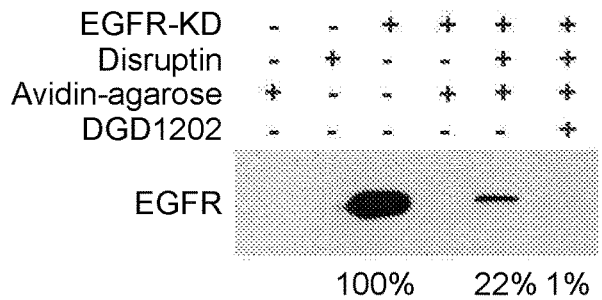
FIG. 5 shows (A) Compound 8C competes with Disruptin for EGFR binding; (B) the effect of Compound 8C on the thermal stability of purified EGFR as confirmed by thermal stability assay; and (C) the effect of Compound 8C concentration on thermal stability of EGFR at 44° C. in the presence of 0 to 10 µM Compound 8C.
Figure 5:
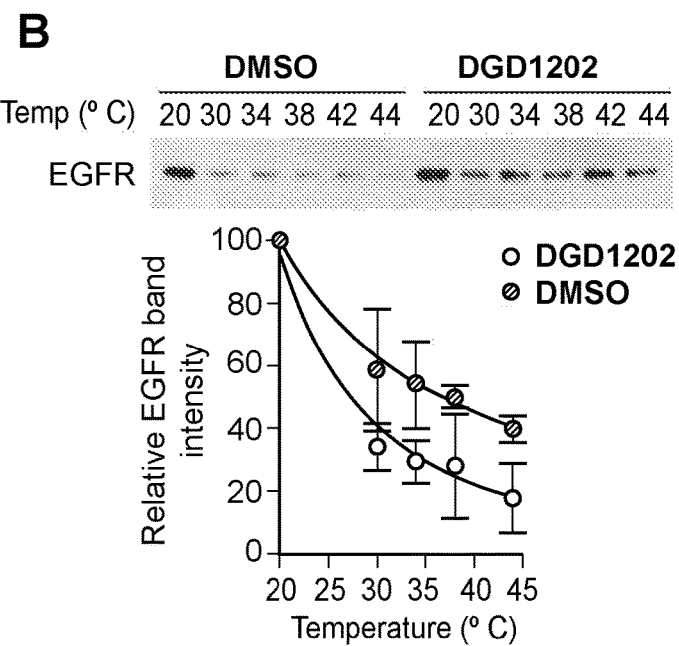
Figure 5:
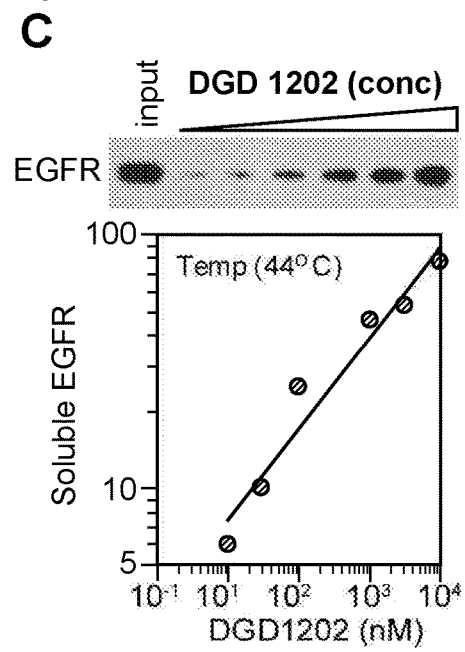
Figure 6:
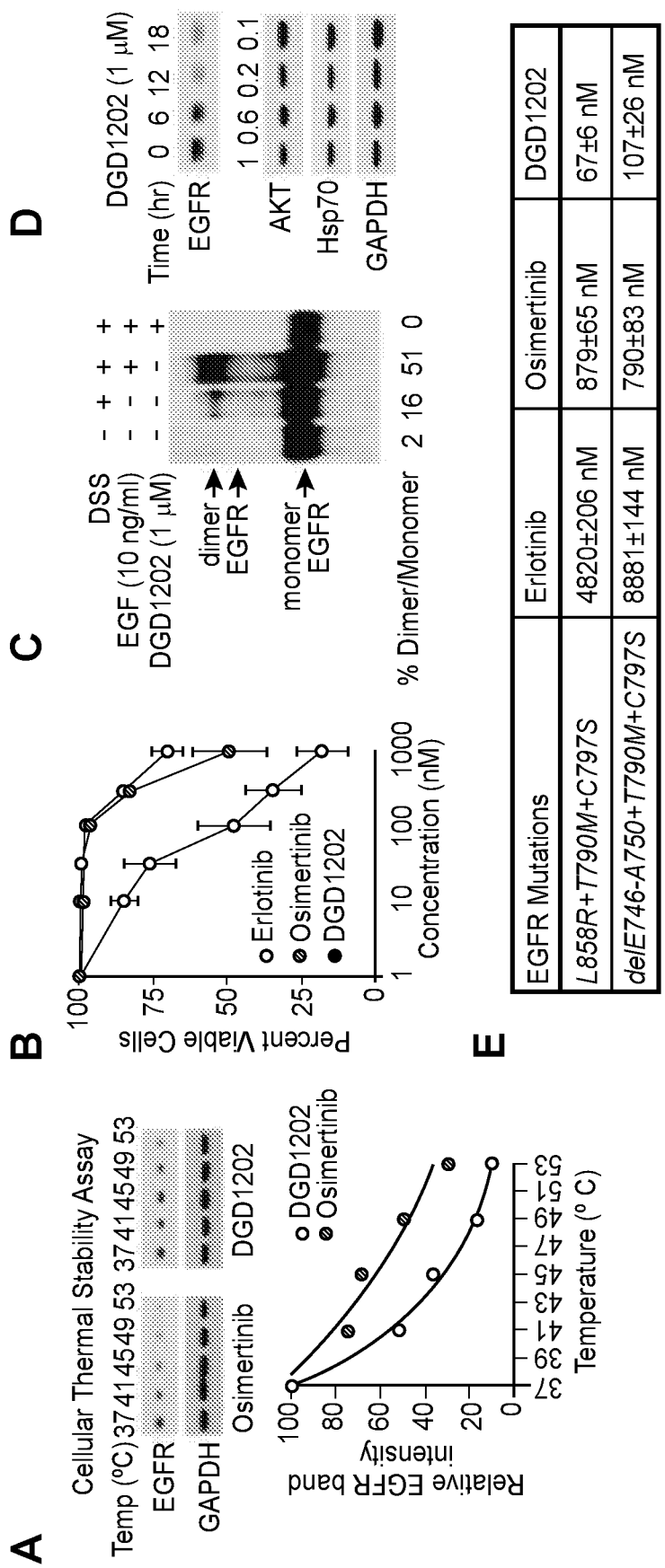
FIG. 6 shows the (A) effect of Compound 8C on EGFR thermal stability in a whole cell lysate from Ba/F3-AZD cells;. (B) potency of Compound 8C as determined against osimertinib-resistant Ba/F3 cells expressing specific EGFR mutations; (C) the effect of Compound 8C on EGF induced EGFR dimerization as described in FIG. 3A; (C-D). effect of Compound 8C treatment on EGFR induced dimer and EGFR protein level; (E) $IC_{50}$ values in response to erlotinib, osimertinib and Compound 8C as tabulated from two osimertinib resistant Ba/F3 cell lines.

The preliminary data show that Compound 8C is likely to bind to the same site on the EGFR molecule as Disruptin (see FIG. 5A) and can thermally stabilize wild-type as well as osimertinib resistant (C797S) EGFR. As shown in FIGS. 5B and 5C, Compound 8C incubation with purified wild-type EGFR kinase domain shifts the melting curve, suggesting an interaction between EGFR and Compound 8C . To determine the effect of Compound 8C on osimertinib resistant EGFR mutant, a cell-based assay was used. Osimertinib or Compound 8C was incubated with the whole cell lysate prepared from Ba/F3 (C797S-EGFR) cells. The aliquots were heated to different temperatures in the presence of either DMSO, 10 μM osimertinib or Compound 8C. After cooling, the samples were centrifuged, and the soluble protein fraction was collected and resolved using immunoblotting with anti-EGFR antibodies (see FIG. 6A). Osimertinib was effective in shifting the melting temperature of purified WT-EGFR (see FIG. 5B), but it had minimal effect on the C797S mutated EGFR protein (see FIG. 6A). As expected, Compound 8C was effective in shifting the melting temperature of osimertinib resistant EGFR. These data suggest a potential interaction between Compound 8C with EGFR, even in EGFR-C797S.

Based on these data it was hypothesized that Compound 8C will remain effective in cells that have acquired resistance to osimertinib due to C797S mutation. Using these isogenic 6-Ba/F3 cell types (that includes TKI sensitive and resistant cells, Table I) it was demonstrated that Compound 8C remains active in the nanomolar range in each cell line. This is expected from this class of agents as their action is independent of EGFR kinase mutations. The effect of Compound 8C on inhibition of EGF-induced EGFR dimerization and protein expression was also confirmed in all these cells. The data shown are from the osimertinib resistant Ba/F3 cells with a C797S mutation (see FIGS. 6B-6E).

Figure 7:
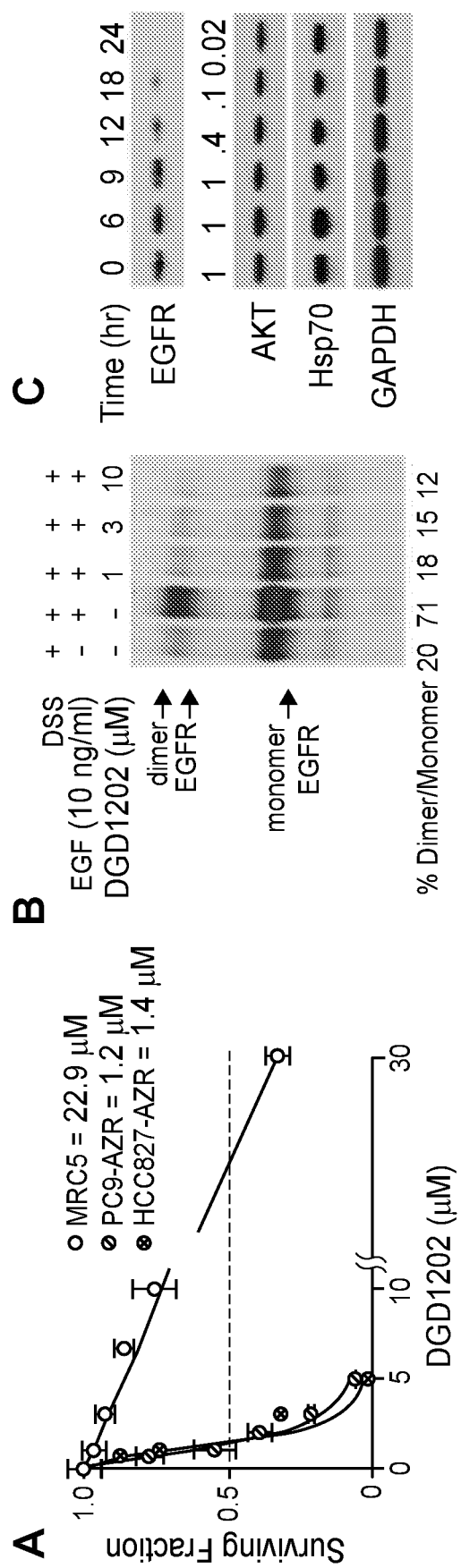
FIG. 7 shows (A) the specificity and potency of Compound 8C determined against a panel of osimertinib-resistant cells and compared with normal lung fibroblasts (MRCS) using the clonogenic survival assay; (B) the effect of Compound 8C concentration on EGF induced EGFR dimerization in osimertinib resistant PC9 cells as described in FIG. 6; (C) the effect of Compound 8C treatment on EGFR induced dimer and EGFR protein level in PC9-AZR cells.

Example 49—Validation of Selective Activity of Compound 8C in Lung Cancer Cell Lines To test the selectivity of Compound 8C, osimertinib resistant lung cancer cell lines (PC9-AZR and HCC827-AZR), along with normal lung fibroblasts (MRCS), were treated with different concentrations, and cell survival was determined using a clonogenic survival assay (see FIG. 7A and Table 3, below). These preliminary data suggest that Compound 8C selectively kills cancer cells that are driven by EGFR. It was determined if the response to Compound 8C correlates with inhibition of EGF-induced dimerization and degradation of EGFR. For this, PC9-AZR cells were treated for 1 hour with 1 μM Compound 8C and an additional 30 minutes with EGF (30 ng/ml) and 30 minutes with disuccinimidyl suberate (DSS, 150 μM) to cross-link interacting proteins. Lysates were prepared and immunoblotted with anti-EGFR antibodies. FIG. 7B shows that 1 μM Compound 8C can inhibit EGFR dimerization and induce degradation of EGFR. Overall, these results confirm the findings from the Ba/F3 cells.

Example 50—Viability assay

The viability of cells upon treatment was assessed by CellTiter-Blue® reagent following the manufacturer's protocol in RKO, UM10B, UM1, MCR5, and UMCC92 cells. Briefly, 10,000 cells were plated in 96-well plate in quadruplets. One day after seeding, cells were treated with a range of concentrations (0.1 to 30 micromolar). 3-days post-treatment, cells were incubated with the CellTiter-Blue® reagent for 4 hr. Only the viable cells convert the redox dye (reszurin) into a fluorescent product (resofurin). The emission of fluorescence (excitation 560 nM) was measured at 590 nM. The $IC_{50}$ value was calculated as the mean concentration of compounds required to inhibit cell proliferation as measured by the fluorescence at 590 nM by 50 percent compared to the vehicle-treated controls. Results are presented in Table 3 and Table 4, below.

TABLE 3

| | Cell Titer Blue | | | | | | |
|---|---|---|---|---|---|---|---|
| ID #% | Cell viable (24 hrs) | Conc (μM) | \multicolumn{5}{c}{Clonogenic $IC_{50}$ (μM)} | | | | |
| | | | RKO | UM108 | UM1 | MCR5 | UMCC92 |
| 13 | 59.4 | 30 | 25.2 | 6.9 | | 335 | |
| 14 | 99.7 | 30 | | 465 | | 28 | |
| 15 | 119 | 30 | 50.7 | 17.2 | | 37.0 | |
| 16 | 122 | 30 | 43.9 | 38.0 | | 1316 | |
| 17 | 109 | 30 | | 44.0 | | 61.0 | |
| 18 | 48 | 30 | 6.7 | 2.5 | | 25.9 | |
| 19 | 68 | 7.5 | 3.1 | 2.6 | | 4.1 | |
| 20 | 54 | 15 | 1.8 | 4.0 | | 2.4 | |
| 21 | 73 | 15 | 85 | 4.3 | | 0.3 | |
| 22 | 55 | 7.5 | 0.8 | 0.3 | | 2.3 | 0.2 |
| 23 | 103 | 30 | 2.2 | 5.3 | | 5.4 | |
| 24 | 72 | 30 | 5.4 | 4.3 | | 7.6 | |
| 25 | 78 | 30 | 3.7 | 2.6 | | 69.3 | 2.1 |
| 26 | 88 | 30 | 2.6 | 1.1 | | 1.3 | |
| 27 | 76 | 30 | 19 | 8.8 | | 4.1 | |
| 28 | 15 | 15 | 6.5 | 1.0 | | 1.3 | |
| 29 | 89 | 30 | 1.4 | 0.7 | | 3.3 | |
| 8A | 58 | 30 | 8.8 | | 1.0 | | |
| 8B | 50 | 15 | 5.3 | | 0.8 | | |
| 8C | 68 | 3.75 | 1.6 | | 0.5 | 18.6 | 0.2 |
| 8D | 64 | 7.5 | 7.3 | | 0.8 | | |
| 8E | 84 | 30 | 14.1 | | 1.9 | | |
| 8F | 62 | 30 | 17.4 | | 1.0 | | |
| 86 | 40 | 30 | 8.5 | | 1.6 | | |
| 10 | 81 | 30 | 21.8 | | 1.7 | | |
| 11 | 52 | 30 | 26 | | 1.3 | | |
| 12 | 78 | 30 | 34 | | 1.2 | | |
| 30 | 112 | 30 | | 6.5 | | 73 | |
| 31 | 99 | 30 | | 7.7 | | 7.8 | |
| 32 | 104 | 30 | 8 | 4 | | 15 | |
| 3 | 70 | 30 | 9.8 | | 7.8 | | |
| 4 | 61 | 15 | 7.6 | | 1.0 | | |
| 5 | 60 | 15 | 11.6 | | 0.9 | | 34 |

TABLE 4

| ID # | BAF3-EGRF LTC IC50 μM |
|---|---|
| 33A | 0.45 |
| 33B | 0.82 |
| 33C | 0.79 |
| 33D | 0.71 |
| 33E | 0.61 |
| 33F | 0.50 |
| 336 | 2.6 |
| 33H | 0.85 |
| 33I | 1.75 |
| 33J | 1.95 |
| 33K | 2.20 |
| 33L | 2.85 |
| 34A | 2.00 |
| 34B | 2.60 |
| 34C | 6.50 |
| 34D | 1.42 |
| 34E | 4.80 |
| 34F | 0.70 |
| 35A | 0.56 |
| 35B | 0.80 |
| 35C | 0.55 |
| 35D | 0.28 |
| 35E | 1.13 |
| 35F | 2.55 |
| 356 | 5.95 |
| 35H | 1.85 |
| 35I | 1.57 |

Example 51—In Vivo harmacokinetics of Compound 8C in tumor and Plasma

Figure 8:
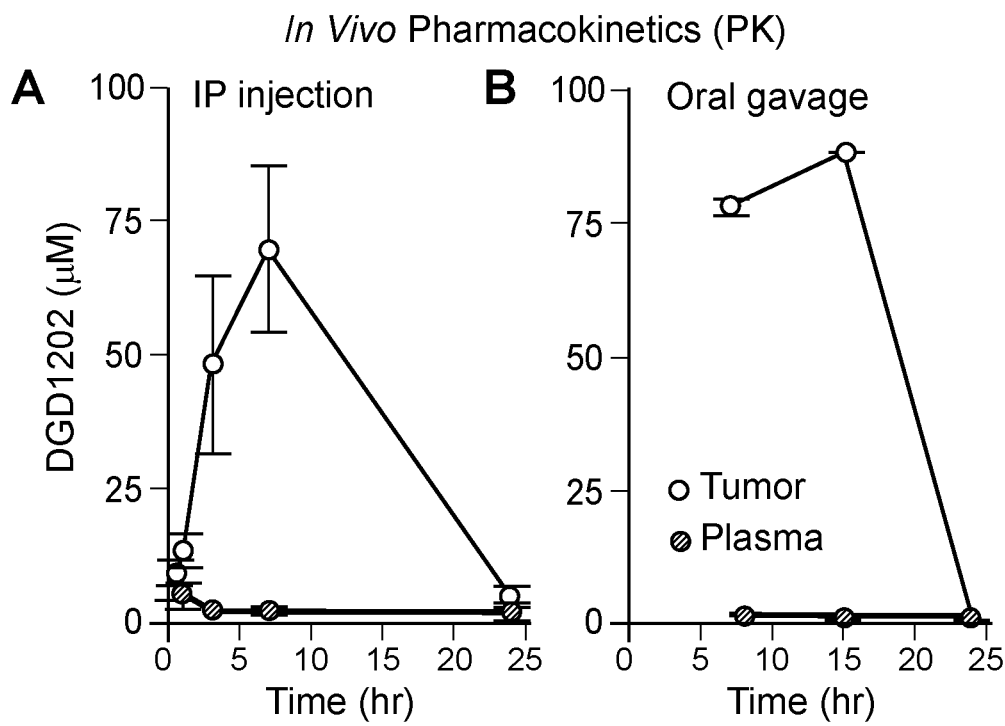
FIG. 8 shows (A) the pharmacokinetics of a single 100 mg/kg dose of Compound 8C given intraperitoneally in nude mice bearing human NCI-H1975 tumor xenografts (>150 $mm^3$); and (B) the pharmacokinetics of a single 100 mg/kg dose of Compound 8C given by oral gavage in nude mice bearing human NCI-H1975 tumor xenografts (>150 $mm^3$).

A short-term PK study administering the agent by i.p. injection revealed that Compound 8C selectively accumulates in the tumor in spite of the fact that it is rapidly cleared from the plasma (see FIGS. 8A and 8B). The peak concentration of Compound 8C achieved in the tumor (69.7±15.68 µM for ≥7 hours) is far greater than the concentration needed to kill 99% of TKI resistant tumor cells. The $IC_{50}$ and $IC_{90}$ for PC9-AZR, and HCC827-AZR, range from ~1.5 to ~4 µM (see FIG. 7A). It is interesting to note that the peak plasma concentration was 5.4±1.5 µM for 30 minutes. The plasma half-life of Compound 8C is 7.96 hours, but the half-life in the tumor is much greater than 24 hours (see FIG. 8A). Prolonged drug accumulation in tumors despite rapid systemic clearance is ideal for therapeutic use. The data at the 24 hour time point indicate that the agent may be suitable for daily administration. After observing selective accumulation of Compound 8C in tumors injected i.p., it was determined if Compound 8C is orally available. For oral administration, Compound 8C was formulated in 20% tween80 in PBS (v/v) after brief sonication. Mice received 100 mg/kg by oral gavage. The concentrations of Compound 8C in tumor and plasma samples at 7 hours, 15 hours and 24 hours were determined and are plotted in FIG. 8B.

For intraperitoneal injection Compound 8C was formulated at 10 mg/mL in PBS with 5% DMSO by adjusting the pH to 5.5. For oral administration, a homogenous suspension was prepared in 20% tween 80 upon brief sonication. Initially, a single 100 mg/kg dose of Compound 8C was given i.p. (FIG. 8A) or gavaged into nude mice bearing human NCI-H1975 tumor xenografts (>150 mm3) (FIG. 8B). Mice were euthanized at time 0, 30 minutes, 1 hour, 3 hours, 7 hours, 15 hours, and at 24 hours. Tumor and plasma samples were collected. In case of mice orally gavaged, plasma and tumor samples were collected only at 7 hours, 15 hours and at 24 hours. The concentration of Compound 8C in plasma and tumor was determined and the resulting data are plotted in terms of molar concentration.

Example 52—Validation of EGFR Reporter in Vivo

This approach was validated with compound C95. Briefly, once the tumors reached the size of about 100 mm³, mice were imaged to obtain the basal bioluminescence and effect of pre-lead compound 95 on different time points (see FIG. 9A). Change in Bioluminescence was quantified and plotted (see FIG. 9B). Finally, the effect of treatment on EGFR protein level was confirmed by immunoblotting after 48 hours of treatment.

Example 53—In Vivo Activity of Compound 8C

Nude mice bearing either UMSCC74B (-100 mm²) were treated with (30 mg/kg, daily for one week) or with vehicle (5% DMSO in PBS). Each group had at least 5 mice. Tumor volume and body weight was recorded 3-4 times a week, and change in the average tumor volume with time is plotted. The average loss in body weight during treatment was less than 10%. Error bar represents standard error of the mean.

For the Compound 8C treatment group, day 0 is defined as the first day of treatment. In vehicle control mice, day 0 was defined as the day when the tumor volume was closest to the mean tumor volume in Compound 8C treatment groups on the day of treatment initiation. To assess whether tumor volume growth rates differed by treatment, mixed effect models were fit with random intercept terms at the mouse levels to account for correlated outcomes over time within a tumor and between 2 tumors within a mouse. Monotherapy elicited a significant reduction in tumor growth rate after one week of dosing (see FIG. 10). Tumor growth rates were significantly lower in the Compound 8C treatment group compared to the time-matched control group (p=0.013) and the overall control group (p<0.001).

Example 54—Effect of Compound 8C in an Osimertinib Resistant Tumor Model

To test the activity of Compound 8C against osimertinib resistant EGFR driven tumors, an ascites tumor model was developed using Ba/F3-AZR cells (L858R+T790M+C797S-EGFR) as reported previously (65). 5 million, BA/F3-AZR cells were injected via i.p. injection into 6-week old female nude mice. Mice developed an ascitic tumor, and a mean survival time of 20 days was observed. To test the efficacy of Compound 8C compared to osimertinib, injected 15 mice were injected with Ba/F3-AZR cells. 18 days after injection of tumor cells, mice were randomized into three groups. Mice were treated with vehicle, a single oral dose of 30 mg/kg osimertinib, or 30 mg/kg Compound 8C via i.p. injection. The health of mice was monitored and mice were euthanized according to ULAM end-stage guidelines. Although treatment was initiated after the tumor burden became high, a single 30 mg/kg dose of Compound 8C prolonged life in these mice compared to the osimertinib treated group. There was no difference noted between vehicle control and osimertinib treatment group. The difference between osimertinib and Compound 8C was calculated using log-rank test (p=0.072). To test the effect of treatment on target, tumor cells were collected from one mouse before treatment, 18 hours, and 24 hours post-treatment. Cells were washed in PBS and processed as described in FIG. 3, and immunoblotting results showing the effect of treatment on EGFR, pEGFR and other molecules are given in FIG. 11.

Example 55—Preliminary Safety Test of Compound 8C in a Mouse Model

A preliminary test on the safety of a daily dose of 30 mg/kg for one week was performed using C57BL6 mice. The overall health and weight of a group of 6 mice was monitored during treatment. A modest loss of 3.5±2.4% body weight after one week of treatment was observed, but mice fully recovered the weight 2-days after treatment cessation.

Example 56: NCI 60 Cell Line Screen

The activity of Compound 8C was tested against 60 different human tumor cell lines at the National Cancer Institute, using the standard NCI 60 screening protocol. The percent growth inhibition for the top performing cell lines is given in Table 5, below.

TABLE 5

| Panel | Cell Line | Percent Growth |
| --- | --- | --- |
| Melanoma | SK-MEL-5 | −96.2 |
| Colon Cancer | HCT-116 | −90.7 |
| Melanoma | M14 | −83.8 |
| Renal Cancer | 786-0 | −81.7 |
| Melanoma | UACC-62 | −78.9 |
| Melanoma | LOX IMVI | −78.5 |
| Colon Cancer | COLO 205 | −76.2 |
| Melanoma | MALME-3M | −75.5 |
| Melanoma | SK-MEL-28 | −70.1 |
| Colon Cancer | HT29 | −67.1 |
| Leukemia | K-562 | −61.5 |

TABLE 5-continued

| Panel | Cell Line | Percent Growth |
|---|---|---|
| Melanoma | UACC-257 | −61.2 |
| Colon Cancer | HCC-2998 | −51.3 |
| Breast Cancer | MDA-MB-468 | −43.8 |
| Breast Cancer | MCF7 | −42.7 |
| Leukemia | HL-60(TB) | −40.7 |
| Breast Cancer | MDA-MB-231/ATCC | −40.5 |

Figure 13:
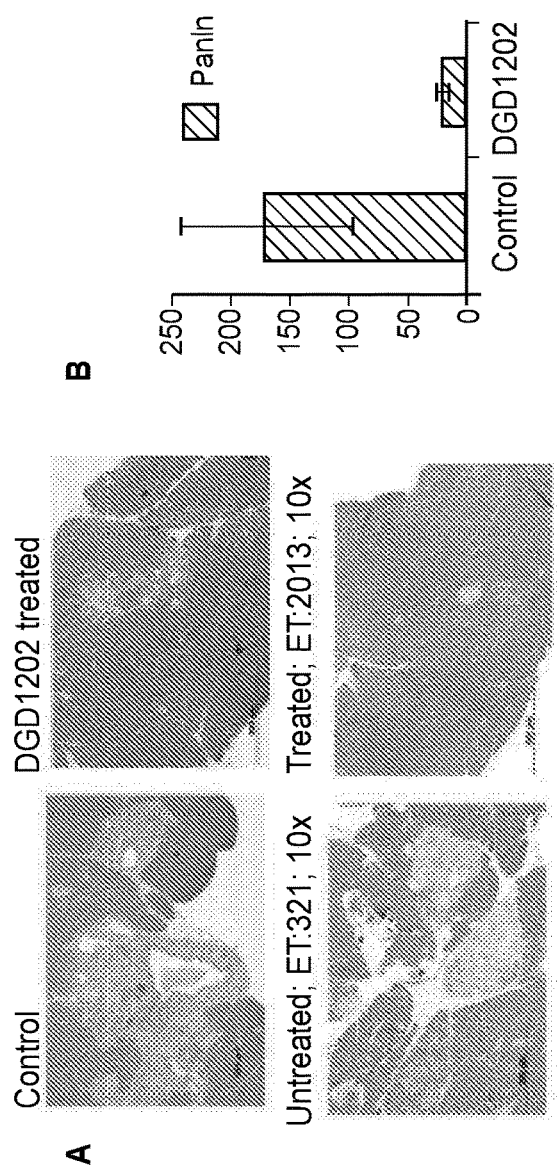
FIG. 13 shows that treating a mouse pancreatic cancer model with Compound 8C showed significantly reduced propensity for developing PanIn (Pancreatic Intraepithelial Neoplasia), a type of pancreatic duct lesion. A—histological examination of pancreatic tissue shows significantly less lesion involvement in treated mice compared to a control, which is quantified in B.

Example 57: Effect of Compound 8C in a Pancreatic Tumor Model 6-week old KC mice were treated with Compound 8C via oral gavage (30 mg/kg body weight, daily). The resulting effect on PanIn levels were observed compared to control mice which did not receive Compound 8C. Mice treated with Compound 8C showed significantly reduced propensity for developing PanIn (Pancreatic Intraepithelial Neoplasia), a type of pancreatic duct lesion, as shown in FIG. 13.

Example 58: Effect of Compound 8C in a Head and Neck Tumor Model

Figure 14:
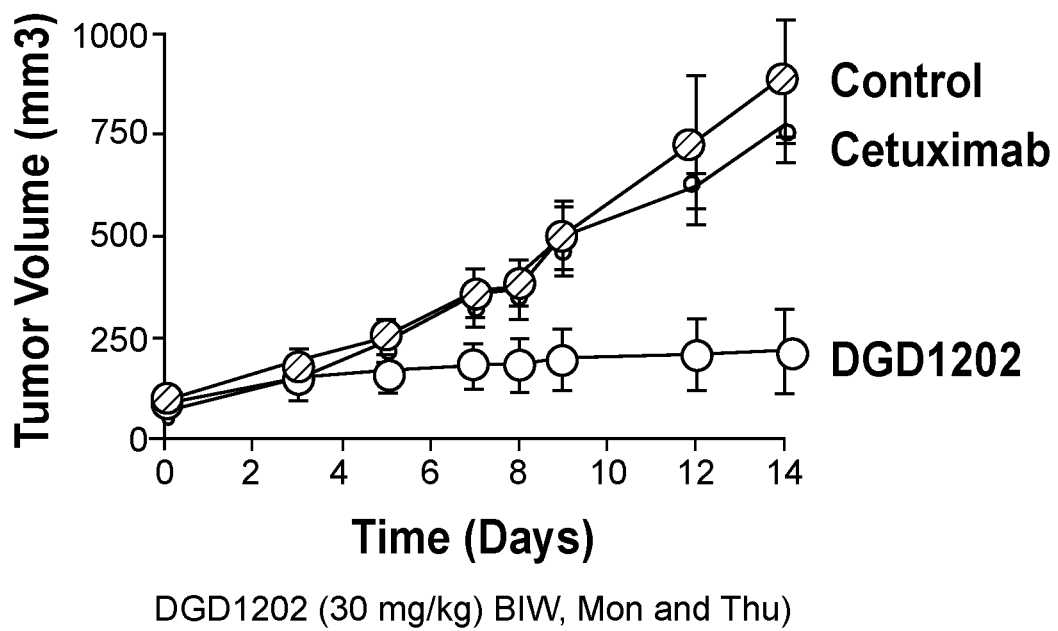
FIG. 14 shows that mouse xenographs bearing the UMSCC74B head and neck tumor model, treated with Compound 8C displayed significantly smaller tumors compared to control mice which received either treatment vehicle or cetuximab.

Mouse xenographs of UMSCC74B, a head and neck tumor cell line, were treated with Compound 8C via oral gavage (30 mg/kg body weight, twice weekly). The resulting effect on tumor volume was observed compared to control mice which did not receive Compound 8C, and control mice which received cetuximab. Mice treated with Compound 8C showed significantly reduced tumor volume compared to both controls, as shown in FIG. 14.

REFERENCES

1. Midha et al. Am J Cancer Res. 2015;5:2892-911.
2. Dahabreh et al. Clin Cancer Res. 2010;16:291-303.
3. Rudin et al. Clin Cancer Res. 2009;15:5646-61.
4. Balak et al. Clin Cancer Res. 2006;12:6494-501.
5. Yun et al. Proc Natl Acad Sci U S A. 2008;105:2070-5.
6. Bublil et al. Faseb J. 2010;24:4744-55.
7. Soria et al. N Engl J Med. 2018;378:113-25.
8. Niederst et al. Clin Cancer Res. 2015;21:3924-33.
9. Thress et al. Nat Med. 2015;21:560-2.
10. Yu et al. JAMA Oncol. 2015;1:981-3.
11. Arulananda et al. Journal of Thoracic Oncology. 2017;12:1728-32.
12. Jia Y et al. Nature. 2016;534:129-32.
13. Kong et al. Biochem Biophys Res Commun. 2017;488:266-72.
14. Ahsan et al. Neoplasia. 2014;16:105-14.
15. Ahsan et al. J Biol Chem. 2013;288:26879-86.
16. Lichtner et al. Cancer Research. 2001;61:5790-5.
17. WO2012087943-A2; US2012190622; WO2012087943; EP2655401; U.S. Pat. No. 9,029,502; US2015218277.
18. WO2014176475
19. Amador et al. Cancer Research. 2004;64:9139-43.
20. Wheeler et al. Nature Reviews Clinical Oncology. 2010;7:493-507.
21. Pao et al. PLoS Med. 2005;2:e73.
22. Cuneo et al. Pharmacol Ther. 2015;154:67-77.
23. Burslem et al. Cell Chem Biol. 2018;25:67-+.
24. Ray et al. Oncotarget. 2016.
25. Raina et al. Proc Natl Acad Sci U S A. 2016;113:7124-9.
26. Crews et al. J Med Chem. 2016;59:5129-30.
27. Ray et al. Neoplasia. 2015;17:697-703.
28. Bondeson et al. Nature Chemical Biology. 2015;11:611-U120.
29. Shukla et al. Neoplasia. 2014;16:115-28.
30. Hines et al. Proc Natl Acad Sci U S A. 2013;110:8942-7.
31. Ray et al. Neoplasia. 2011;13:570-8.
32. Argiris et al. Clin Cancer Res. 2011;17:5755-64.
33. Ahsan et al. Cancer Res. 2010;70:2862-69.
34. Feng et al. Oncogene. 2007;26:3431-9.
35. Piao et al. Cancer Gene Ther. 2009;16:256-65.
36. Wang et al. J Gene Med. 2013;15:42-50.
37. Spivakkroizman et al. J Biol Chem. 1992;267:8056-63.
38. Ewald et al. Exp Cell Res. 2003;282:121-31.
39. Walker et al. Mol Cell Biol. 1998;18:7192-204.
40. Coban O et al. Biophys J. 2015;108:1013-26.
41. Chung et al. Nature. 2010;464:783-U163.
42. Zhang et al. Nature. 2007;450:741-4.
43. Zhang et al. Cell. 2006;125:1137-49.
44. Torchilin et al. Drug Discov Today. 2003;8:259-66.
45. Ripphausen et al. Drug Discov Today. 2011;16:372-6.
46. Corcoran et al. Cancer Discovery. 2012;2:227-35.
47. Khan et al. Analytical Biochemistry. 2011;417:57-64.
48. Chmielecki et al. Sci Transl Med. 2011;3:90ra59.
49. Lovly et al. Nat Med. 2014;20:1027-34.
50. Ichihara et al. Cancer Research. 2017;77:2990-3000.
51. Yu et al. The AAPS journal. 2011;13:417-26.
52. Sun et al. J Med Chem. 2011;54:3306-18.
53. Cai et al. J Med Chem. 2011;54:2714-26.
54. Zheng et al. Drug metabolism and disposition: the biological fate of chemicals. 2011;39:627-35.
55. Fang et al. Drug metabolism and disposition: the biological fate of chemicals. 2008;36:1153-65.
56. Fang et al. J Clin Pharmacol. 2007;47:227-37.
57. Zou et al. Expert Opin Drug Metab Toxicol. 2012;8:855-72.
58. Han et al. Cancer Lett. 2012;318:124-34.
59. Weihua et al. Cancer Cell. 2008;13:385-93.
60. Wei et al. Cell. 2013;154:1269-84.
61. Li et al. Autophagy. 2010;6:1066-77.
62. Leighl et al. Clin Lung Cancer. 2017;18:34-42.
63. Pan et al. PLoS One. 2015;10.
64. Sangodkar et al. J Clin Invest. 2012;122:2637-51.
65. Ma et al. Blood Cancer J. 2013;3.
66. Morgan et al. Front Oncol. 2017;7.

What is claimed:

1. A compound, or pharmaceutically acceptable salt thereof, having the structure of Formula I:

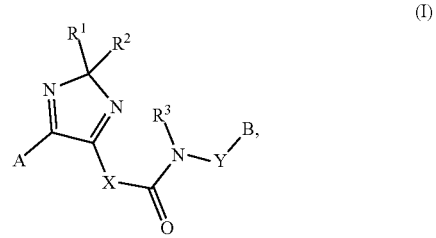

(I)

wherein

X is S—C$_{0-6}$alkylene, and said alkylene is optionally substituted with 1-3 groups independently selected from halo, N(R$^3$)$_2$, and OR$^3$;

Y is null;

A is C$_{6-10}$ aryl optionally substituted with 1 to 3 R$^4$;

B is 5-10 membered heteroaryl having 1-4 heteroatoms selected from N, O, and S, and said heteroaryl is optionally substituted with 1 to 3 R$^5$;

R$^1$ and R$^2$ together with the carbon atom to which they are attached form a 6 membered heterocycloalkyl ring, wherein the heterocycloalkyl ring has 1 or 2 ring heteroatoms selected from O, S, and N, and wherein said cycloalkyl ring or heterocycloalkyl ring is optionally substituted with 1-2 R$^6$;

each R$^3$ is independently H or C$_{1-6}$ alkyl;

each R$^4$ and R$^5$ is independently C$_{1-6}$ alkyl, C$_{1-6}$ haloalkyl, halo, or C$_{1-6}$ alkoxy; and R$^6$ is C$_{1-6}$ alkyl, C$_{1-6}$ haloalkyl, (C=O)R$^3$, (C=O)OR$^3$, CON(R$^3$)$_2$, C$_{0-3}$alkylene-C$_{3-8}$cycloalkyl, C$_{0-3}$alkylene-C$_{6-10}$aryl, or C$_{0-3}$alkylene-(5-10 membered heteroaryl having 1-4 heteroatoms selected from N, O, and S), wherein the aryl or heteroaryl is optionally substituted with 1 to 3 R$^5$.

2. The compound or salt of claim 1, wherein R$^1$ and R$^2$ together with the carbon atom to which they are attached form a heterocycloalkyl ring having the structure:

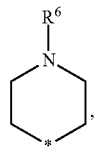

where * indicates the point of attachment to the rest of the compound of Formula I.

3. The compound or salt of claim 1, wherein R$^6$ is C$_{1-6}$ alkyl.

4. The compound or salt of claim 3, wherein R$^6$ is methyl.

5. The compound or salt of claim 1, wherein A is phenyl.

6. The compound or salt of claim 1, wherein B is quinolinyl.

7. The compound or salt of claim 1, wherein A is substituted with one R$^4$.

8. The compound or salt of claim 7, wherein A has the structure:

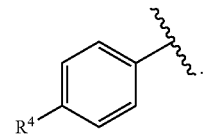

9. The compound or salt of claim 1, wherein at least one R$^4$ is halo.

10. The compound or salt of claim 9, wherein R$^4$ is bromo.

11. The compound or salt of claim 1, wherein R$^3$ is H.

12. A pharmaceutical composition comprising the compound or salt of claim 1 and a pharmaceutically acceptable carrier or excipient.

13. A method of treating cancer associated with aberrant EGFR activity, comprising administering to a subject in need thereof a therapeutically effective amount of the compound or salt of claim 1.

14. The compound of claim 1, wherein R$^1$ and R$^2$ together with the carbon atom to which they are attached form an unsubstituted 6 membered heterocycloalkyl ring.

15. The compound of claim 14, wherein the heterocycloalkyl ring has 1 ring N atom.

16. A compound which is compound 8C:

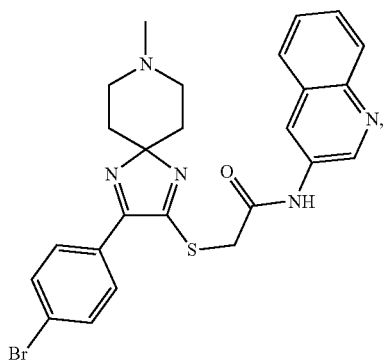

(8C)

or a pharmaceutically acceptable salt thereof.

17. A pharmaceutical composition comprising the compound or salt of claim 16 and a pharmaceutically acceptable carrier or excipient.

18. A method of treating a cancer associated with aberrant EGFR activity, comprising administering to a subject in need thereof a therapeutically effective amount of the compound or salt of claim 16.

19. The method of claim 18, wherein the cancer is non-small cell lung cancer.

20. The method of claim 13, wherein the cancer is non-small cell lung cancer.

* * * * *